United States Patent [19]

Belsito

[11] Patent Number: 5,054,774
[45] Date of Patent: Oct. 8, 1991

[54] COMPUTER-CONTROLLED MUSCLE EXERCISING MACHINE HAVING SIMPLIFIED DATA ACCESS

[75] Inventor: Anne W. Belsito, Chattanooga, Tenn.

[73] Assignee: Chattecx, Hixson, Tenn.

[21] Appl. No.: 537,039

[22] Filed: Jun. 12, 1990

[51] Int. Cl.$^5$ .................... A63B 23/04; A63B 24/00
[52] U.S. Cl. ......................... 272/130; 272/DIG. 5; 272/DIG. 6; 340/712; 128/25 R
[58] Field of Search ................ 272/129, 130, DIG. 5, 272/DIG. 6; 73/379; 128/25 R, 25 B; 434/247, 392; 340/712

[56] References Cited

U.S. PATENT DOCUMENTS

| | | | |
|---|---|---|---|
| 4,235,437 | 11/1980 | Ruis et al. | 272/134 |
| 4,408,613 | 10/1983 | Relyea | 272/670 |
| 4,544,154 | 10/1985 | Ariel | 272/129 |
| 4,566,692 | 1/1986 | Brentham | 272/130 |
| 4,586,035 | 4/1986 | Baker et al. | 340/712 |
| 4,601,468 | 7/1986 | Bond et al. | 272/130 |
| 4,637,607 | 1/1987 | McArthur | 272/129 X |
| 4,691,694 | 9/1987 | Boyd et al. | 128/25 R |
| 4,711,450 | 12/1987 | McArthur | 272/129 |
| 4,714,244 | 12/1987 | Kolomayets et al. | 272/72 |
| 4,765,613 | 8/1988 | Voris | 272/129 |
| 4,779,080 | 10/1988 | Coughlin et al. | 340/712 |
| 4,817,940 | 4/1989 | Shaw et al. | 272/93 |
| 4,828,257 | 5/1989 | Dryer et al. | 272/DIG. 5 |
| 4,842,274 | 6/1989 | Oosthuizen et al. | 272/129 |
| 4,848,152 | 7/1989 | Pratt, Jr. | 73/379 |

OTHER PUBLICATIONS

LIDO Active Isokinetic Rehabilitation System Operations Manual Loredan Biomedical, Inc., 9/1988.
Dynatrac Strength Rehabilitation brochure by Med-Ex Diagnostics of Canada, Inc.

Primary Examiner—Richard J. Apley
Assistant Examiner—L. Thomas
Attorney, Agent, or Firm—Bell, Seltzer, Park & Gibson

[57] ABSTRACT

A data access method and apparatus for computerized control of a muscle exercising machine, allows large amounts of data to be stored and retrieved with minimal computer skill. The muscle exercising machine displays a window or "scroll box" on its display device in response to an appropriate selection of a first type of data to be retrieved. The window contains a list of at least some of the names of the first type of data to be retrieved and a selection area for highlighting one name in the list of the first type of data in the window. The list can be scrolled in the up or down direction via a touch screen to locate a data file within a selection area of the window or scroll box.

The window and up/down selection options may be used to simplify storage and retrieval of patient data. In response to a selection command, at least some of the names of users are displayed and one name is selected. Then, at least some of the dates of exercise for the selected name are displayed and one date is selected. Then, at least some of the exercises performed by the selected name on the selected date are displayed. One of the exercises may be selected, and the exercise machine may be controlled to perform the selected exercise.

The muscle exercise machine may be controlled using the window and up/down option to permit exercising of standard exercises including isokinetic, isotonic and isometric exercises. The exercise machine may also be controlled to permit creation and retrievals of customized exercise protocols, based on previously defined protocols. The protocols are defined using the touch screen interface as well as the window or scroll box.

60 Claims, 60 Drawing Sheets

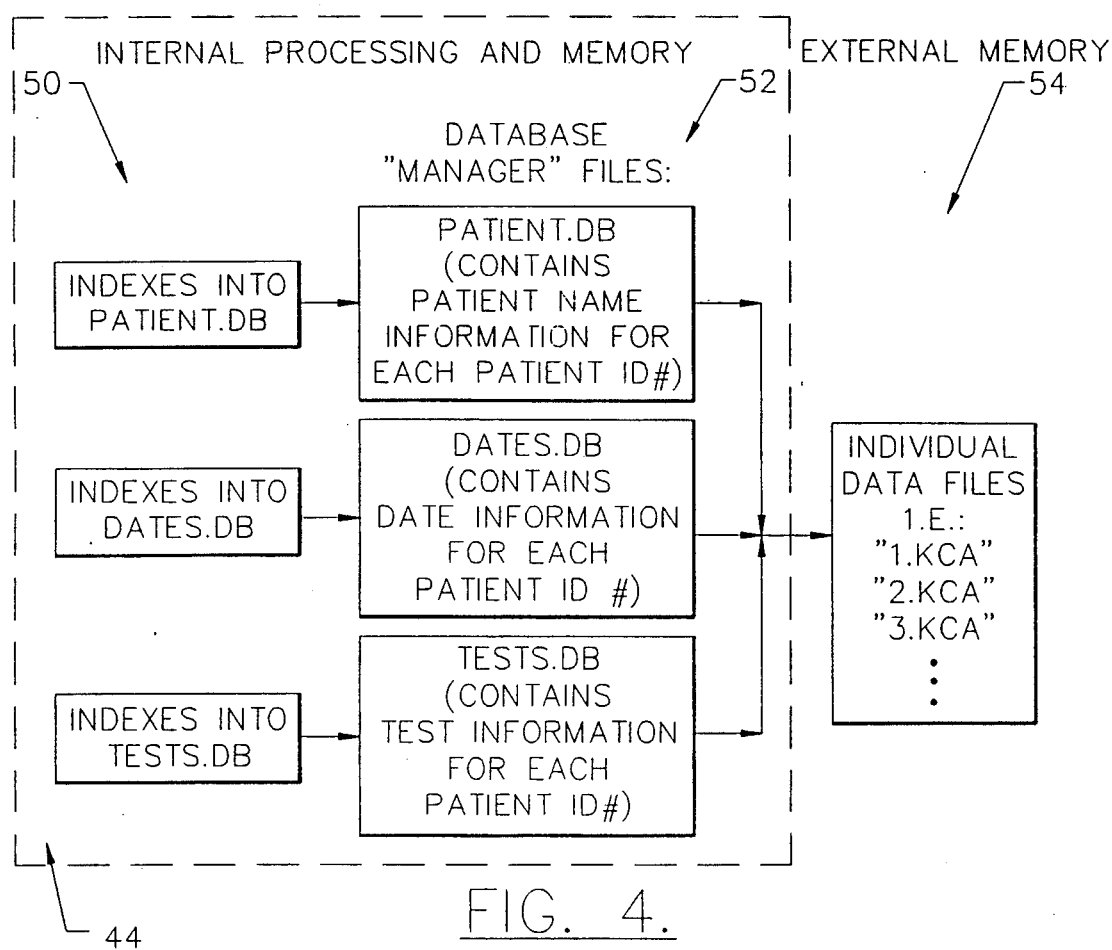

```
            KIN COM
      PROTOCOL - ISOMETRIC

SPEED OF EXERCISE          FORCE SETTINGS
  SPEED FORWARD:     10      START FORWARD FORCE:     0 N
  SPEED BACKWARD:    10      START BACKWARD FORCE:    0 N
                             MINIMUM FORCE:           0 N
  TYPE OF CONTRACTION: CON/ECC  MAXIMUM FORCE:     2000 N
TURNING POINTS             PAUSE SETTINGS
  FORWARD:           LOW      PAUSE FORCE:           100 N
  BACKWARD:          LOW      PAUSE TIME:            500

CONSTANT           SPEED    MARKER SETTINGS
                              MARKER 1:              100
RETETITIONS PER SET  10       MARKER 2:              150
NUMBER OF SETS        0
RECOVERY TIME         0

ESC             1 SAVE           BEGIN EXERCISE
```

FIG. 6M.

```
            KIN COM
      ISOKINETIC TRAINING
           CON/ECC

1 CONTINUOUS        2 OVERLAY

3 STORE EXERCISE:   OFF

ESC
```

FIG. 6N.

```
                    KIN COM
                STANDARD RESULTS
                                    UP
                   1 SPEED: CON/ECC  60  60  RIGHT ULNAR/RAD DEV
TEST #2            2 SPEED: CON/ECC  60  60  LEFT ULNAR/RAD DEV
Patient: JON SMITH 3 SPEED: CON/ECC  30  30  RIGHT ULNAR/RAD DEV
Date: 11-27-89     4 SPEED: CON/ECC  60  60  RIGHT ULNAR/RAD DEV
Test:              5 SPEED: CON/ECC  60  60  LEFT ULNAR/RAD DEV
                   6 SPEED: CON/ECC  30  30  RIGHT ULNAR/RAD DEV
                   7 SPEED: CON/ECC  60  60  RIGHT LUNAR/RAD DEV
                                   DOWN

ESC       SELECT PATIENT   SELECT DATE          ACCEPT
```

FIG. 6GG.

```
                    KIN COM
                STANDARD RESULTS

TEST #1
 PATIENT: JON SMITH
 DATE: 11-27-89
 TEST: SPEED:  CON/ECC  60  60 RIGHT
       ULNAR/RAD DEV

TEST #2
 PATIENT: JON SMITH
 DATE: 11-27-89
 TEST: SPEED:  CON/ECC  60  60 RIGHT
       ULNAR/RAD DEV

ESC              REDO TEST              DISPLAY
```

FIG. 6HH.

```
         KIN COM
       STANDARD RESULTS
              ┌─────────────────┐
              │       UP        │
              ├─────────────────┤
TEST #1       │ alice fadden    │
Patient:      │ JAN JONES       │
Date:         │ JON DOE         │
Test:         │ JON SMITH       │
              │ SMITH           │
              │ Stig Wretzen    │
              │ terri           │
              ├─────────────────┤
              │      DOWN       │
              └─────────────────┘

[ESC]                                [ACCEPT]
```

FIG. 6KK.

```
         KIN COM
       STANDARD RESULTS
                      ┌──────────────┐
                      │      UP      │
                      ├──────────────┤
TEST #1               │  4-15-89     │
Patient: JON SMITH    │  01-19-90    │
Date:                 │  10-03-89    │
Test:                 │  10-13-89    │
                      │  11-27-89    │
                      │  12-19-89    │
                      │  12-27-89    │
                      ├──────────────┤
                      │     DOWN     │
                      └──────────────┘

[ESC]                                [ACCEPT]
```

FIG. 6LL.

```
             KIN COM
         CONTINUOUS RESULTS
                     ┌──────────┐
                     │    UP    │
  TEST #1            │ 1- 5-90  │
  Patient: JON SMITH │ 2- 5-90  │
  Date:              │ 3- 4-90  │
  Test:              │ 3- 5-90  │
                     │ 3- 6-90  │
                     │ 3-15-90  │
                     │ 4-25-90  │
                     │   DOWN   │
                     └──────────┘

[ESC]                              [ACCEPT]
```

FIG. 600.

```
             KIN COM
         CONTINUOUS RESULTS
                     ┌────────────────────────────────────┐
                     │                UP                  │
  TEST #1            │ 1 SPEED: CON/ECC 30 30 RIGHT   EXT │
  Patient: JON SMITH │ 2 SPEED: CON/ECC 30 30 RIGHT   EXT │
  Date: 3- 5-90      │ 3 SPEED: CON/ECC 30 30 RIGHT   EXT │
  Test:              │ 4 SPEED: CON/ECC 30 30 RIGHT   EXT │
                     │ 5 SPEED: CON/ECC 30 30 RIGHT   EXT │
                     │ 6 SPEED: CON/ECC 30 30 RIGHT   EXT │
                     │ 7 SPEED: CON/ECC 30 30 RIGHT   EXT │
                     │               DOWN                 │
                     └────────────────────────────────────┘

[ESC]                                          [ACCEPT]
```

FIG. 6PP.

```
3- 5-90     03-03-56    /JON SMITH
Joint      :  Right Knee        (Lever arm = 30 cm)

Parameters: SPEED mode, CON/ECC
Speed of movement : Forth = 30, Back = 30 o/s   Acc:MEDIUM,Dec:MEDIUM
Start Force         : Forth = 11, Back =  11 Lb  Pause: Time  0.0
Force limits        : Low   =  4, High = 450 Lb          Force 22Lb File          : 4.KCT
Stored data : 20 s ESC         *press anywhere to continue*
```

COMPUTER-CONTROLLED MUSCLE EXERCISING MACHINE HAVING SIMPLIFIED DATA ACCESS

FIELD OF THE INVENTION

This invention relates to muscle exercising machines, and more particularly to computer controlled exercising machines which are capable of performing many types of exercise for testing, training and/or rehabilitation.

BACKGROUND OF THE INVENTION

Computer-controlled muscle exercising machines are widely used for muscle evaluation, training, and/or rehabilitation. During evaluation, the strength of a particular muscle is tested so that an exercise or rehabilitation program may be set up. During training or rehabilitation, the strength of a muscle is gradually improved by a programmed set of exercises.

Computer controlled exercising machines may often be configured to exercise different joints or muscles. They may also generally be programmed to exercise a particular joint or muscle according to one or more of the following types of exercise: isometric, isotonic, isokinetic and constant power. In isometric exercise, the rate of angular change or velocity of the limb is zero while the force can be in either of two directions. In isotonic exercise, the load or resistive force has constant value while the velocity varies. In isokinetic exercise the force is allowed to vary to match the user's force in such a way that the velocity is kept constant. In constant power exercise both velocity and force are allowed to vary such that their product is kept constant. Finally, computer controlled exercise machines may also be configured to provide a predetermined amount of force or velocity, over a predetermined range of motion, for a predetermined number of repetitions in a set and with predetermined rests between sets of repetitions.

Computer controlled exercise machines generally include at least one exercise element which is adapted for manipulation by a user, and a computer controller which is operationally connected to the exercise element for controlling the movement of the exercise movement upon manipulation by a user. Generally, computer controlled exercise machines also include a display connected to the controller, for assisting in configuring the machine and for providing user feedback in the form of graphical or numeric displays during the course of exercise. An input device is also generally provided to allow a user or a physical therapist to configure the machine for performing a particular exercise or sets of exercise.

One example of a highly successful computer-controlled exercise machine is the Kin-Com ® Models 2 and 3 muscle testing and training systems manufactured and marketed by Chattecx Corporation, Chattanooga, Tenn. The electro-mechanical operation of the Kin-Com ® Models 2 and 3 is described in U.S. Pat. No. 4,711,450 to McArthur, assigned to the assignee of the present invention, the disclosure of which is hereby incorporated herein by reference. Other computer controlled muscle exercise machines are disclosed in U.S. Pat. Nos. 4,408,613 to Relyea, 4,235,437 to Ruis et al., 4,842,274 to Oosthuizen et al.; 4,691,694 to Boyd et al. and 4,601,468 to Bond et al.

A major problem in the use of computerized muscle exercising machines is the control of these machines. Although computer control provides a high degree of flexibility and adaptability, computer controlled machines are often difficult to configure and to control. This is a major problem for the typical user of a computer controlled exercising machine, who is typically unskilled in the operation of a computer. Moreover, in a physical therapy program, the machine is typically configured by a physical therapist who is responsible for administering physical therapy programs for many patients on the machine, and for configuring the machine appropriately for each patient. Physical therapists are typically unskilled in computer use, so that proper operation of the computerized muscle exercise machine is often a major concern.

In an effort to simplify the use of a computerized muscle exercising machine, these machines have often incorporated touch screen user input devices instead of or in addition to conventional keyboards. As is well known to those having skill in computer art, a touch screen is a device which is mounted on the face of a cathode ray tube or other display, and which accepts user inputs by touching an appropriate portion of the display. When using a touch screen, the computer controller may be configured to display appropriate selection boxes or areas on the touch screen. The touch screen is responsive to a finger or other object touching one of the designated areas for accepting a user response. By eliminating or reducing the need for a keyboard, simplified ("user friendly") control may be obtained.

A computerized rowing machine which may include a touch screen is disclosed in U.S. Pat. No. 4,714,244 to Kolomayets et al. A computerized exercise machine including a touch screen has also been marketed by Med-Ex Diagnostics of Canada as the Dynatrac TM system. In the Dynatrac TM system, a touch screen is used to set up exercises.

A major problem in controlling computerized muscle exercising machines is the storage and retrieval of large volumes of exercise related data. Exercise related data must be stored and retrieved in order to monitor the progress of an exercise or rehabilitation program, to calibrate the exercise machine based on past exercise, and to generate reports to doctors, insurance companies and patients.

Two examples of exercise related data are "patient data" and "protocol data". "Patient data" includes the cumulative exercises performed by a patient during the course of multiple sessions in an exercise or rehabilitation program. It will be understood by those having skill in the art that many users and/or patients typically use the exercise machine at different times. The machine must be calibrated for each user in terms of the muscle being exercised, the amount of force, degree of rotation, range of motion, type of exercise and many other parameters. Failure to correctly calibrate the machine may injure an already injured muscle. Accordingly, a given patient's data must be easily retrievable in order to configure the machine for a session. Moreover, any patient's data must be retrievable so that different patient's progress may be compared, or exercises may be set up for a new patient based upon those being used by an existing patient.

A second example of exercise related data is "protocol data". Protocol data describes a particular type of exercise for a particular type of muscle using a particular set of parameters. As described above, exercise machines may typically be configured for isometric, isotonic, isokinetic, constant power and other types of exercise. Moreover, for each particular joint or muscle, a certain range of motion, force, number of exercises and rests between exercise may be desired. These resulting permutations can create a large number of exercise "protocols" which may be used. Moreover, typically an exercise machine is used by more than one trainer or physical therapist, each of whom may have his own set of protocols which are used over and over again for patients. Accordingly, simplified retrieval of a protocol from a large number of protocols is desirable.

The computer-controlled muscle exercising machines described above have had some difficulty in manipulating large amounts of exercise related data. For example, the Kin-Com® Models 2 and 3 systems described above store exercise related data on a nonremovable magnetic disk (a "hard disk") coupled to the computer controller. Patient data for each exercise session for each user is stored using a file name arbitrarily assigned by the user, trainer, or physical therapist. The file name must be recorded separately on a paper or in a patient's folder for later retrieval of the data. Unfortunately, a file name so recorded is often lost so that the patient data is not retrievable. Moreover, for many sessions performed on many patients, it is difficult to keep track of the file names assigned for each test. Also, the same physical therapist may not always supervise the exercising of a given patient so that exercises on different days may be stored under inconsistent file names. Simple and accurate storage and retrieval of patient data is difficult.

The Kin-Com® Models 2 and 3 also allow for new protocols to be set up, stored and retrieved using an operator assigned sequential number identifier. All protocols are stored within the same file and identified by the unique sequential number identifier. It is difficult to track the large numbers of protocols typically used in a clinic. Moreover, it is difficult for a trainer or physical therapist to retrieve a previously stored protocol.

Another approach for managing large amounts of exercise related data is used by the above mentioned Dynatrac ™ machine. In the Dynatrac ™ machine, a disk file is not used for storing large amounts of data. Rather, exercise related data is stored on "patient data cards" each of which includes a small nonvolatile storage in which a small amount of data on up to eight patients may be stored. In order to store and retrieve data, the appropriate card is inserted into the computer controller. Unfortunately, the use of patient data cards does little to alleviate the data storage and retrieval problem. The individual cards are easily lost or the wrong card may be inserted into the machine for a given patient. The cards are expensive, and a large inventory of cards must be maintained because a limited amount of data may be stored on each card. The cards are prone to break upon repeated use. Moreover, since each card contains a limited amount of data, no standard protocols are contained on the card. Standard protocols and customized protocols cannot be set up. Rather, each exercise must be set up with its own set of parameters whereby every parameter must be set by the operator. Accordingly, a large amount of exercise related data cannot be simply stored and retrieved.

SUMMARY OF THE INVENTION

It is therefore an object of the present invention to provide an improved computer-controlled muscle exercising machine.

It is another object of the present invention to provide an improved data access method and apparatus for a computer-controlled muscle exercising machine.

It is still another object of the present invention to provide a data access method and apparatus for a computer-controlled muscle exercising machine which does not require creating or memorizing large numbers of arbitrarily named file names in order to store and retrieve exercise related data.

It is yet another object of the invention to provide a data access method and apparatus for a computer-controlled muscle exercising machine which can store and retrieve large amounts of data in a manner which requires minimal computer skills.

These and other objects are provided according to the present invention by a muscle exercise machine which displays a window also referred to as a "scroll box", on its display device in response to an appropriate selection of a first type of data to be retrieved. The window contains a list of at least some of the names of the first type of data to be retrieved and a selection area for highlighting one name in the list of the first type of data in the window.

The exercise machine accepts the user selection of an UP option or a DOWN option. In response to the UP option, one or more names is added to the top of the list and a corresponding one or more names is deleted from the bottom of the list and the entire list is moved down in the window so that a preceding name on the list is moved into the selection area. In response to the DOWN option, one or more names is deleted from the top of the list, one or more names is added to the bottom of the list and a succeeding name on the list is moved into the selection area. Accordingly, the UP and DOWN options can be repeatedly selected to move up and down a long list of names, a portion of which is displayed in the window. When the desired name is present in the selection area, an indication can be provided to select that name. The controller then controls the exercise machine in response to the selected name.

In a preferred embodiment, the user selection means is a touch screen which is mounted on the display, and the UP and DOWN options are provided by an UP box displayed above the window and a DOWN box displayed below the window. Selection of the UP box moves up the list, and selection of the DOWN box moves down the list.

The window and UP/DOWN selection options may be used to simplify storage and retrieval of patient data and protocol data according to the present invention. In particular, for patient data, the names of all users of the exercise machine, all of the corresponding dates of use of the exercise machine and all of the corresponding exercises performed on each particular date are stored in a data storage means such as a hard disk. In response to a user selection command, at least some of the names of the users are displayed on the display and a selection may be made for one of the names from the list. Then, in response to the selection, at least some of the dates of exercise for the selected name are displayed on the screen and a selection is accepted for one date. Then, at least some of the exercises performed by the selected name on the selected date are displayed on the screen.

One of the exercises may be selected, and the exercise machine may be controlled to perform the selected exercise.

In a preferred embodiment, the names, dates, and exercises are each displayed in a window on the display device with the window including a list of at least some of the names, dates, or exercises from all the names, dates and exercises stored on the storage device. Upon displaying a list, an UP and DOWN option may be used to move up and down the list. When moving up the list, the top name is deleted, a new name is added to the bottom and the immediately preceding name is moved to the selection area. In the preferred embodiment, the up and down options are selected by providing an UP and a DOWN box at the top and bottom of the window, respectively.

For protocol data, upon operator selection to crate a new protocol, at least some of the names of protocols, including standard protocols and previously defined custom protocols, are displayed in a window on the display device. An UP and DOWN option may be used to move up and down the list as described above. Once the desired protocol is selected it may be used as the basis for creating a new protocol. In other words, a new protocol may be created which is a variation of the selected protocol. Once created and named, the newly created protocol will reappear in subsequent displays of protocols. The window and UP/DOWN options may also be used to display all existing protocols and select a protocol for a current exercise session, or to select a protocol to create a new protocol for a current exercise, without storing the newly created protocol for later retrieval.

The window ("scroll box") and UP/DOWN selection options of the present invention allow a large list of data to be selected by moving up and down the list until the appropriate data element is found. Then, the data associated with that data element may be displayed for further manipulation. This data may be displayed by again displaying a list of data in a window and allowing up/down selection. Accordingly, data may be stored and retrieved using the window and UP/DOWN options without requiring the user to know how the data is organized and without requiring the user to assign or remember a file name for the data. The computer controlled muscle exercise machine assigns file names and stores the data to permit retrieval. Large amounts of exercise related data, such as may be used with a computer controlled exercise machine, may be manipulated easily.

BRIEF DESCRIPTION OF THE DRAWINGS

A preferred form of the invention is illustrated in the accompanying drawings in which:

FIGS. 3A, 3B and 3C illustrate the scroll box or window of the present invention;

FIG. 4 illustrates a database structure for the present invention;

DESCRIPTION OF THE PREFERRED EMBODIMENT

The present invention now will be described more fully hereinafter with reference to the accompanying drawings, in which a preferred embodiment of the invention is shown. This invention may, however, be embodied in many different forms and should not be construed as limited to the embodiment set forth herein; rather, this embodiment is provided so that this disclosure will be thorough and complete, and will fully convey the scope of the invention to those skilled in the art. Like numbers refer to like elements throughout.

OVERVIEW: COMPUTER CONTROLLED EXERCISE MACHINE

Figure 1:
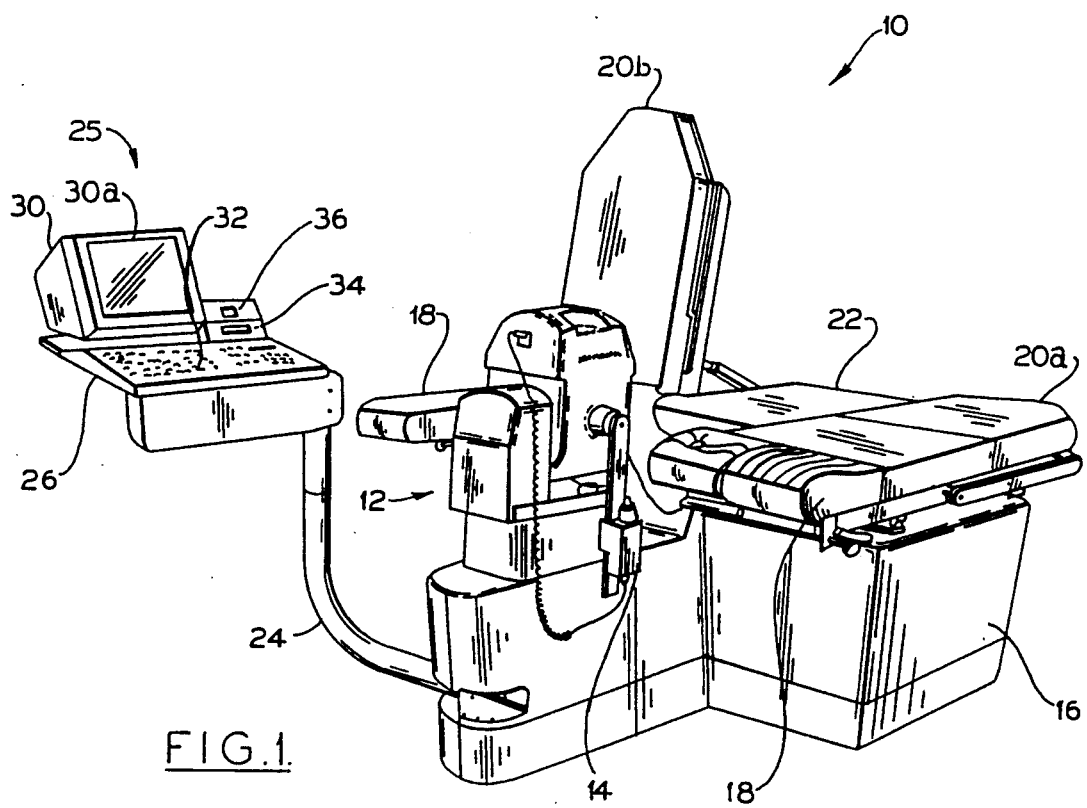
FIG. 1 is a perspective view showing a computer-controlled muscle exercise machine according to the present invention.

Referring to FIG. 1, a general overview of a computer controlled muscle exercising machine 10 will be described. Exercising machine 10 consists of an actuator assembly 12 to which exercise element 14 is attached. The exercise element may be referred to as an exercising member or arm. A variety of types of attachments may be fixed to exercise element 14 to accommodate exercising of arm, leg, or other body parts. Handles in the form of forearm or wrist grips may be attached to exercise element 14. Housing 16 encloses a hydraulic pump and heat exchanger and also supports cushions 18, 20, and 22. Cushions 18 support the thigh of the patient. Upper body chair cushions 20 may remain in a horizontal position as indicated at 20a or in an upright position as indicated at 20b. Center cushion 22 is located directly between each set of cushions 18 and 20. The mechanical operation of muscle exercising machine 10 is further described in U.S. Pat. No. 4,711,450 to McArthur, assigned to the assignee of the present invention, the disclosure of which is hereby incorporated herein by reference.

Ergo arm 24 is attached at one end to the front lower portion of housing 16. The opposite upper end of ergo arm 24 is attached to portable hardware table 26. Ergo arm 24 swivels from one side to the other of the exercising machine as a result of its swivel attachment to the base of housing 16. This swivel action permits an operator of the exercising machine to operate the computer controller 25 located on the portable hardware table from either side of the machine, and permits the patient-/athlete to view any output residing on monitor 30.

The computer controller 25 of computer controlled muscle exercising machine 10 consists of computer housing (not shown) which is located behind housing 16, monitor 30 including display 30a, keyboard 32, one or more external "floppy" disk drives 34 and an "install stop" indicator light 36. A "touch screen" (not shown) is mounted on the face of display 30a to allow display 30a to operate as an input device for the computer controller of exercising machine 10. Keyboard 32 is an alternative input device for the computer controller.

Several hardware components are provided, some of which are contained in a computer housing, including a microprocessor integrated circuit chip. Preferably, the microprocessor is an 80286 microprocessor. The hardware as well as the system and application software are compatible with the IBM PC/AT ® machine. A 20 megabyte hard disk drive is provided in addition to the internal 640K microprocessor memory. External disk drives 34 are 3.5 inch in size. Monitor 30 is a color monitor controlled by a color card in housing 28. Additionally, a color printer (not shown) with a computer stand is provided for hard printouts of patient evaluation and exercise data. The touch screen is preferably a model E274 touch screen, marketed by Elographics, Inc. and mounted on the face of display 30a. A touch screen interface card, for interfacing the touch screen with the microprocessor may be mounted in monitor 30 or in computer housing 28. A suitable card is the model E271-60 marketed by Elographics, Inc.

The computer hardware operates at 12 Mhz with zero wait state. Additionally, a 12/8 Mhz switchable system clock is provided. Finally, data integrity is ensured with an on-board battery backup for the internal and external memory.

Figure 2:
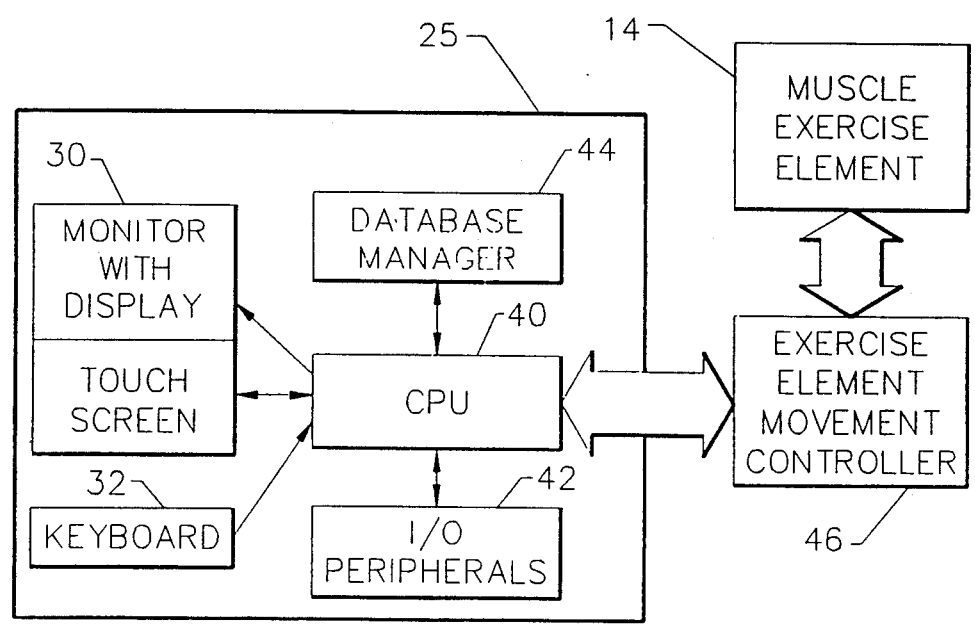
FIG. 2 is a schematic block diagram of the computer hardware used in FIG. 1.

Referring to FIG. 2, a hardware block diagram for the computer controlled exercise machine will now be described. The computer controller 25 consists of central processing unit (CPU) or microprocessor 40, input-/output (I/O) peripherals 42 such as floppy and hard disk drives, database manager 44, and user interfaces including monitor with a display 30 containing a touch screen interface and keyboard 32. The database manager is typically a stored program which runs on CPU 40. The central processing unit 40 communicates with an exercise element movement controller 46 (such as a servo system) which in turn controls the muscle exercise element 14.

OVERVIEW: DISPLAY WINDOW

The present invention simplifies data access and retrieval by providing a window on display 30a. This window may be used in conjunction with a touch screen to select data for access and retrieval. The window contains a list of data, i.e. patient names, dates, etc., and a highlighted or horizontal selection area for highlighting one name. UP/DOWN selection options also are provided in the window area of the display. Referring to FIGS. 3A, 3B and 3C, an example of the window with the horizontal selection area and UP/DOWN option boxes which may be displayed on display 30a are shown for patient name data. In FIG. 3A, the names Jan through Lorna appear alphabetically in the window. These names are seven names from a long list of patient names. The UP box is located above the name Jan and the DOWN box is located below the name Lorna.

The highlighted or horizontal selection area resides in the middle of the window and does not physically move. Rather, the data located within the selection area of the window changes. For example, assume the patient to be processed has the name Jan. In order to bring the patient name Jan into the selection area, the UP option is selected. As previously described, the preferred embodiment provides a touch screen. Therefore, the UP option is indicated by touching the touch screen at the location indicated by the UP box. The result will be shifting of the patient name data downward. Preferably, each selection of the UP option shifts the data by one position. The result of three UP selections is illustrated in FIG. 3B where patient name Carol is located at the top of the window, patient name Joyce is located at the bottom of the window, and patient name Jan is located within the selection area. This is accomplished by deleting the name Lorna, Linda and Kim in order from the bottom of the list and adding Evelyn, Elaine and Carol in order to the top of the list. It will be understood by those having skill in the art that each UP selection may shift the list by more than one position.

The data item, in this case, patient name data, located within the selection area of the window may also be moved in a downward direction. Assume for purposes of illustration that the operator desires to work on the data stored in relation to patient name Lorna. In order to bring patient name Lorna within the selection area, the patient names within the window must be scrolled downward in a vertical direction. This is accomplished by selecting the DOWN option or box. The DOWN option is selected in the preferred embodiment by making an indication at the DOWN box on the window located on display 30a. The DOWN box is continuously pressed on the touch screen until patient name Lorna is located within the highlighted or horizontal selection area. The result is illustrated in FIG. 3C, with patient name Joyce located at the top of the window, patient name Sandy located at the bottom of the window and patient name Lorna located within the selection area. This is accomplished by deleting all the names at the top of the list in order preceding or above Joyce and adding all names at the bottom of the list in order succeeding or below Joyce.

When the desired data is located within the highlighted or horizontal selection area of the scrolling window, the operator may indicate the selection by pressing an ACCEPT box or option on the touch screen or the RETURN key or ENTER key on the keyboard. As a result of the selection by the operator of some specified data, more detailed data associated only with the data item selected will appear on display 30a. The associated detail data may appear on display 30a in a window as previously described. Examples of more detailed associated data include patient test dates, patient protocols, and patient test results. These examples will be described in detail below.

OVERVIEW: DATABASE ARCHITECTURE

The database architecture for the present invention is illustrated in FIG. 4. The database architecture underlying the above described user/operator data manipulation interface provides a database management system based upon an Indexed Sequential Access Method (ISAM). In particular, referring to FIG. 4, the database manager 44 operates upon database manager files 52 and indexes 50 which preferably reside on internal or random access memory controlled by CPU 40. The database manager also operates upon individual data files 54, which preferably are resident on hard disk or other external memory 54 in an I/O peripheral 42 (FIG. 2).

The database manager 44 resides within the processor 40 and the necessary data including indexes 50 and database files 52 are stored in internal memory. The data files stored in external memory are sequential files and are indicated generally at 54. The sequential data files 54 include files which contain patient name data, date data and test data for each patient. Referring to FIG. 4, an example of the data files are generally identified at 54 as 1.KCA, 2.KCA, and 3.KCA. Data files for "overlay" type results are designated as KCA. Data files designated as KCT refer to those for "continuous" type results. A separate data file is provided for each test session for each patient. A maximum of twelve tests can be stored in one data file. Each data file contains all data corresponding to a test including patient information, parameter values and test result data.

Accessing of these data files 54 from external memory results in storage of portions of the data files in internal memory. The database manager then assigns a unique patient ID number to each unique patient name. When a user makes a selection in the horizontal selection area of a patient name, data or test, the appropriate patient ID number is selected by the database manager. The index keys at 50 for the sequential database files 52 are based upon the unique patient ID numbers. The database files at 52, i.e. patient.DB, dates.DB, and tests.DB, contain patient name, date, or test information respectively for each patient ID number. The information is in the form of pointers to the location of the actual data in external memory 54. The accessing logic to the sequential database files is accomplished by searching a binary tree structure using the index key, i.e. patient ID number, at 50, to locate the appropriate pointer in the corresponding database files at 52. Once the appropriate pointer in the database file has been located based upon the patient ID index, the pointer is used to sequentially access the desired data in data files 54. Thus, this process provides an index sequential access method.

The operation of an Indexed Sequential Access Method (ISAM) database access scheme will be understood by those skilled in the art and will not be further explained as part of this detailed description. The details of the user/operator operation of the data storage means and means for accepting and selecting data resulting in computer control of the exercise element which resides on top of the database architecture will now be described.

DETAILED DESCRIPTION: EXERCISE MACHINE OPERATIONAL CONTROL

Sequence of operations performed to control the exercise machine will now be described in detail with reference to the operational control flow charts of FIG. 5 and the sample display screens of FIG. 6. The flowcharts in FIG. 5 provide the flow control resulting from operator selection of various parameters providing computer control of the exercise machine via the computer controller. It will be understood by those having skill in the art that the flowcharts may be implemented by computer 28, operating under stored program control. The displays illustrated in FIG. 6 are examples of displays which appear on the display screen 30a of monitor 30 at various times during the operator control selection process. The displays are in the form of a touch screen. The touch screen or the keyboard or both the touch screen and the keyboard comprise the input device to the system or computer controller. Touch screens are known to those skilled in the art of computer technology. The operator need only touch the portion of the screen corresponding to the selection which he or she desires to make. The system will then respond according to the selection made by the operator.

In controlling the muscle exercise system, various processes can be accomplished. In particular, training of a patient may be performed via selection of certain parameters resulting in computerized control of the exercise machine. Evaluation may also be accomplished via the process of selection of various parameters by the operator so that the exercise equipment can be controlled in order to evaluate the progress of a patient. As part of the evaluation process, the results of an evaluation session may be stored in memory for future references. Additionally, results of various patient exercises may be obtained via this selection process of various parameters whereby the operator can produce the results in a number of formats. Finally, an operator or system installer may initialize the computer controller through the selection process by selecting various parameters. The operator may indicate a selection of one of these processes from a main manu located on display 30a.

DETAILED OPERATION: TRAINING SELECTION

Figure 5A:
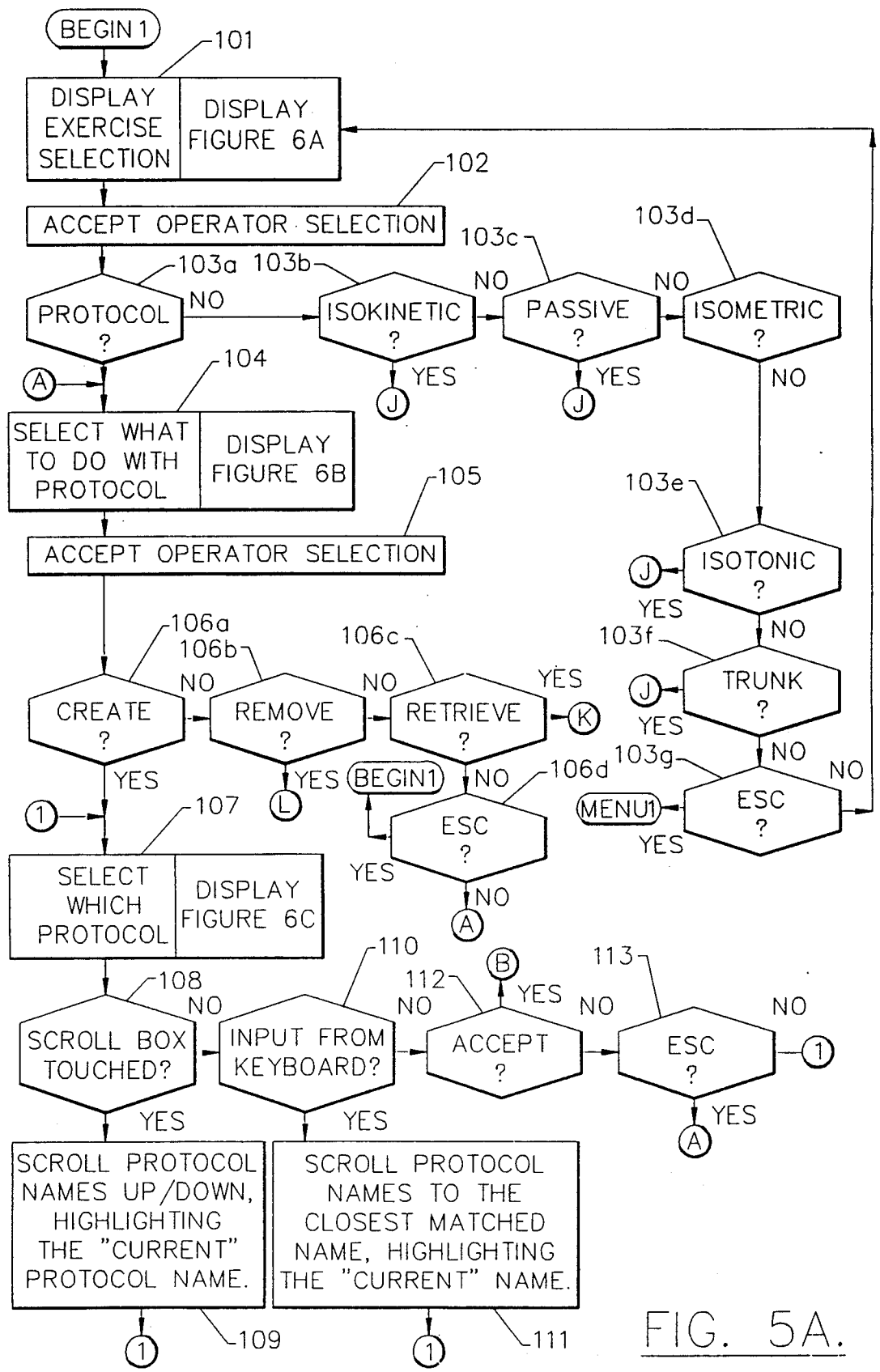
FIGS. 5A through 5MM are flowcharts illustrating operations to control a muscle exercise machine according to the present invention.
Figure 6A:
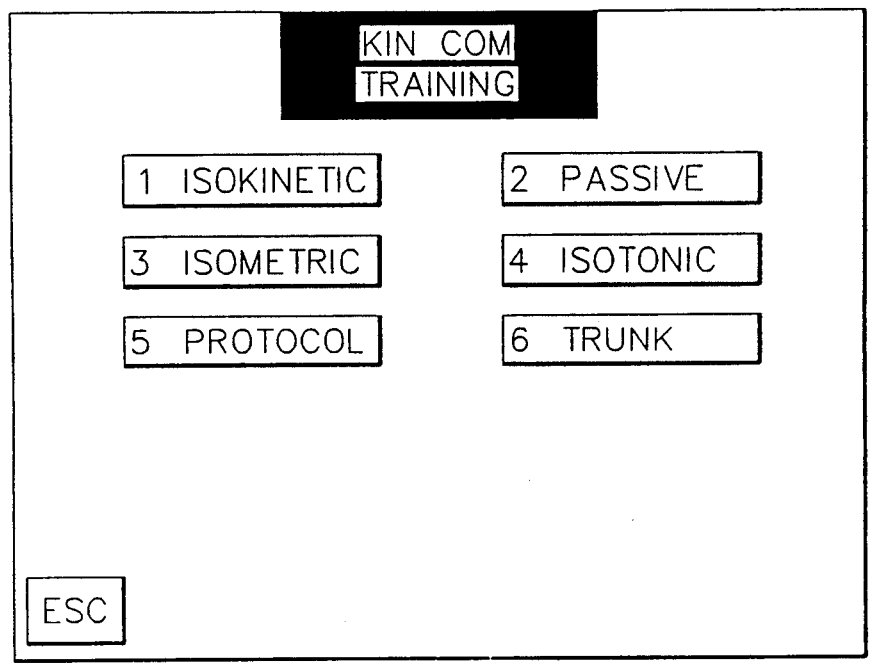
FIGS. 6A through 6XX illustrate display screens which are presented to an operator when controlling a muscle exercise machine according to FIGS. 5A-5MM.

Referring to FIG. 5A, in controlling the muscle exercising machine for patient training or exercising, as indicated by Block 101, the training or exercise options will appear on display 30a. This initial exercise training display is illustrated in FIG. 6A. The operator may select one of the training methods by simply touching the screen within the outlined portion of the desired method. Once a selection has been made as to the training or exercise method, the selection made by the operator is accepted at Block 102.

A number of standard training methods are permanently stored in memory containing preset parameters for specified exercise routines. These standard exercise routines are write protected so that they cannot be deleted by an operator, and include ISOKINETIC, PASSIVE, ISOMETRIC, ISOTONIC and TRUNK training routines. The operator may also select a PROTOCOL training routine which can be defined individually for each patient prior to commencing the training process or retrieved from memory. A determination is made as to which option was selected. This is illustrated generally at 103 as a multiple decision block. Based upon a conclusion that a particular method was not selected, a determination will be made whether the next method was selected.

More specifically, determination is made at 103a whether the PROTOCOL routine was selected. In the event the PROTOCOL routine was not selected, a query is made at 103b whether the ISOKINETIC standard training routine was selected. If the ISOKINETIC standard routine was selected and accepted, control is passed to transition Block J. If a routine or method was not selected, the system continues to make queries as to whether each of the remaining standard training routines were selected and accepted by the system, namely the PASSIVE, ISOMETRIC, ISOTONIC, and TRUNK routines, in that order. If one of those was selected and accepted by the system, control is transferred to transition Block J. If the particular standard routine was not selected and accepted, the system will make a query as to whether the next standard routine in order was selected and accepted. This query process for the remaining standard routines, PASSIVE, ISOMETRIC, ISOTONIC and TRUNK, are indicated at decision Blocks 103c, 103d, 103e and 103f, respectively. In the event that none of the training routines were selected, a determination is made at 103g whether the operator selected the ESCape option. If the ESCape option was selected by the operator, control is returned to a display which permits the operator to select one of the operations which the system is capable of performing, i.e. training, evaluation, results or system initialization including setup and utilities. Based upon a determination at 103g that the ESCape option was not selected, training display Frame 6a will remain displayed on screen dispaly 30a until the operator selects one of the options.

DETAILED OPERATION: PROTOCOL SELECTION

Figure 6B:
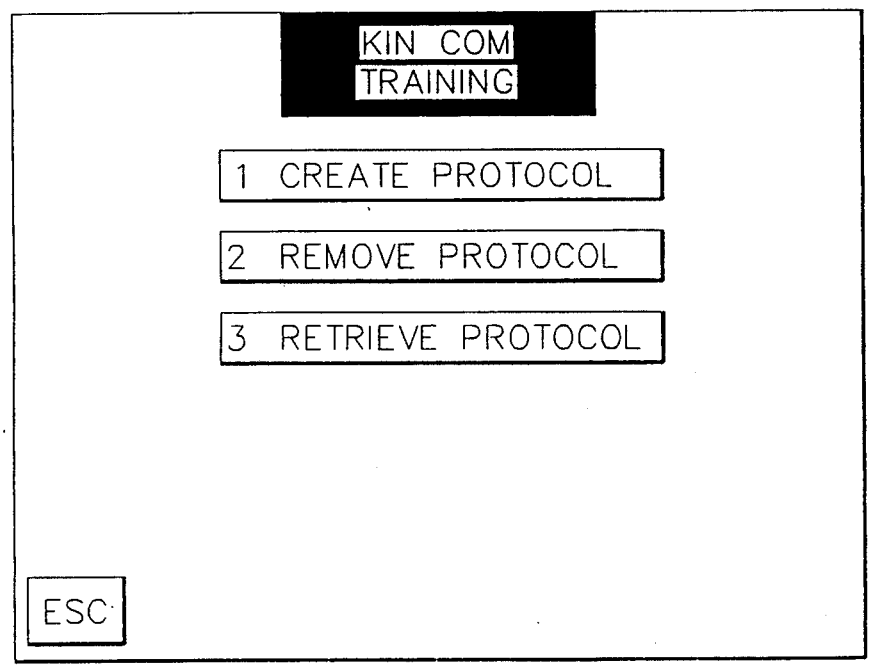

Based upon a conclusion at 103a that the PROTOCOL training routine was selected and accepted, a prompt is displayed at 104 for selection as to what is to be done with the protocol training routine. This prompt displayed at 104 is illustrated in FIG. 6B. The operator is provided with the options of CREATE PROTOCOL, REMOVE PROTOCOL or RETRIEVE PROTOCOL. The operator's selection of creating, removing or retrieving a protocol or in the alternative, escape is accepted at 105.

A determination is made at 106 as to which option the operator selected. This determination is illustrated generally at 106 in FIG. 5A by multiple decision blocks. Based upon a determination at 106a that the option to CREATE a new protocol was selected, control will be passed to Block 106 to permit the operator to select which predetermined protocol he or she desires to use as a basis for creating an operator defined protocol for the particular patient. If the CREATE option was not selected, a determination is made at 106b as to whether removal of an existing protocol was selected. Based upon a conclusion at 106b that REMOVE PROTOCOL was selected, control is transferred to transition Block L.

If the REMOVE PROTOCOL option was not selected, a determination is made at 106c whether the operator chose the RETRIEVE PROTOCOL to retrieve an existing protocol from the database. A standard protocol such as isokinetic or isometric, as well as an operator defined protocol which has been stored in the external data files can be retrieved. Based upon a determination at 106c that RETRIEVE PROTOCOL was selected by the operator, control is transferred to transition Block K. In the event the operator did not select the create, remove, or the retrieve options, a determination is made at 106d whether the ESCape option was selected. If the ESCape option was selected, control is transferred to transition Block BEGIN1 resulting in display at 101 of the training or exercise options, an example of which appears in FIG. 6A. Based upon a determination at 106d that the ESCape option was not selected, control is passed to transition Block A provided for ease of illustration to indicate that the protocol selection menu illustrated in FIG. 6B remains displayed until the operator selects CREATE, REMOVE or RETRIEVE PROTOCOL or ESCape.

DETAILED OPERATION: PROTOCOL CREATION

Figure 6C:
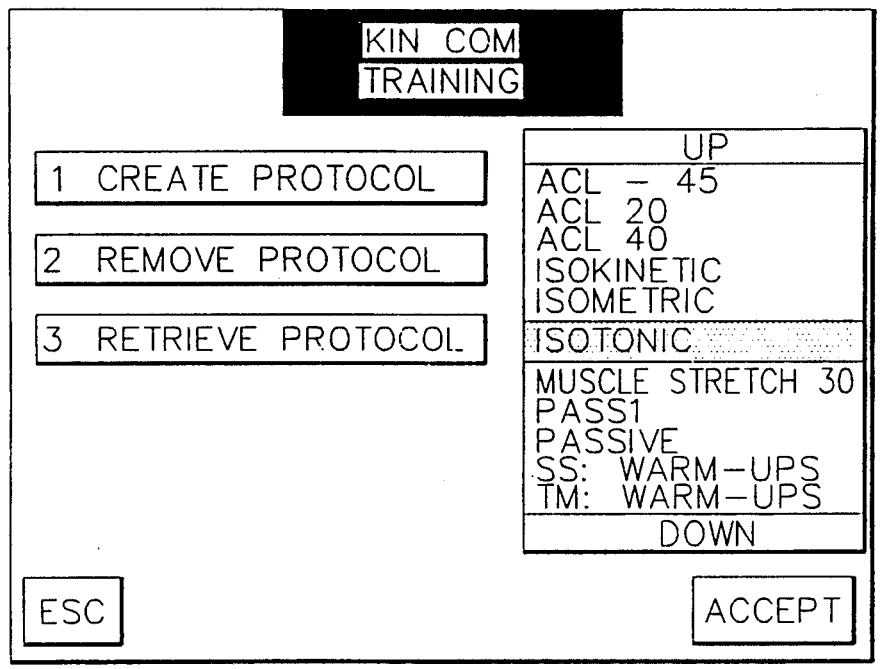

In the event CREATE PROTOCOL was selected, the operator will then be given the option at 107 of selecting which standard protocol, e.g. isokinetic or isometric, or stored operator defined protocol he or she desires to use as the basis for defining the operator defined protocol for the particular patient. An example of identifiers for the predefined or stored operator defined protocols are displayed on display 30a as illustrated in FIG. 6C. FIG. 6C illustrates the window or scroll box and UP/DOWN selection box previously discussed in accordance with FIGS. 3A, 3B and 3C. The operator can make a selection of a predefined or stored operator standard protocol by utilizing the scroll box.

A determination is made at 108 whether the operator touched the scroll box. The operator may touch the scroll box either at the UP indicator or at the DOWN indicator. If the UP indicator was touched, the data listed in the scroll box will move downward at 109 resulting in the previous name being located in the highlighted or horizontal selection area of the window or scroll box. Similarly, if the operator touched the DOWN portion of the scroll box, the data appearing in the window or scroll box will move in an upward direction at 109 resulting in the succeeding name being located in the highlighted or horizontal selection area of the window.

The selection area of the scroll box which appears as a highlighted horizontal strip across the approximately center portion of the scroll box indicates the data item, in this case, either the standard protocol or stored operator defined protocol, which the operator may use as a basis for creating a protocol for the particular patient. Once the desired stored protocol, whether it be standard or operator defined, appears in the horizontal selection area of the window, control is transferred to transition Block 1 in FIG. 5A. Transition Block 1 in FIG. 5A is provided for ease of illustration to indicate that the display illustrated in FIG. 6C will remain displayed at 107 until some other action is taken on the part of the operator. The action taken may include continual scrolling in the UP or DOWN direction of the scroll box, input from the keyboard, selection of the ACCEPT option or selection of the ESCape option.

If the system determines at 110 that the operator has keyed in a desired basis protocol, the system will automatically scroll at 111 the list of data names, in this case, the predefined protocol or stored operator defined protocol names appearing in the window. The scrolling in either the up or down direction will continue until the protocol name which most closely matches the protocol name entered by the operator from the keyboard appears in the highlighted or horizontal selection area of the window (see FIG. 6C). Once the protocol name which most closely matches that entered by the operator is located, control is transferred to transition Block 1 in FIG. 5A. As previously mentioned, transition Block 1 is provided for ease of illustration to indicate that the system waits, continuing to display the example illustrated in FIG. 6C, until another action in the form of scrolling the box, inputing data from the keyboard, accepting a selection, or selecting the accept option or selecting the escape option, is taken by the operator.

Based upon a determination at 112 that the operator selected the ACCEPT option, control is transferred to transition Block B. Selection of the ACCEPT option permits the initialization of the creation of an operator defined protocol, as will be described in reference to FIG. 5B, based upon the protocol name, standard or stored operator defined, located within the highlighted or horizontal selection area of the scroll box. Based upon a determination at Block 113 that the operator selected the ESCape option, control is transferred to transition Block A. Operator selection of the ESCape option results in prompting at 104 of the operator to select what he or she desires to do in the protocol training routine, i.e. CREATE, REMOVE or RETRIEVE a protocol. The display illustrated in FIG. 6B will be displayed on screen display 30a and control of the process will continue as previously described. If the ESCape option was not selected, control is transferred to transition Block 1. As previously mentioned, transition Block 1 is provided to illustrate that the system waits, continuing to display the example display illustrated in FIG. 6C, until some affirmative action is taken on the part of the operator such as scrolling the scroll box, entering input at the keyboard, or selecting the accept option.

DETAILED OPERATION: DEFINING PROTOCOL

Figure 5B:
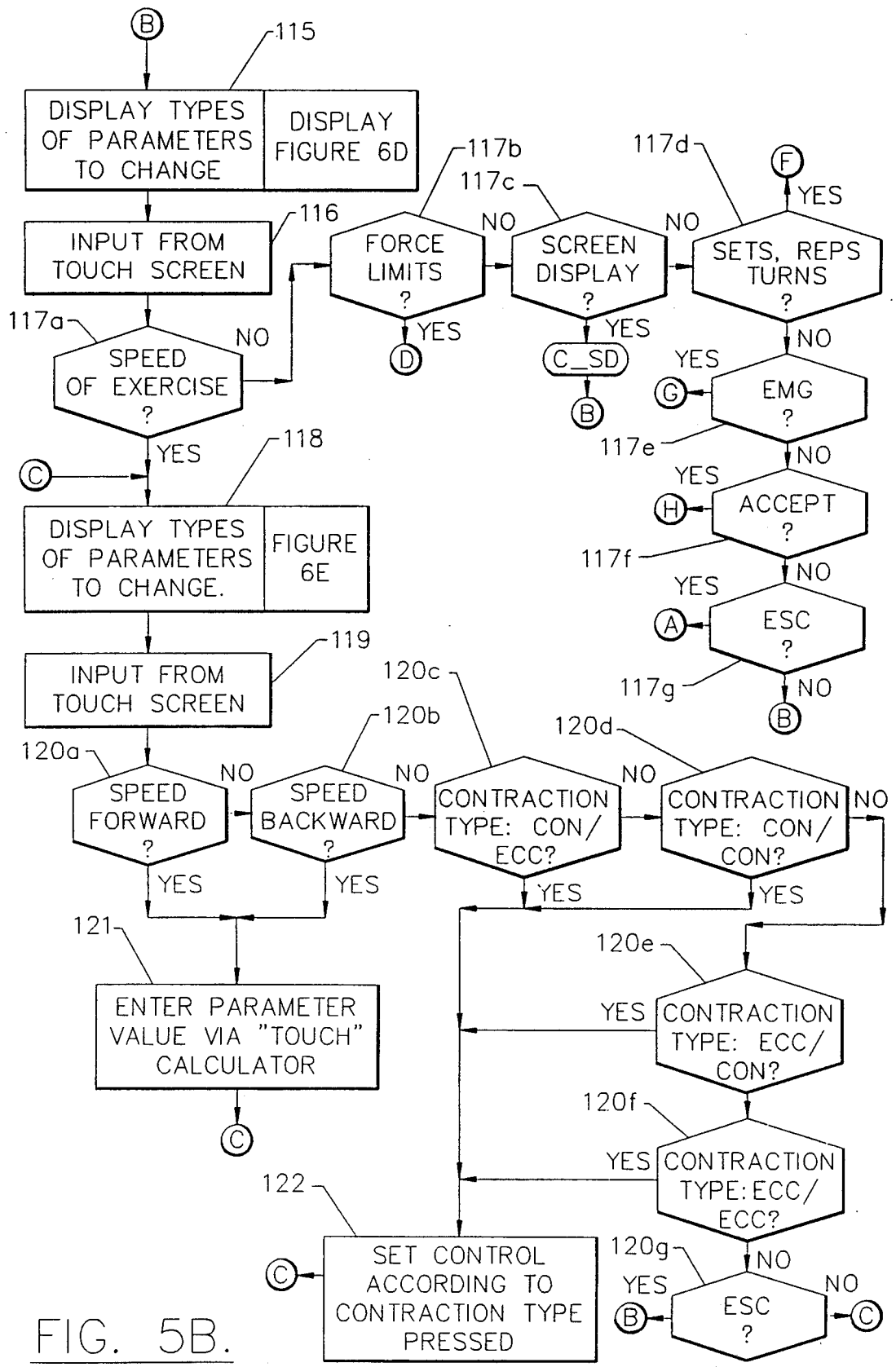
Figure 6D:
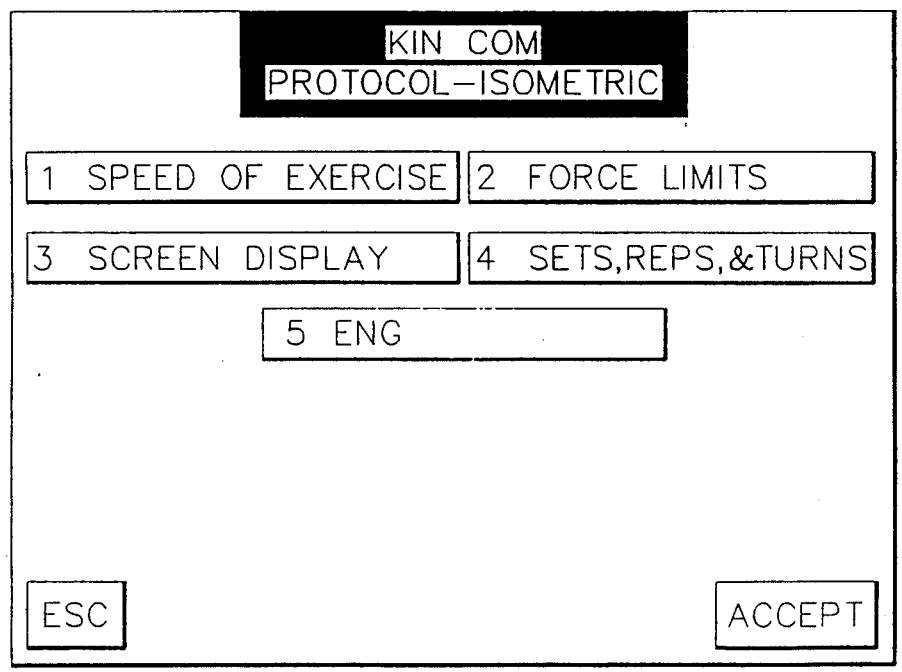

Referring to FIG. 5B, the control flow for defining a protocol following the acceptance of a basis protocol by the operator will now be described. As a result of operator selection of acceptance of a basis protocol at 104 as determined at 106c (See FIG. 5A), the parameters which the operator can change will be displayed at 115. Those parameters which the operator can change include SPEED OF EXERCISE, FORCE LIMITS, SCREEN DISPLAY, SETS, REPS & TURNS, and EMG. A display containing these protocol parameters which appears on display screen 30a is illustrated in FIG. 6D. Consistent with the touch screen interface, the operator can select a parameter by touching the desired parameter to be changed within the blocked area surrounding the displayed parameter. Alternatively, the operator may enter the digit appearing to the left, e.g. 1 or 2, of the displayed parameter. Input of the desired parameter to change is made at 116 by the operator.

A determination is made as to which protocol parameter was selected by the operator to be changed. This determination process is illustrated by multiple decision blocks indicated generally at 117 in FIG. 5B. More specifically, based upon a determination at 117a that the operator selected SPEED OF EXERCISE protocol parameter to be changed, the parameters associated with the SPEED OF EXERCISE protocol parameter are displayed at 118. Based upon a determination at 117b that the operator selected the FORCE LIMITS parameter from the display illustrated in FIG. 6D to be changed, control is transferred to transition Block D. The system continues to make determinations as to which parameter in the display illustrated in FIG. 6D was selected by the operator to be changed.

Based upon a determination at 117c that the operator selected the SCREEN DISPLAY parameter from the parameters displayed in FIG. 6D, control is transferred to transition Block C_SD and then subsequently passed to transition Block B. If the SCREEN DISPLAY option was not selected, a determination is made at 117d whether the operator selected the SETS, REPS & TURNS parameter option. Based upon a determination at 117d that the sets, reps, & turns parameter option was selected by the operator, control is transferred to transition Block F. If the SETS, REPS & TURNS parameter option is determined not to have been selected, a query is made at 117e as to whether the operator selected the EMG parameter option. Based upon a determination at 117e that the EMG parameter option was selected by the operator from the options illustrated in FIG. 6D, control is transferred to transition Block G.

The operator may select the ACCEPT option if none of the parameters are to be changed or if the desired changes have been made to the parameters. Based upon a determination at 117f that the ACCEPT option was selected, control is transferred to transition Block H. Acceptance of the parameters as defined resulting in transfer of control to transition Block H permits finalization of the protocol defining process prior to commencement of the exercise or training routine.

If the ACCEPT option was not selected, a determination is made whether the operator selected the ESCape option. Based upon a conclusion at 117g that the ESCape option was selected, control is transferred to transition Block A. Transition Block A as illustrated in FIG. 5A provides transfer of control permitting the operator to CREATE, REMOVE or RETRIEVE a protocol. This results in the display as illustrated in FIG. 6B. If the ESCape option was not selected, control is transferred to transition Block B provided for purposes of illustration to indicate that the system waits, continuing to display at 115 the screen illustrated in FIG. 6D containing the various protocol parameters which can be modified in setting up an operator defined protocol until one of the parameters is selected.

DETAILED OPERATION: SPEED OF EXERCISE

Figure 6E:
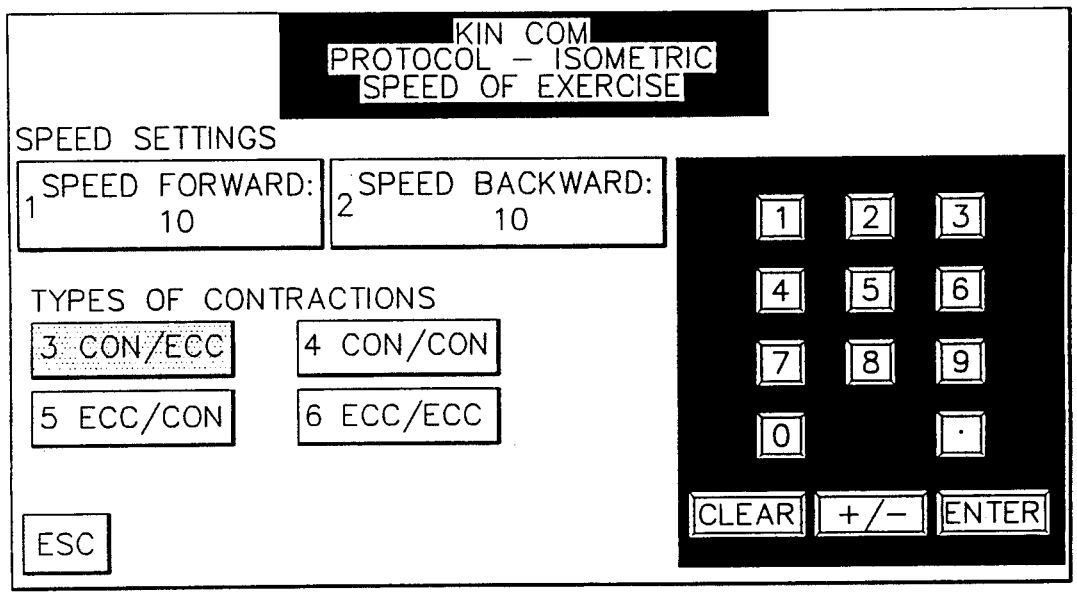

Based upon a determination of 117a in FIG. 5B that the SPEED OF EXERCISE protocol parameter was selected from the parameter options illustrated in FIG. 6D, the types of parameters associated with SPEED OF EXERCISE are displayed at 118. The SPEED OF EXERCISE parameters are illustrated in FIG. 6E which is an example of the display which will appear at 118 on screen display 30a. The operator can then make a selection at 119 of the parameter options displayed in FIG. 6E appearing on screen 30a. Consistent with the touch screen interface, the operator can indicate a selection by touching one of the speed of exercise parameters or by entering one of the digits located to the left of the parameters.

A determination is then made generally at 120 as to which speed of exercise parameter was selected for modification. The determination is made one at a time. Based upon a determination that one was not selected, a determination is made whether the next was selected. This continues until it is concluded that either one of the speed of exercise parameters was selected or none was selected and the escape option was selected.

Based upon a determination at 120a that the SPEED FORWARD parameter was selected to be changed, the operator will enter the desired speed forward at 121 by entering the parameter value via the touch calculator appearing in FIG. 6E. The user may enter the desired values by touching the desired values within the block area surrounding each digit and then pressing the enter touch key. Once the SPEED FORWARD parameter value has been entered via the touch calculator, control is transferred to transition Block C permitting the operator to select another speed of exercise parameter to be changed.

Based upon a determination at 120b that the SPEED BACKWARD option was selected, the operator will enter the SPEED BACKWARD parameter value via the touch calculator at 121. This process of entering the parameter value for the SPEED BACKWARD parameter via the touch calculator is the same as that described with the SPEED FORWARD parameter. Once the value for the SPEED BACKWARD parameter has been entered, control is transferred to transition Block C resulting in display at 118 of the speed parameters illustrated in FIG. 6E permitting the operator to change another speed parameter.

The operator may also select the type of contractions to be performed, including CONCENTRIC/ECCENTRIC, CONCENTRIC/CONCENTRIC, ECCEN- TRIC/CONCENTRIC, and ECCENTRIC/ECCENTRIC from the speed of exercise parameters. A determination is made at decision Blocks 120c, 120d, 120e, or 120f for the CONCENTRIC/ECCENTRIC, CONCENTRIC/CONCENTRIC, ECCENTRIC/CONCENTRIC or ECCENTRIC/ECCENTRIC type of contractions, respectively, as to whether the operator has selected one of these four types of contractions. Based upon a determination that one of these contraction types was selected, control of the exercise is set at 122 according to the contraction type selected. Once control has been set according to the contraction type selected, control is transferred to transition Block C resulting in display at 118 of the speed of exercise parameters illustrated in FIG. 6E permitting the operator to make further changes to speed associated parameters.

The final option which the operator may select is the ESCape option. If the ESCape option as well as none of the other options were selected, control is transferred to transition Block C. This transfer of control to transition Block C based upon the determination at 120g that ESCape option was selected, is provided for illustration purposes to indicate that the system will wait, continuing to display the screen display illustrated in FIG. 6E at 118 until a selection is made. Based upon a determination at 120g that the ESCape option was selected, control is transferred to transition Block B. Transfer of control to transition Block B results in display at 115 of the protocol parameters which can be modified by the operator as illustrated in FIG. 6D. The process of operator selection of protocol parameters to be changed and changing of those parameters continues until all the desired parameters changes have been made and the operator selects the ESCape option. Control is then transferred to transition Block A resulting in display at 104 of the CREATE, REMOVE or RETRIEVE protocols as illustrated in FIG. 6B.

DETAILED OPERATION: FORCE LIMITS

Figure 5C:
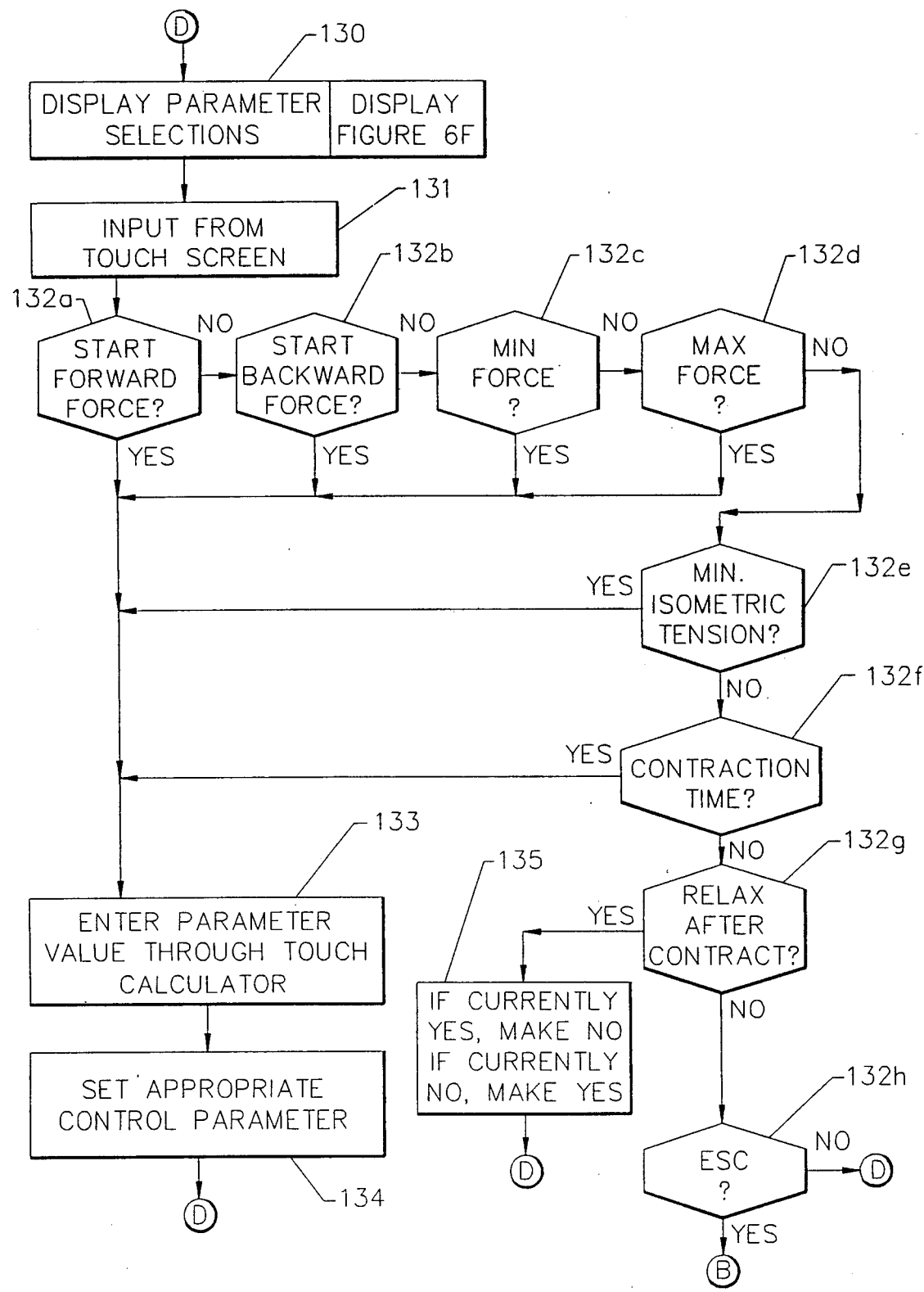
Figure 6F:
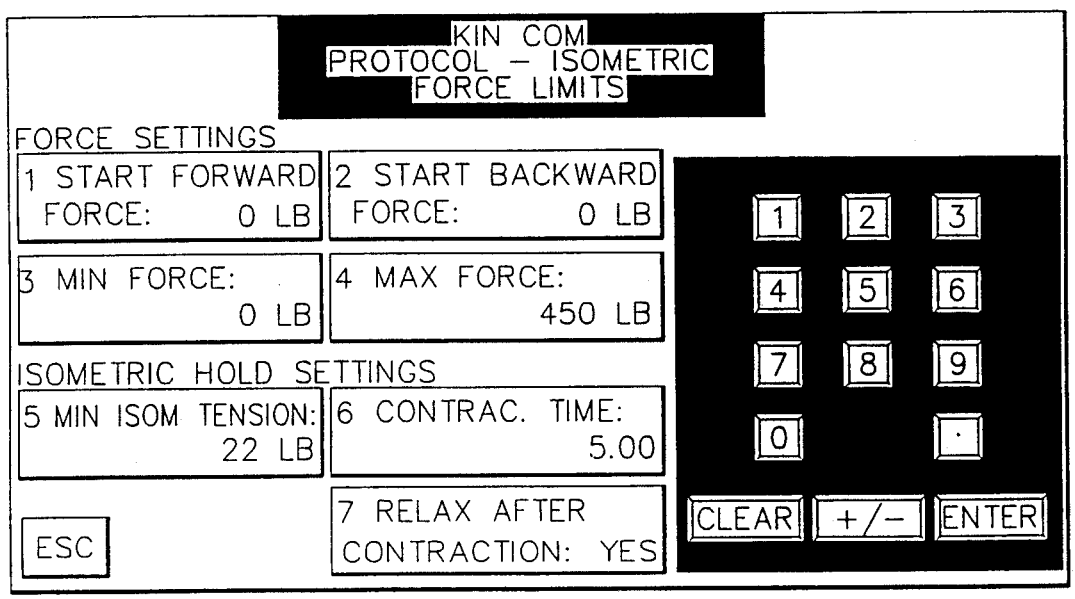

Referring to FIG. 5C, details of the processing of modification of the force limits parameters will now be described. Based upon a determination at 117b that the operator selected the FORCE LIMIT parameters to be changed in defining a new operator defined protocol, control was transferred to transition Block D resulting in display of the force limit parameters at 130. The force limit parameters which can be changed by the operator include force settings, i.e. START FORWARD FORCE, START BACKWARD FORCE, MINIMUM FORCE and MAXIMUM FORCE, and pause settings, i.e. MINIMUM ISOMETRIC TENSION and CONTRACTION TIME. These force limit parameters as displayed at 130 appear on the display 30a of monitor 30 as illustrated in FIG. 6F. The operator may then select at 131 from the options by touching the screen at the option desired within the blocked area surrounding the desired option. Alternatively, the operator may select the desired option by entering the appropriate digit appearing to the left of each option on the keyboard and pressing the return or enter key on the keyboard.

The system proceeds to determine which of the force limit parameters was selected to be changed by the operator. Each parameter is checked one at a time to see which parameter was selected. If one parameter was not selected, the system proceeds to check if the next in line was selected. This process of verifying which parameter was selected continues either until it is determined which parameter was selected or it is determined that the ESCape option was selected. Control flow of this determination process is illustrated by multiple decision blocks at 132a through 132g in regards to START FORWARD FORCE, START BACKWARD FORCE, MINIMUM FORCE, MAXIMUM FORCE, MINIMUM ISOMETRIC TENSION, CONTRACTION TIME, and RELAX AFTER CONTRACTION.

The value for each force limit parameter is in newtons. Based upon a determination at one of multiple decision Blocks 132a through 132f that one of the force limit parameters was selected, the operator enters the parameter value for that particular selected parameter via the touch calculator at 133. The touch calculator appears in FIG. 6F and is utilized as previously described in reference to other figures. The operator will enter the value for each force limit parameter he or she has selected and then press the enter button located on the touch calculator. The computer controller then sets the appropriate force limit control parameter at 134 with the new value entered by the operator for the particular control parameter resulting in control of the muscle exercise machine in accordance with the values for the particular parameters which have been previously defined or operator defined via this force limit parameter selection.

Once the system has set the appropriate force limit control parameter in accordance to the entered value, control is transferred to transition Block D to indicate that the operator may then make another selection as to which parameter he or she desires to change. The operator then can select another force limit parameter to be changed by making the appropriate indication on the touch screen or, in the alternative, at the keyboard.

Based upon a conclusion at 132a through 132f that none of the force limit parameters were selected to have the units changed, a determination is made at 132g whether the RELAX AFTER CONTRACTION option was selected. RELAX AFTER CONTRACTION is a toggle or flip-flop parameter whereby a value of "yes" is changed to "no" or a value of "no" is changed to "yes" at 135. This results in the display showing the new VALUE AFTER CONTRACTION parameter as indicated by transfer of control to transition Block D.

As indicated at decision Block 132h, entry of the ESCape option results in transfer of control to transition Block B which causes the system to display at 115 the protocol parameters which the operator may change as illustrated in FIG. 6D. Processing would then continue with selection of the protocol parameters to be changed by the operator as previously described. In the event none of the force limit parameters are selected to be changed and the ESCape option also is not selected, control is transferred to transition Block D. Transition Block D is provided in this instance to indicate that the system waits, continuing to display at 130 the force limit parameters on display screen 30a as illustrated in FIG. 6F, until an appropriate selection is made by the operator.

The operator created protocol can be stored in memory for future use. The operator stores the protocol by entering a desired protocol name via the keyboard. The system then stores the protocol as identified by the entered name. The selected protocol name is then also placed in an appropriate position within the list of protocol names, a portion of which appear in the window on display 30a when the operator makes a protocol selection.

DETAILED OPERATION: SCREEN DISPLAY

Figure 5D:
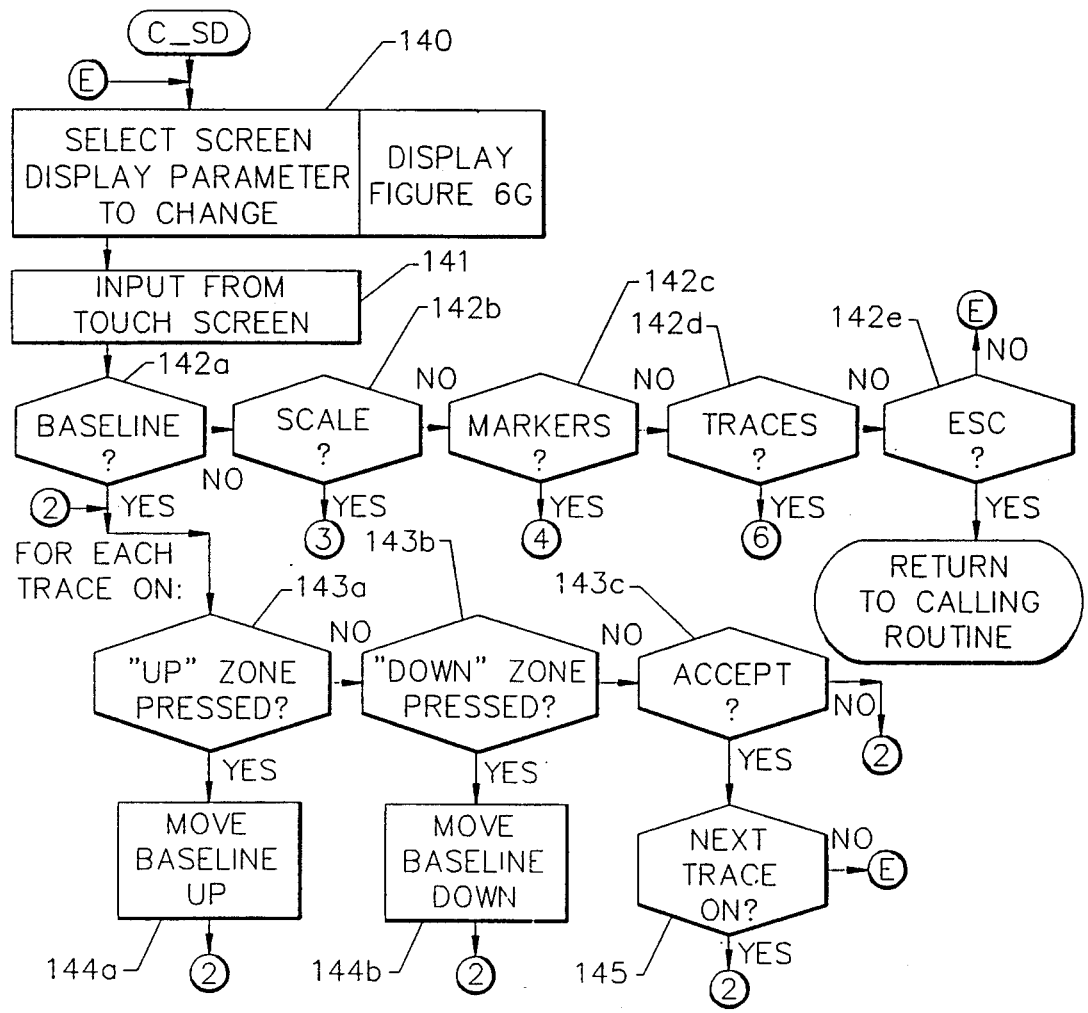
Figure 6G:
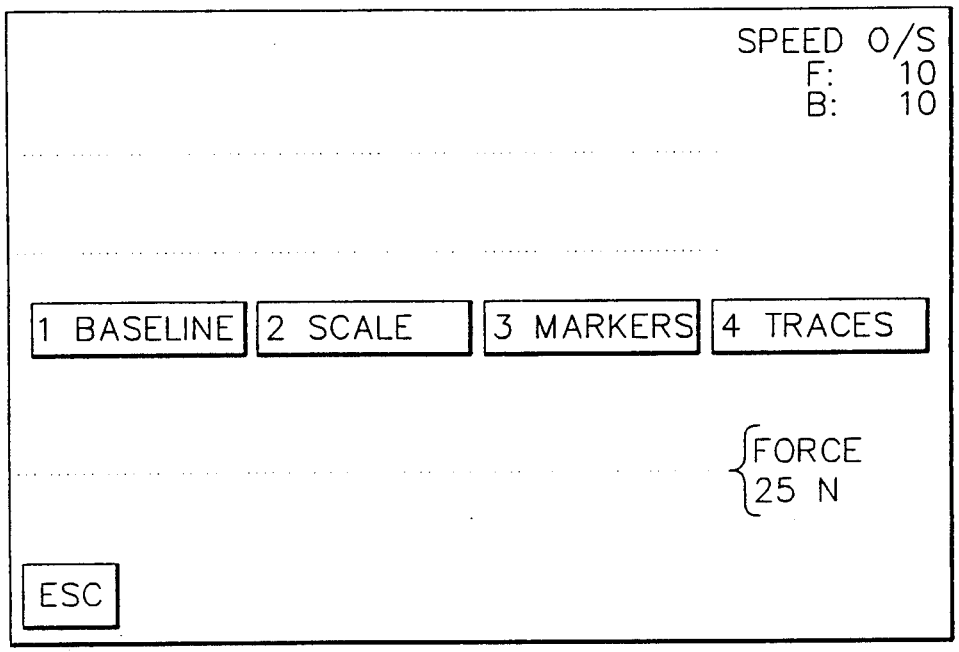

Referring to FIG. 5D, the control flow in modifying the screen display parameters will now be described. Based on a determination at 117c that the operator selected the SCREEN DISPLAY parameters to be changed, control was transferred to transition Block C_SD. This determination results in display of the screen display parameters at 140 in FIG. 5D. The screen display parameters which the operator can change include the BASE LINE, SCALE, MARKERS, and TRACERS parameters. The parameters displayed at 140 are displayed on display 30a as illustrated in FIG. 6G. The operator then selects the screen display parameter to be changed at Block 141 by touching the appropriate parameter on the touch screen or entering the digit to the left of the appropriate parameter at the keyboard.

Figure 6H:
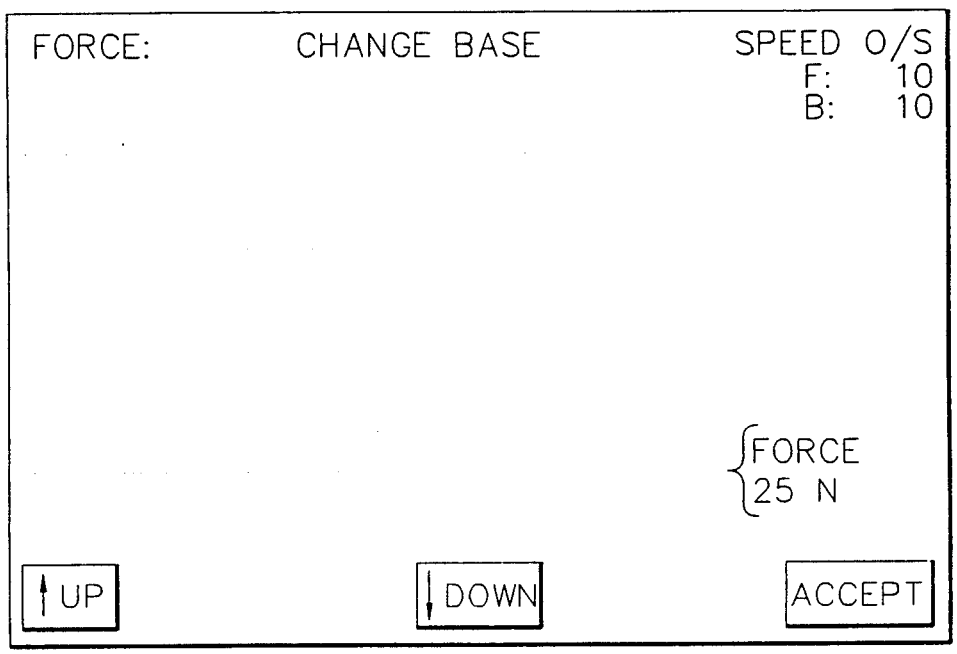

A determination is made as to which screen display parameter the operator selected for change. As before, a determination is made by the system one parameter at a time and continues until either a parameter is found to have been selected or it is determined that the operator selected the ESCape option. This one at a time process is illustrated in the multiple decision blocks in FIG. 5D generally at 142. Based upon a determination at 142a that the BASE LINE parameter was selected, the operator may then either increase or decrease the base line parameter for each trace which is on, by touching the appropriate UP or DOWN prompts on the touch screen. The display appearing on display 30a as a result of the determination at 142 is illustrated in FIG. 6H.

A determination is made at 143a whether the operator pressed the UP zone. Based upon a determination of 143a that the operator selected UP, the base line is moved up in a vertical direction from its present position at 144a. However, based upon a determination at 143b that the operator desires to move the base line of the screen display vertically downward from its present location, the base line is moved vertically downward at 144b from its present location. Whether the base line is moved upward or downward at 144a or 144b, control is transferred to transition Block 2 permitting the operator to further move the base line either upward or downward or accept the present location of the base line. This is indicated by transfer of control from Blocks 144a and 144b to transition Block 2 which results in the system waiting until either the UP or DOWN options or the ACCEPT option is selected by the operator.

Based upon a determination at 143c that the operator selected the ACCEPT option, a determination is made at 145 whether the next trace is "on". If it is determined at 145 that the next trace is "on", control is transferred to transition Block 2. In other words, the system waits until the operator modifies the base line in the UP or DOWN direction for the next trace or selects the ACCEPT option. If it is determined at 145 that the next trace is not "on", control is transferred to transition Block E provided for purposes of illustration to indicate that the screen display parameters are displayed at 140 as illustrated in FIG. 6G. Processing of operator selection of screen display parameters to be changed will continue with scale, markers, and tracers parameters.

Traces which may be "on" for any given test include angle, velocity, force, EMG1 and EMG2. By default, one trace will be "on". The trace which is "on" by default depends on the selected protocol. The decision at 145 whether the next trace is "on" determines whether a trace other than the default trace is on. If no traces are "on", i.e. the operator turned all traces "off", the display parameters will continue to be displayed at 140 until one or more traces are turned "on".

Figure 5E:
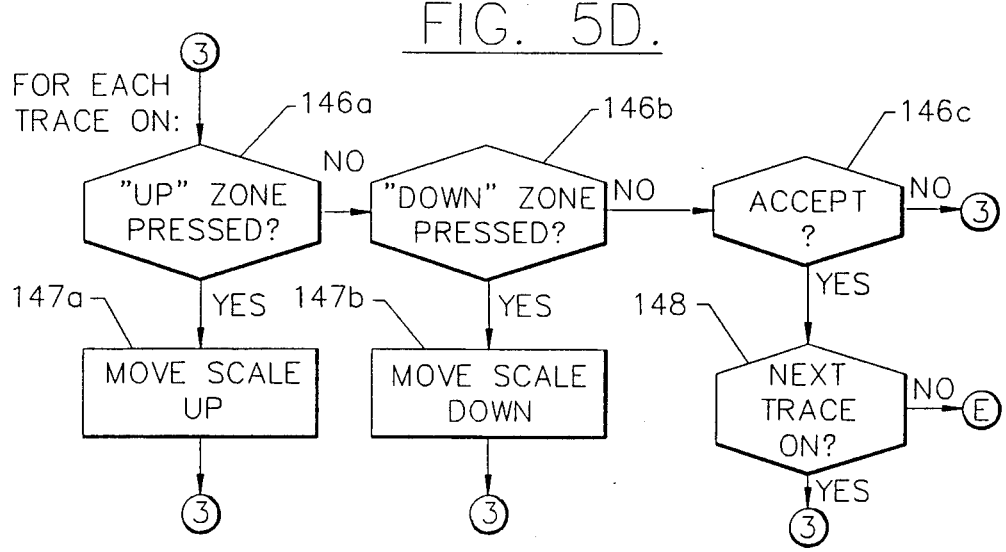
Figure 6I:
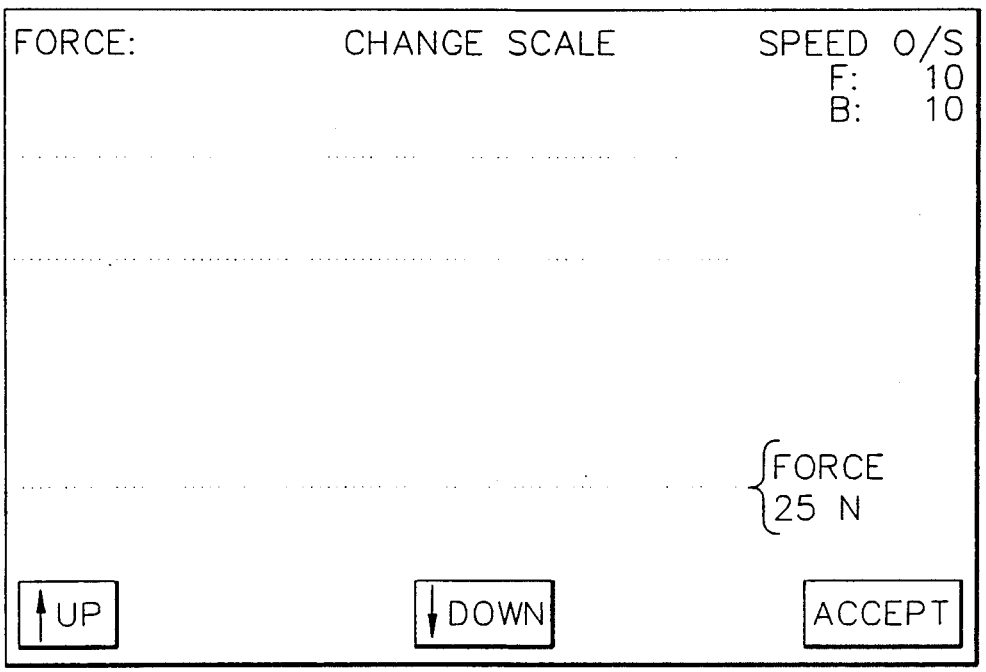

Based upon a determination at 142b that the operator selected the SCALE screen display parameter at 141, control is transferred to transition Block 3 resulting in display of the display screen illustrated in FIG. 6I. FIG. 6I illustrates the display which permits the operator to change the scale of the screen display for each trace which is "on". The scale of the screen display is displayed in newtons or pounds for force, degrees for angle, degrees per second for velocity and millivolts for EMG1 and EMG2. The operator can either increase or decrease the scale for each trace by respectively pressing the UP or DOWN touch screen keys. Referring to FIG. 5E, based upon a determination at 146a that the operator pressed the UP key, the scale in terms of newtons is increased at 147a, i.e. moved up, to increase the scale size. A higher scale will be desired when higher amounts of force are produced in order to display the variations of the force.

Based upon a determination at 146b that the DOWN key on the change scale display illustrated in FIG. 6I was pressed, the scale in terms of newtons will be decreased at 147b, i.e. moved down. The smaller scale can be utilized when smaller amounts of force are produced. Whether the scale was moved up or down, control is transferred to transition Block 3 provided for illustration to indicate that the system waits until further selections in terms of moving the scale up or down or acceptance of the scale are made by the operator.

Based upon a determination at 146c that the operator selected the ACCEPT option by pressing the ACCEPT key or zone on the display as illustrated in FIG. 6I, a determination is made at 148 as to whether the next trace is "on". If the next trace is "on", control is then returned to transition Block 3 in order to permit changing the scale parameter of the next trace of the screen display by the operator in terms of moving the scale up or down or accepting the scale in its current state. Based upon a determination at 148 that the next trace is not "on", control is transferred to transition Block E resulting in display of the screen display parameters at 140 as illustrated in FIG. 6G. This permits the operator to enter via either the touch screen or the keyboard another screen display parameter which he or she desires to modify. As with many of the screens and options previously described, if neither the UP key nor the DOWN key is pressed nor the ACCEPT option selected, the system waits continuing to display the scale parameter screen as illustrated in FIG. 6I until the operator takes an affirmative action in terms of moving the scale up or down or accepting the present value of the scale parameter.

Figure 6J:
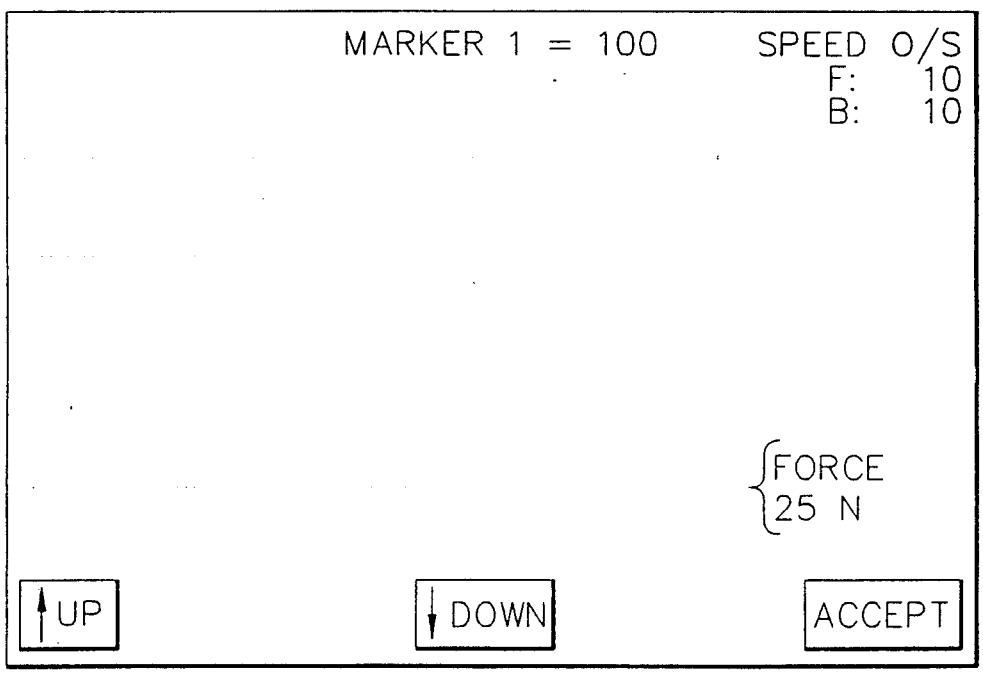

Based upon a determination at 142c that the operator selected the MARKERS parameter from the screen display parameters displayed at 140, control is transferred to transition Block 4 resulting in display of the marker screen which is illustrated in FIG. 6J. As with the base line and scale parameter modifications and screens, the operator has the option of increasing or decreasing the marker by pressing the UP or DOWN touch key located at the base of the screen illustrated in FIG. 6J. The markers are horizontal feedback markers which can be increased or decreased on a scale of force units such as newtons or pounds or velocity units of degrees per second depending on the selected protocol.

Figure 5F:
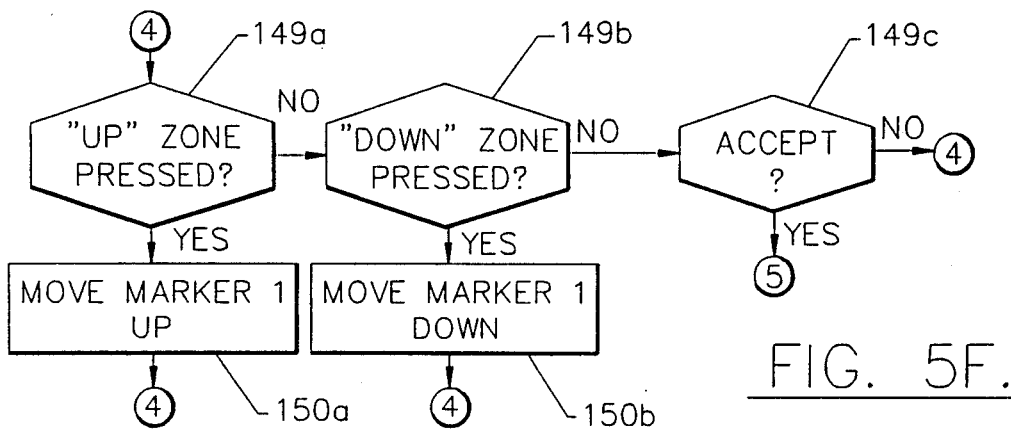

Referring to FIG. 5F, based upon a determination at 149a that operator indicated a desire to move the marker up, i.e. increase the marker, indicated by pressing the UP touch key, the marker is moved up at 150a. Based upon a determination at 149b that the operator desires to decrease the marker and made such an indication by pressing the DOWN touch key or zone, the marker is moved down or increased at 150b. Whether the marker has been increased or decreased, i.e. moved up or down, at 150a or 150b, respectively, control is transferred to transition Block 4 provided for illustration to indicate that the marker parameter will retain its current value until the operator either further increases or decreases the marker or accepts the marker at its present value.

Based upon a determination at 149c that the operator desired to ACCEPT the marker at its present value by indication on the touch screen, control is transferred to transition Block 5 to permit modification of the other horizontal markers by the operator. If the ACCEPT selection has not been made and the UP and DOWN zones have not been pressed, the marker parameter will maintain its present value and remain unchanged until some positive action is taken on the part of the operator. This is indicated by transition Block 4 in FIG. 5D.

Figure 5G:
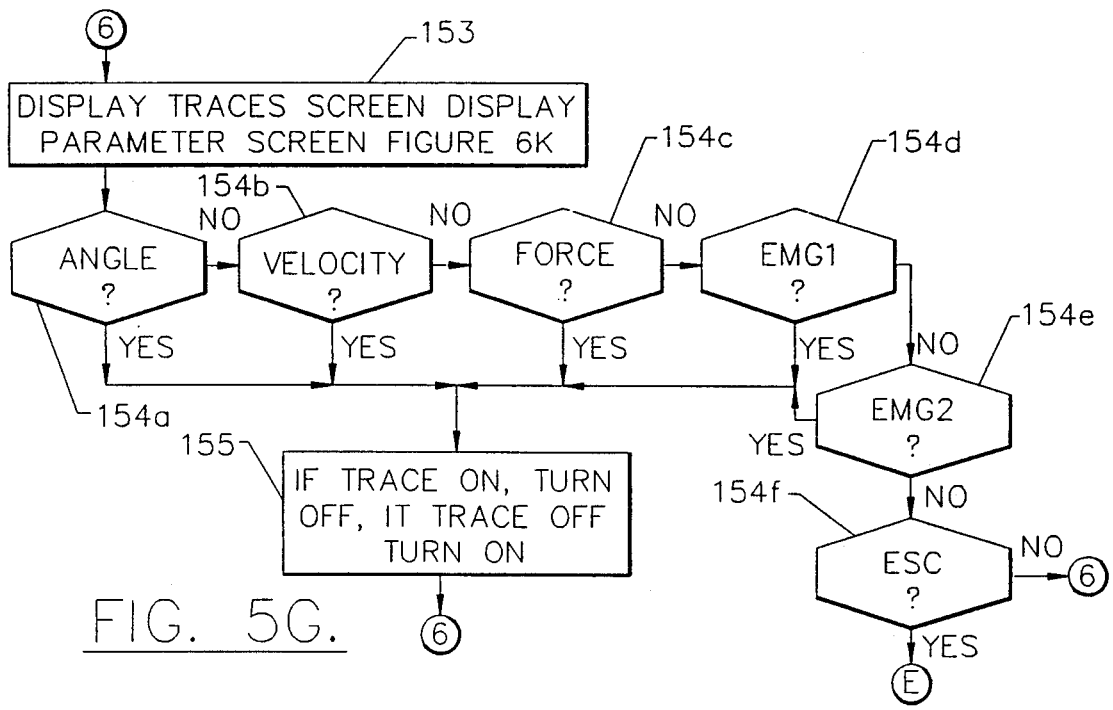
Figure 5H:
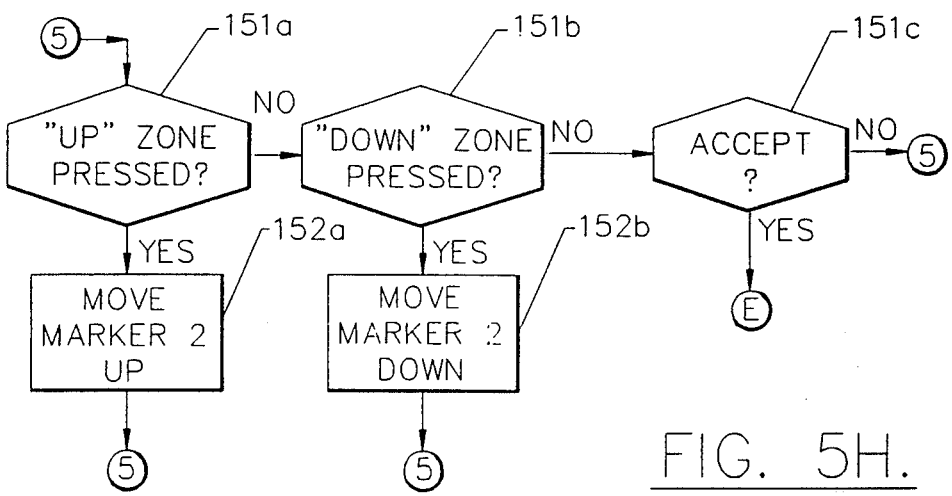

Referring to FIG. 5H, processing of the marker parameter continues at transition Block 5 in order to permit modification of the subsequent horizontal markers. A screen similar to FIG. 6J is displayed with the identification at the top indicating marker 2 and its value or any subsequent marker and its corresponding value. As with FIG. 5D and description of the modification of the marker, based upon a determination at 151a that the operator desires to increase marker 2 and indicates such a desire by pressing the UP zone or touch key, the marker presently being changed is moved up at 152a. Based upon a determination at 151b that the operator desires to decrease the marker presently being changed and makes an indication of such desire by pressing the DOWN touch key or zone on the touch screen, the marker is decreased or moved down at 152b in terms of newtons of force.

The marker will maintain its present value until the operator either makes another indication to move the marker UP or DOWN or selects the ACCEPT option. Based upon a determination at 151c that the ACCEPT option was selected, control is transferred to transition Block E resulting in display at 140 of the screen display parameters permitting the operator to change any of those screen display parameters including those which have already been modified. The modification of the markers will continue until all markers have been modified and accepted or accepted, without modification, at which time, control will be transferred to transition Block E resulting in display at 140 of the screen display parameters which are illustrated in FIG. 6G.

Figures 6K, 6L:
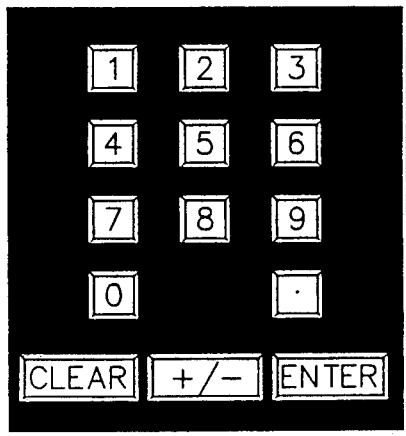
Figure 6:
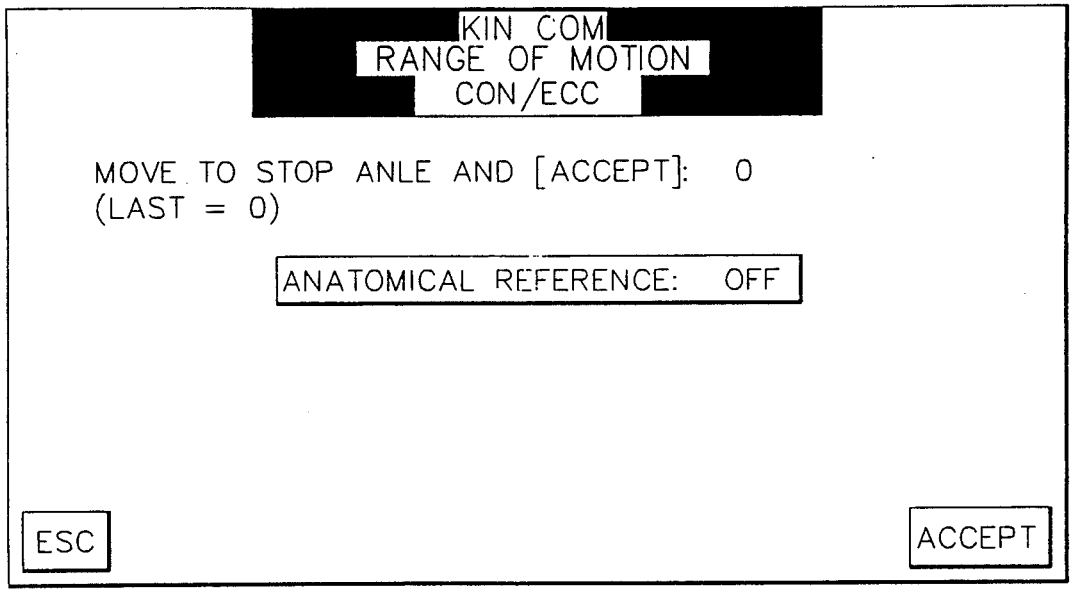

Based upon a determination at 142d that the operator selected the TRACES parameter from the screen display parameters displayed at 140, control is transferred to transition Block 6. Referring to FIG. 5G, transition Block 6 is expanded to indicate the flow of the modification of the tracers screen display parameter displayed at 153. The trace parameters which the operator can change include ANGLE, VELOCITY, FORCE, EMG1 and EMG2 as illustrated in FIG. 6K. The values for any of these parameters associated with the trace parameter are limited to "on" or "off". Thus, selection by the operator to change any of these trace parameters results in a flip-flop or toggle of the on-off value, from "on" to "off" or from "off" to "on".

A determination is made as to which trace parameter was selected for change. The determination process is illustrated by multiple decision blocks indicated at 154. If it is determined that the operator has determined that he or she desires to change a particular parameter's value, the particular parameter value will be toggled or flip-flopped from "on" to "off" or from "off" to "on" for providing a trace based on ANGLE, VELOCITY, FORCE, EMG1 or EMG2. This toggling occurs at 155. If none of the parameters were selected for change by the operator, i.e. the system has determined that the angle has not been selected at 154a, velocity has not been selected at 154b, force has not been selected at 154c and EMG1 or EMG2 have not been selected at 154d or 154e, respectively, a determination will be made whether the ESCape option was selected by the operator. Based upon a determination at 154f that the ESCape option was selected, control is transferred to transition Block E resulting in display of the display parameters at 140 which the operator can change. These parameters which the operator can change are illustrated in FIG. 6G. If the ESCape option was not selected and no other options of the ANGLE, VELOCITY, FORCE, or EMG(s) parameter traces were selected, control is transferred to transition Block 6 resulting in continued display at 153 of the display parameter traces as illustrated in FIG. 6K which can be turned "on" or "off".

DETAILED OPERATION: SETS, REPS & TURNS

Figure 5I:
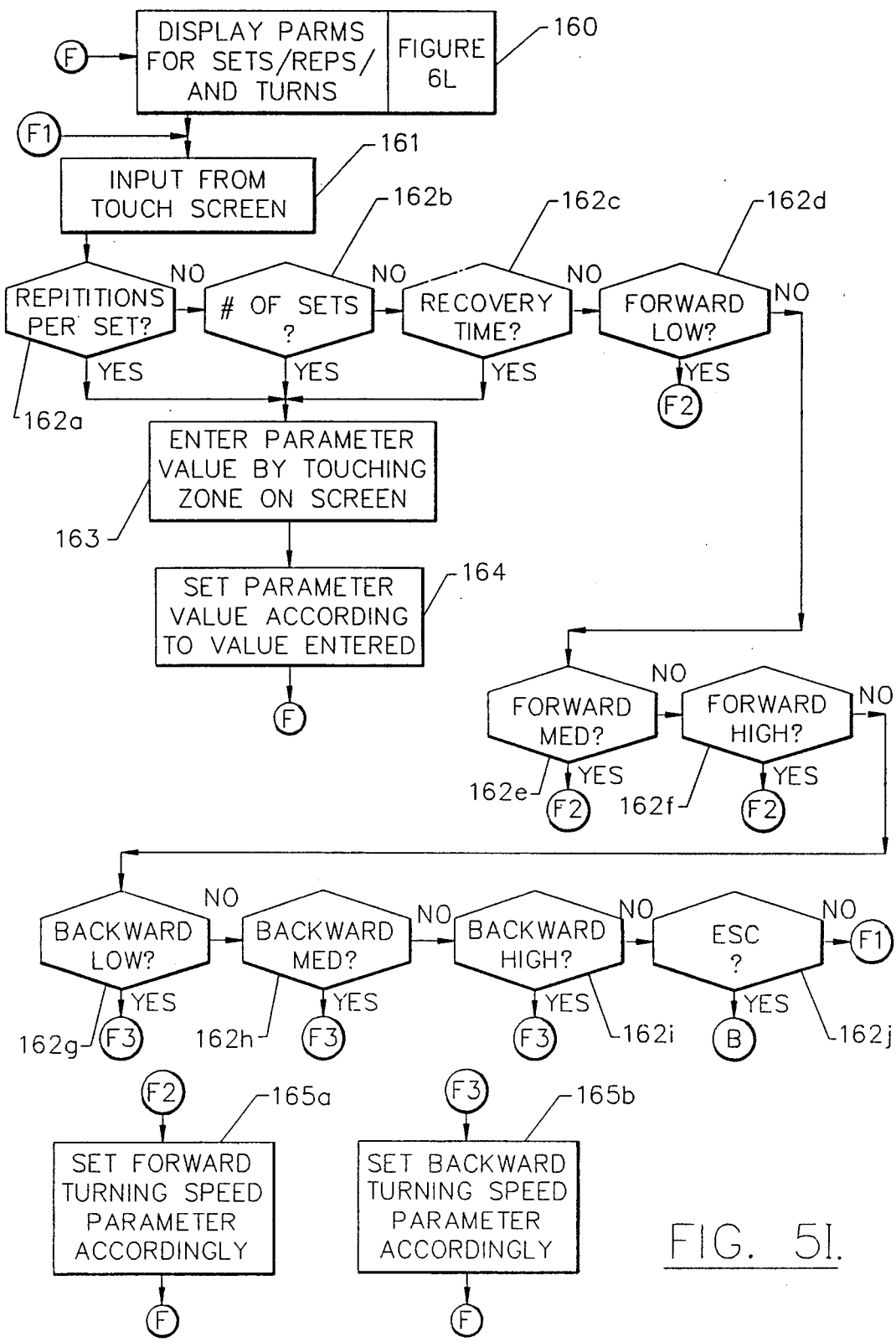

Referring to FIG. 5I, control of the processing as a result of an operator indication of a desire to change the SETS, REPS, & TURNS parameters for the operator defined protocol being created will now be described. As a result of determination at 117d of FIG. 5B that the operator desires to change the SETS, REPS & TURNS parameters, the SETS, REPS & TURNS parameters and values are displayed at 160. The operator is permitted to set values for the REPETITIONS PER SET, NUMBER OF SETS, and RECOVERY TIME via a touch calculator. Additionally, the operator can change the TURNING POINTS, both FORWARD and BACKWARD, to be set to either LOW, MEDIUM, or HIGH. An example of the display containing these parameters and values as well as the touch calculator is illustrated in FIG. 6L.

The REPETITIONS PER SET, NUMBER OF SETS and RECOVERY TIME are set via the touch calculator. The setting of these values is accomplished by touching the parameter whose value is to be changed, entering the new value on a touch key calculator and pressing the ENTER key or box. After the enter key or box is pressed, the operator then can select another parameter to be changed or in the alternative can change the FORWARD or BACKWARD TURNING POINTS. The FORWARD or BACKWARD TURNING POINTS can changed by pressing the desired touch screen key on the display or by entering the digit to the left of the desired range on the keyboard.

Once the operator makes a selection of the desired parameter at 161, a determination is made as to which parameter has been entered. Since the user activity is the same whether the REPETITIONS PER SET, NUMBER OF SETS, or RECOVERY TIME parameters was selected, these three parameters will be discussed together. Based upon a determination at 162a to change the value of the REPETITIONS PER SET parameter, at 162b to change the NUMBER OF SETS parameter, or at 162c to change the RECOVERY TIME parameter, the new value for the parameter selected is entered at 163 by touching the touch calculator on the screen as illustrated in FIG. 5L. Alternatively, the new parameter value can be entered via the keyboard. Once the new parameter value has been entered by the operator via the touch calculator or the keyboard, the parameter selected for change, i.e. REPETITIONS PER SET, NUMBER OF SETS, or RECOVERY TIME, is set at 164 according to the value entered by the operator. Once the parameter selected has been set to the new parameter value, control is transferred to transition Block F which results in continued display at 160 of the SETS, REPS, AND TURNS parameters. In other words, the operator is then permitted to select another parameter within the SETS, REPS, AND TURNS option to be modified.

Control proceeds in processing of the SETS, REPS AND TURNS option similar to the processing with the other options in that multiple decision blocks are processed. If the REPETITIONS PER SET, NUMBER OF SETS, and RECOVERY TIME parameters, in that order, were not selected by the operator, a determination is made as to whether the TURNING POINTS FORWARD parameter has been selected to be modified by the operator via an indication of LOW, MEDIUM or HIGH turning point in the forward direction. A determination is first made at 162d whether the FORWARD LOW value was selected. If FORWARD LOW was not selected, a determination is made at 162e whether FORWARD MEDIUM was selected. Finally, if FORWARD MEDIUM was not selected, a determination is made at 162f whether FORWARD HIGH was selected. If the operator made an indication to change either the FORWARD LOW, FORWARD MEDIUM, or FORWARD HIGH value for the turning point forward parameter, the value for the forward turning speed, i.e. initial acceleration of the lever arm out of a turning point, is set at 165a according to the value of the parameters indicated, i.e. LOW, MEDIUM, or HIGH.

If the operator did not make an indication to change the forward turning speed parameter, a determination is then made in sequential order as to whether the operator has made an indication to change the backward turning point parameter. A determination is first made at 162g whether the operator selected the backward turning speed parameter to be set to LOW. If a value of low was not selected by the operator, a determination is made at 162h whether an indication was made to set the backward turning speed parameter to MEDIUM. Finally, if no indication was made to set the backward turning speed parameter to MEDIUM, a determination is made at 162i whether the operator made an indication to set the backward turning speed equal to HIGH. Regardless of which value the operator desired the backward turning speed parameter be set to, the backward turning speed parameter is set at 165b according to the new value selected or indicated on the touch screen or entered on the keyboard by the operator to indicate the deceleration going into a turning point.

Finally, if none of the parameters were selected by the operator to be modified, a determination is made at 162j whether the operator selected the ESCape option. Based upon a determination at 162j that the ESCape option was selected, control is transferred to transition Block B resulting in the display at 115 of the protocol parameters, e.g. speed of exercise or force limits, as illustrated in FIG. 6D permitting the operator to change parameter values in defining an operator defined protocol. If the ESCape option was not selected, control is transferred to transition Block F1 to indicate that the system waits, continuing to display the display illustrated in FIG. 6L, until a positive action is taken on the part of the operator to either change one of the values of the parameters displayed in FIG. 6L or to accept the parameters as indicated by selecting the ESCape option to return to the main changeable parameters display at 115 which is illustrated in FIG. 6D.

DETAILED OPERATION: SAVING PROTOCOLS AND BEGINNING EXERCISE

Figure 5J:
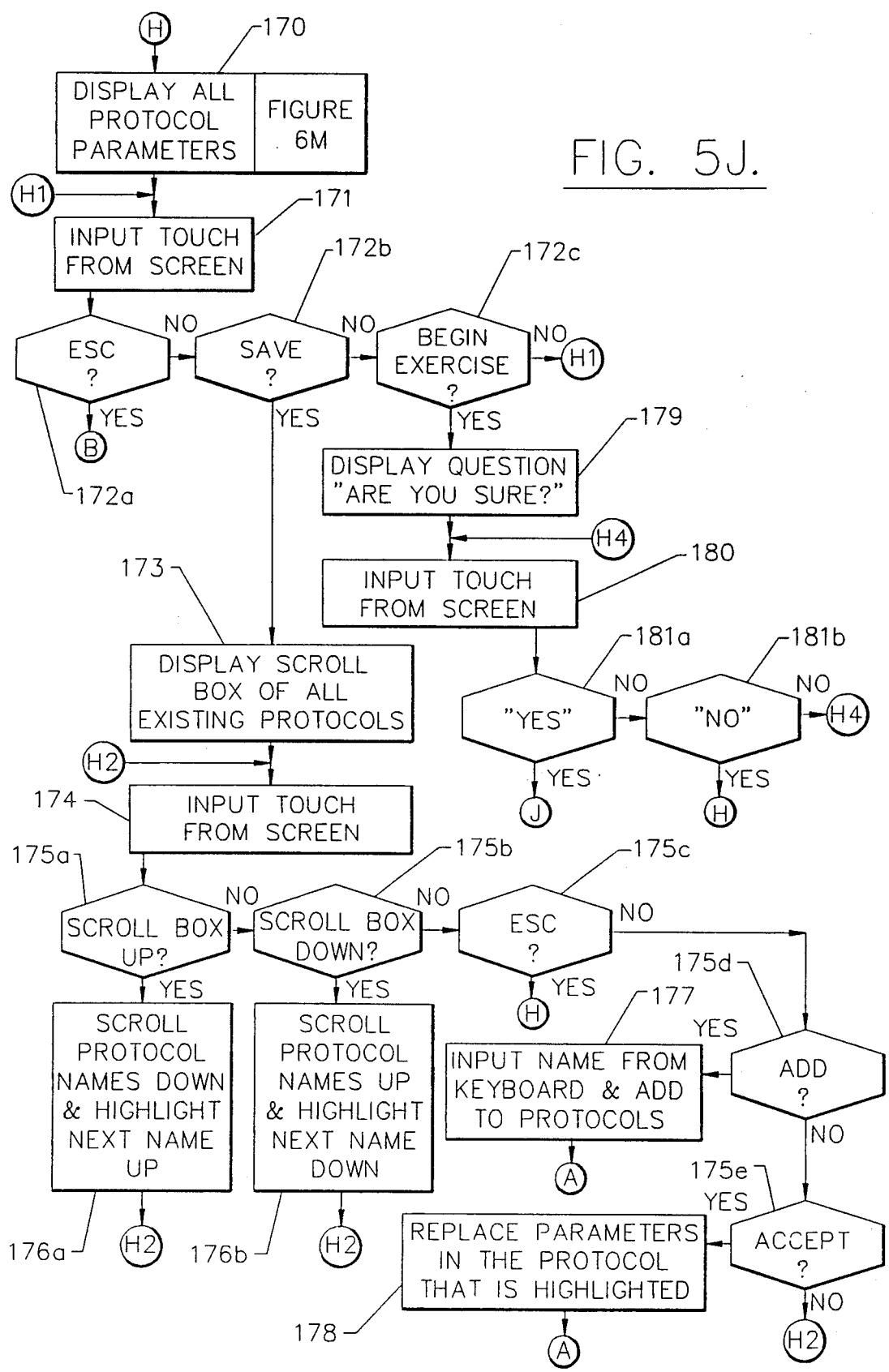
Figure 5L:
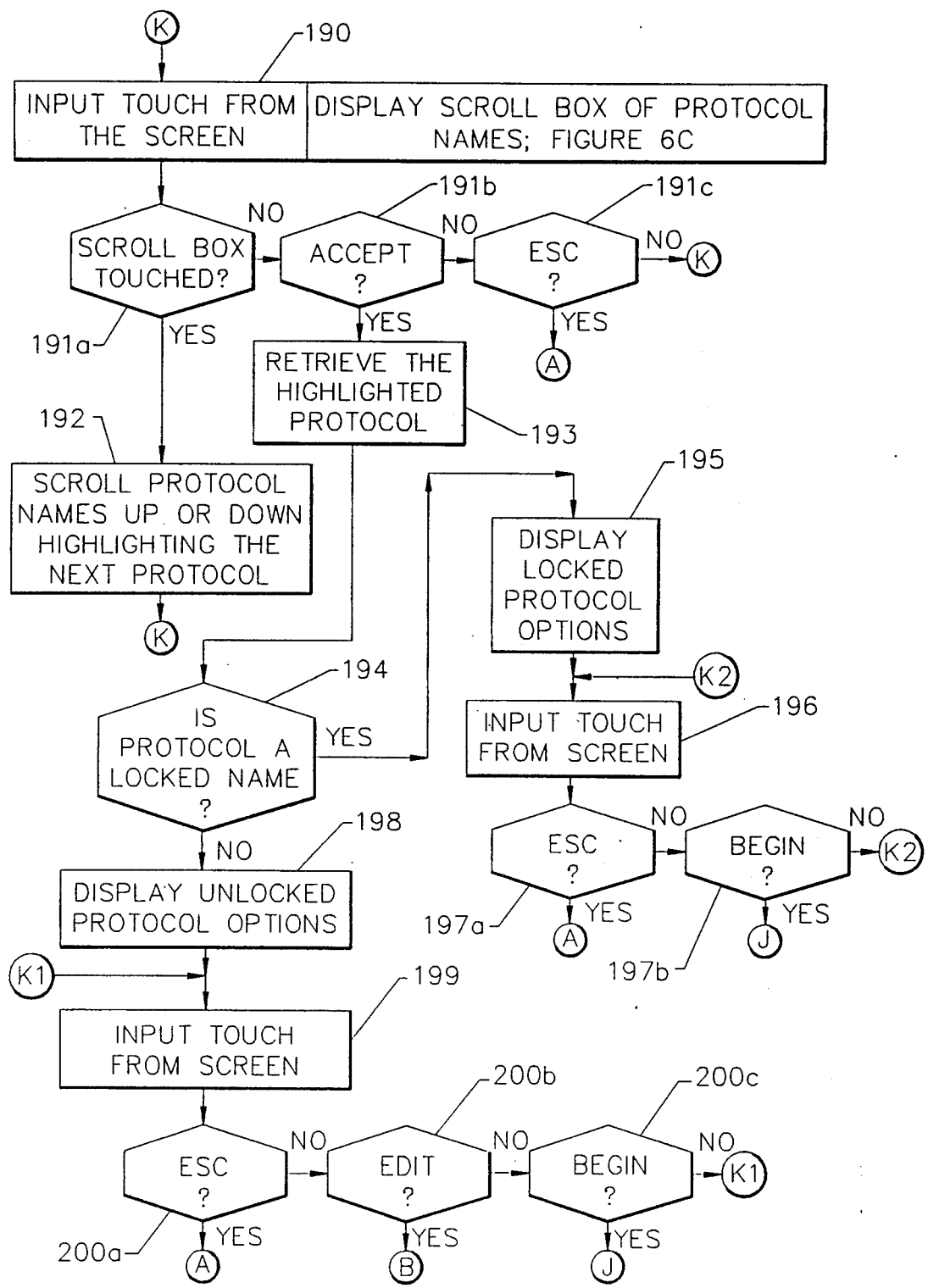

Referring to FIG. 5J, the control flow of the process resulting from a determination at 117f in FIG. 5B that the operator indicated an acceptance of the parameters as currently defined will now be described. Once the operator has indicated acceptance of the parameters as currently valued, all the parameters and the values for the protocol defined by the operator are displayed at 170. One example of the display containing the protocol parameters and values defined by an operator is illustrated in FIG. 6M. This display summarizes the exercise which the operator has designed. The operator is given the option of saving the exercise so that this particular operator defined protocol can be retained for future use. In the event this operator defined protocol is saved, it can be retrieved at any future time by selecting it in the protocol selection process (see FIG. 6C). Alternatively, once saved, any operator defined or predefined protocol can be removed from memory during the protocol selection process (see FIG. 6C). In the event that one of the protocols already resident in memory, i.e. predefined or stored operator defined protocols, is selected, the summary of the protocol parameters and values for that particular protocol, an example of which is illustrated in FIG. 6M, is displayed at 170 on screen display 30a.

The operator selects at 171 one of the three options appearing on the display in FIG. 6M, i.e. ESCape, SAVE, or BEGIN EXERCISE via the touch screen. A determination is made as to which option was selected generally indicated at 172. Based upon a determination at 172a that the ESCape option was selected, control is transferred to transition Block B resulting in display of the protocol parameters (e.g. speed of exercise or force limits) at 115, permitting the operator to further change the parameters in the operator defined protocol. These parameters have been previously discussed with reference to FIG. 5B and the display containing the parameters illustrated in FIG. 6D. The selection of the ESCape option permits the operator to make further changes to an operator defined protocol whether it has been previously stored in memory or defined during this present session as well as permits the operator to make modifications to the predefined protocols even if already changed.

Based upon a determination at 172b that the SAVE option was selected, the scroll box containing a portion of the list of existing protocol names is displayed at 173. Selection of the SAVE option indicates that the protocol as presently defined and presently appearing on the display is to be saved. The scroll box containing a partial list of the protocol names is displayed in a screen display similar to that illustrated in FIG. 6C. The operator can scroll up and down the list of protocol names appearing in the window or scroll box. This scrolling is performed as previously described. The operator can scroll up the list to view those protocol names appearing in alphabetical order before those presently in the viewing window by touching the UP area of the scroll box. Similarly, the operator can view those names listed in alphabetical order which follow those presently in the viewing window by pressing the DOWN portion of the scroll box on the touch screen (Block 174).

Based upon determination at 175a that the operator selected at 174 the UP portion of the scroll box, the names listed in the window portion of the scroll box will move down resulting in the previous name appearing in the highlighted or horizontal selection area 176a. Similarly, based upon a determination at 175b that the operator indicated a desire to scroll DOWN the list of protocol names appearing in the window or scroll box, the list of names in the window portion would move up in a vertical direction resulting in the succeeding name appearing in the horizontal selection area (Block 176b). Whether the operator indicated a desire to scroll up or scroll down the list of protocol names in the window or scroll box, control is transferred to transition Block H2 provided for illustration purposes to indicate that the operator may then select another option of processing on the list of protocol names including further scrolling up the list, further scrolling down the list, adding a name to the protocol list, accepting a name appearing in the horizontal selection area of the window or scroll box or selecting the ESCape option.

Based upon a determination at 175c that the ESCape option was selected, control is transferred to transition Block H resulting in display at 170 of all the protocol parameters with the present values. An example of this display containing parameters and values is illustrated in FIG. 6M. This would then permit the choice of further changing protocol parameters, saving the protocol, or beginning the exercise.

A determination is made at 175d whether the operator has selected the ADD option. If the ADD option was selected, the operator enters a name at 177 via the keyboard. The name entered by the operator via the keyboard is then added to the list of protocol names, a portion of which appears in the window. The values of the protocol parameters defined by the operator will be stored in association with the name keyed in by the operator. The storage will occur in accordance with the database architecture previously described. The protocol defined by the operator can then be retrieved in the future by selecting the protocol name in the scroll box via the keyboard or the touch screen. Control is then transferred to transition Block A resulting in the display at 104 of the protocol operation options including the CREATE, REMOVE and RETRIEVE PROTOCOL options as illustrated in FIG. 6B.

In the event that the list in the window portion of the scroll box is not scrolled UP or DOWN, the ESCape option is not selected and the ADD option is not selected, a determination is made at 175e whether the operator selected the ACCEPT option. If the ACCEPT option was selected, the parameter values displayed at 170, an example which is illustrated in FIG. 6M, replace those parameter values of the parameters associated with the protocol appearing in the horizontal selection area of the window or scroll box. It will be understood by those skilled in the art that storage of the new values can be accomplished in a number of ways. The parameter values previously associated with the parameter name in the horizontal selection area can be deleted and the new values are written into the same storage locations. A second method provides over-writing of the old values by the new values in the same storage location. A third method is based on indirect accessing via pointers by altering the pointers to point from the previous values to the new values. Regardless of which method is used, the result is the same in that the new values, i.e. the parameter values displayed at 170 and defined by the operator, are the new values associated with the protocol name in the horizontal selection area (Block 178). Once replacement of the values is made, control is transferred to transition Block A resulting in the display of the protocol options at 104 as illustrated in FIG. 6B thereby permitting the operator to create, remove, or retrieve a protocol. In the event the ACCEPT option also is not selected by the operator, control is transferred to transition Block H2 provided for illustration purposes to indicate that the scroll box containing the partial list of protocol names will remain as displayed until some positive action is taken on the part of the operator.

Based upon a determination at 172c that the BEGIN EXERCISE option was selected, a prompt is made on the display at 179 seeking verification of the selection to begin the exercise. The prompt is in the form of "ARE YOU SURE?" The operator then responds to the verification prompt by entering the verification via the touch screen or in the alternative, the keyboard at 180. A determination is made at 181 generally as to whether the operator responded in the affirmative or the negative to the verification prompt. Based upon a conclusion of 181a that the operator selected the "yes" option, thereby responding to the verification prompt in the affirmative, control is transferred to transition Block J. Transfer of control to transition Block J results in starting of the training exercise beginning with operator selection of how the results of the exercise are to be displayed. Based upon a determination at 181b that the operator selected the "no" option indicating a negative response to the verification prompt, control is transferred to transition Block H. Transfer of control to transition Block H results in continuous display of FIG. 6M whereby the operator can select from the ESCAPE, SAVE or BEGIN EXERCISE options. Finally, if neither the "yes" or "no" options were selected, the system waits until the operator selects one of the responses to the verification prompt, either in the affirmative or negative. This waiting until a selection is made by the operator is indicated by transition Block H4.

DETAILED OPERATION: PROTOCOL REMOVAL

Figure 5K:
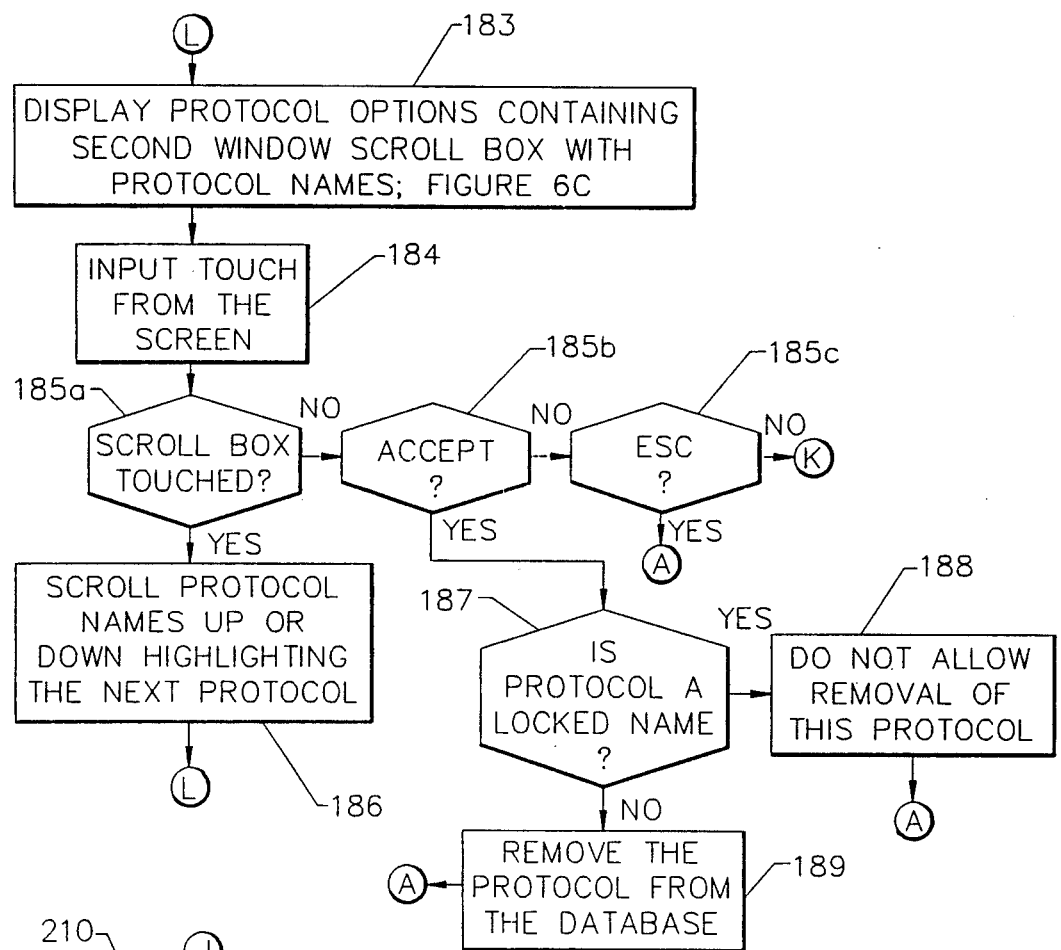

Referring to FIG. 5K, the control flow resulting from selection by the operator to remove the particular protocol appearing in the highlighted selection area of the scroll box will now be described. Control was transferred to transition Block L based on the determination at 106b of FIG. 5A that the REMOVE PROTOCOL option was selected. As a result of selection of the REMOVE PROTOCOL option, a scroll box containing a partial list of protocol names is displayed at 183. An example of the display containing the partial list of protocol names in the scroll box is illustrated in FIG. 6C. The operator has the option of scrolling up or down the list of protocol names appearing in the window portion, accepting the protocol name presently in the highlighted or horizontal selection area of the window portion of the scroll box or selecting the escape option. Once the operator has selected an option at 184 by touching the appropriate portion of the touch screen, a determination is made generally at 185 whether the scroll box was touched, i.e. whether the up or down portion of the scroll box was touched.

Based upon a determination at 185 that the scroll box was touched at the UP indicator at the top of the scroll box, the list of protocol names will be moved downward at 186 resulting in the previous name appearing in the highlighted or horizontal selection area. Similarly, based upon a determination at 185*a* that the scroll box was touched at the DOWN indicator in the scroll box, the protocol names listed in the window will be moved upward at 186 resulting in the succeeding name in alphabetical order appearing in the horizontal selection area as a result of the down indication (Block 183). Control is then transferred to transition Block L permitting further scrolling of the protocols in the scroll box.

A determination is made at 185*b* whether the operator selected the ACCEPT option. If the ACCEPT option was selected, a determination is made at 187 whether a particular protocol accepted is a locked protocol. An example of a locked protocol name which cannot be removed from the database is one of the standard protocols, e.g. isokinetic. Since these protocols are standard they are protected so as to prevent inadvertent deletion by an operator. If the protocol is locked, the protocol will not be removed from the database (Block 188) and an indication is made to the operator that the protocol name desired to be deleted from the database was a locked or protected protocol name. Control is then transferred to transition Block A which results in display of the protocol options as illustrated in FIG. 6B.

However, if the protocol name does not identify a locked or protected protocol, the protocol associated with that name is deleted at 189 from the database. The manipulation of the database architecture was previously discussed with reference to FIG. 4. It will be understood by those skilled in the art as to how to manipulate the database in order to accomplish deletion of this particular protocol. For example, the deletion may be performed by deleting the protocol name or deleting the index or key access into the database rather than deleting all of the data accessible via the index, key or protocol name. Control is transferred to transition Block A resulting in display at 104 of FIG. 5A of the protocol options. The display containing the protocol options including CREATE, REMOVE and RETRIEVE is illustrated in FIG. 6B.

DETAILED OPERATION: PROTOCOL RETRIEVAL

Referring to FIG. 5L, the control flow of protocol processing in relation to a selection by an operator to retrieve a particular protocol will now be described. As previously mentioned, based upon a determination at 105*c* of FIG. 5A that the operator selected the RETRIEVE option from the protocol options displayed at 104, control is transferred to transition Block K. Operator selection of the RETRIEVE PROTOCOL option results in display at 190 of the scroll box containing a partial list of protocol names in the scroll box. An example of a scroll box containing a partial list of protocol names is illustrated in FIG. 6C. A determination is made generally at 191 as to which option is selected by the operator in terms of indicating that the scroll box be scrolled UP or DOWN, ACCEPTING the protocol name appearing in the horizontal selection area of the scroll box or selecting the escape option. This determination is illustrated as a multiple decision block generally at 191.

Based upon a determination at 191*a* that the scroll box was touched, the partial list of protocol names appearing in the window portion of the scroll box will be scrolled up or down. Specifically, if the UP area of the scroll box was touched by the operator, the partial list appearing within the window will be moved downward at 192 resulting in the previous protocol name in alphabetic order appearing in the horizontal selection area. Similarly, if the DOWN indicator of the scroll box was touched by the operator, the partial list of protocol names appearing in the window or scroll box will be moved upward at 192 resulting in the succeeding protocol name in alphabetical order appearing in the horizontal selection area.

Control is then transferred to transition Block K provide for simplicity of illustration to indicate that the display of the scroll box will remain unchanged until the operator makes a further selection in terms of scrolling the box, ACCEPTing the protocol name appearing in the horizontal selection area or selecting the ESCape option.

Based upon a determination at 191*b* that the ACCEPT option was selected by the operator, the protocol name appearing in the horizontal selection area is retrieved at 193. Retrieval of the data, i.e. protocol options and parameter values, associated with this particular protocol name from the data files is in accordance with the previous description of the database architecture. A determination is made at 194 whether the protocol identified by the protocol name is locked or protected. In the event that the protocol name which is retrieved is a locked name as determined at 194, the locked protocol options associated with the locked protocol name are displayed at 195. The operator then has the option of either escaping the present mode or beginning an exercise session based upon the selected protocol, albeit locked.

Once the operator has made a selection of these two options at 196, a determination is made at 197*a* whether the ESCape option was selected. If the ESCape option was selected by the operator, control is transferred to transition Block A resulting in display of the protocol options at 104 of FIG. 5A including CREATE, REMOVE, or RETRIEVE PROTOCOL as illustrated in FIG. 6B. However, based upon a determination at 197*b* that the BEGIN option was selected by the operator, control is transferred to transition Block J in order to start the training exercise based upon the selected, albeit locked, protocol. In the event that neither the ESCape option nor the BEGIN option were selected by the operator, control is transferred to decision Block K2 provided for ease of illustration to indicate that the system waits in its current state and continues to display the protocol options of the locked protocol name until the operator makes a selection of either ESCape or the BEGIN option.

Based upon a determination at 194 that the operator selected a protocol name which was not locked, the unlocked protocol options are displayed at 198. The operator can then select among the options of ESCape, EDIT or BEGIN. As a result of the operator selection at 199 of one of the options, a determination is made at 200 as to which option was selected. Based upon a determination at 200a that the ESCape option was selected by the operator, control is transferred to transition Block A resulting in display at 104 of FIG. 5A of the protocol options including CREATE, REMOVE, or RETRIEVE as illustrated in FIG. 6B. This permits the operator to select another protocol option other than retrieval or in the alternative to select retrieval again and select a different protocol name.

If it is determined at 200b that the operator selected the EDIT option, control is transferred to transition Block B resulting in display at 115 of the protocol parameters options which the operator may choose to modify or change as illustrated in FIG. 6D. This permits the operator to modify a protocol rather than use the one it has selected via this retrieval process. If neither the ESCape or EDIT option was selected, a determination is made at 200c whether the operator selected the BEGIN option. Based upon a determination at 200c that the BEGIN option was selected, control is transferred to transition Block J resulting in start of the training exercise by permitting the operator to control what is to be done with any results of the training exercise. Finally, if none of the options were selected, control is transferred to transition Block K1 provided for purposes of illustration to indicate that the system waits continuing to display the unlocked protocol options for the retrieved protocol, until the operator takes some positive action and selects one of the three options, namely ESCape, EDIT or BEGIN.

DETAILED OPERATION: TRAINING FEEDBACK MODIFICATION

Figure 5M:
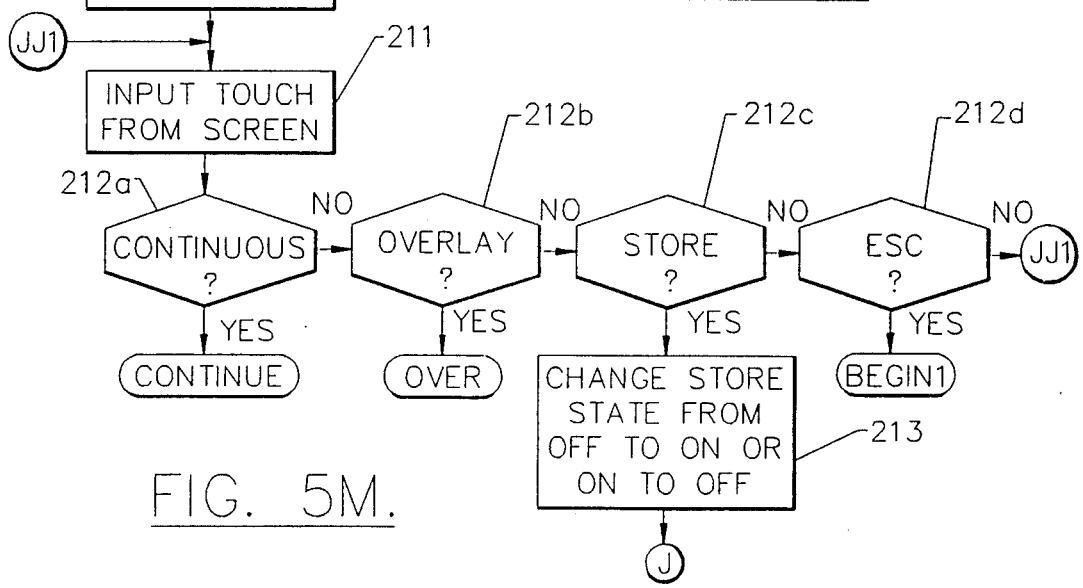

Control of the protocol definition and training exercise which is reached via transition Block J from various points in the protocol definition and selection process will now be described. Referring to FIG. 5M, the control flow for operator selection of what is to be done with any results in the form of data obtained from a training exercise based upon a selected protocol name is illustrated. As a result of transfer of control to transition Block J based upon a desire at various points in the protocol selection process to begin an exercise based upon the protocol selected, a menu is displayed at 210 containing the training feedback options including CONTINUOUS, OVERLAY, and STORE. These options are displayed on display 30a as illustrated in FIG. 6N. Selection of the CONTINUOUS feedback option results in a continuous sweep of the patient's production over a specified time interval in a graph format over the length of the trace. Selection of the OVERLAY feedback provides display of a given curve on the screen during the exercise which the patient can use as a "goal" to achieve maximal or submaximal, e.g. average, results. Finally, selection of the STORE EXERCISE feedback option results in the storage of the data results of the exercise to be performed by the patient. The STORE EXERCISE feedback option is often used in combination with the evaluation option which can be performed at a later date in the future.

More specifically, selection of the option can be made by the operator simply by touching the appropriate feedback option on the touch screen display within the box enclosing the particular option. Alternatively, the operator may enter the digit located to the left of the option on the keyboard. Once the input has been made at 211 by the operator, a determination is made generally at 212 as to which option was selected. This is illustrated by a multiple decision block at 212. Based upon a determination at 212a that the CONTINUOUS feedback option was selected, control is transferred to transition Block CONTINUE. If the continuous feedback option was not selected, a determination is made at 212b whether the overlay feedback option was selected. If the overlay feedback option was selected by the operator, control is passed to transition Block OVER. In the event that neither the CONTINUOUS nor the OVERLAY feedback options were selected by the operator, a determination is made at 212c whether the STORE EXERCISE option was selected by the operator. If selected, the state of the STORE EXERCISE option is "toggled" or "flip-flopped" at 213 from either "off" to "on" or from "on" to "off". Toggling to "on" of this parameter results in storage of the data obtained from the exercise or evaluation. Once the state of the STORE EXERCISE feedback option has been toggled, control is transferred to transition Block J provided for ease of illustration to indicate that the training feedback option display illustrated in FIG. 6N will continue to be displayed at 210 in order to permit the operator to select other training feedback options as well as to change his or her mind as to the status of the start exercise feedback option.

Finally, if none of the training feedback options were selected by the operator, a determination is made at 212d whether the operator selected the ESCape option. Based upon a determination at 212d that ESCape was selected, control is passed to transition Block BEGIN1. This results in display at 101 of FIG. 5A of the exercise options such as isokinetic and protocol. If neither the ESCape option nor any of the three training feedback options was selected, control is transferred to transition Block JJ1 provided for ease of illustration to indicate that the training feedback option parameters retain their present value and the training feedback option display as illustrated in FIG. 5N remains displayed until the operator makes an appropriate selection of one or more of the training feedback options or the ESCape option.

DETAIL OPERATION: CONTINUOUS TRAINING FEEDBACK CONTROL MODIFICATION

Figure 5N:
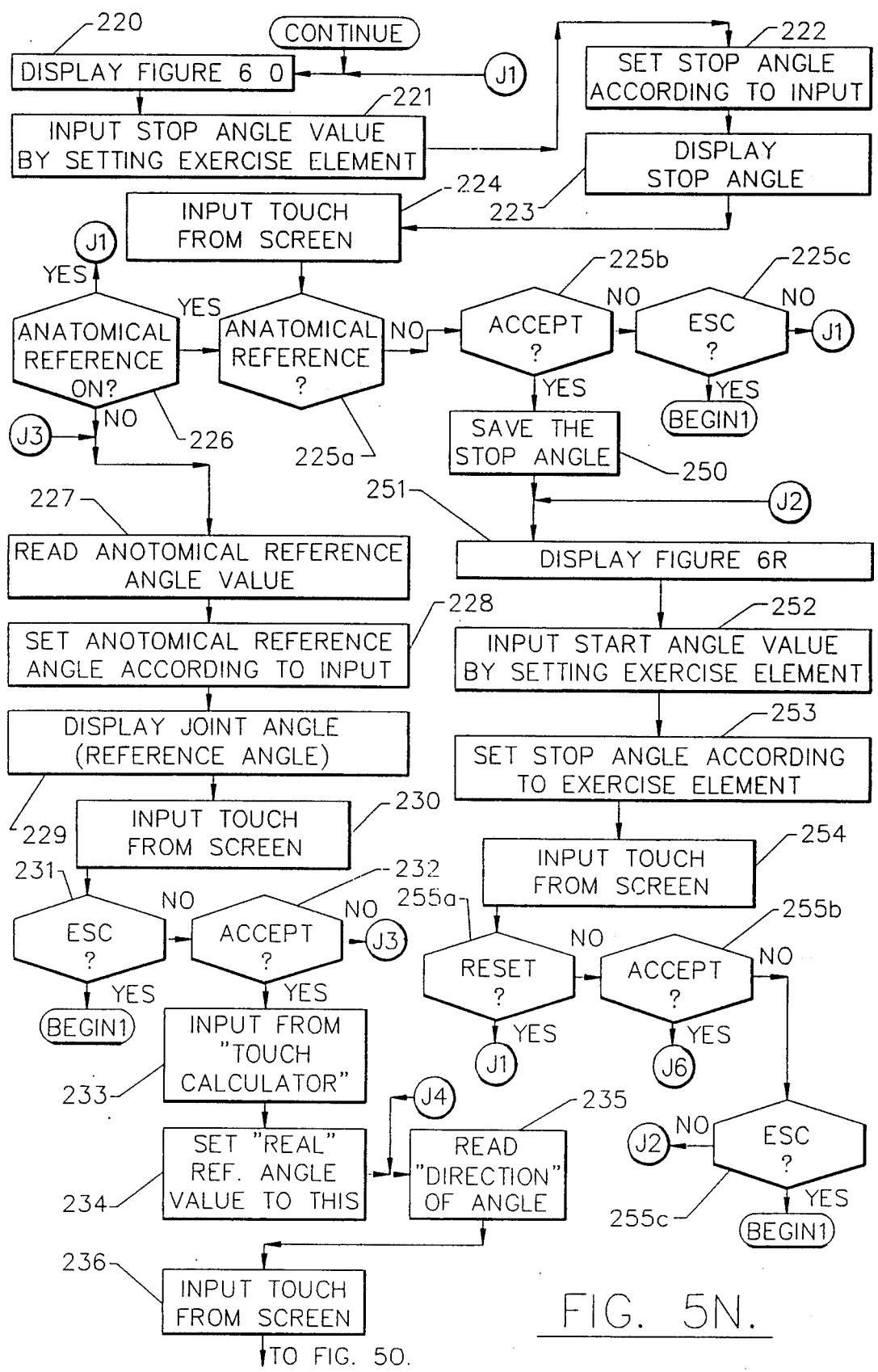
Figure 5O:
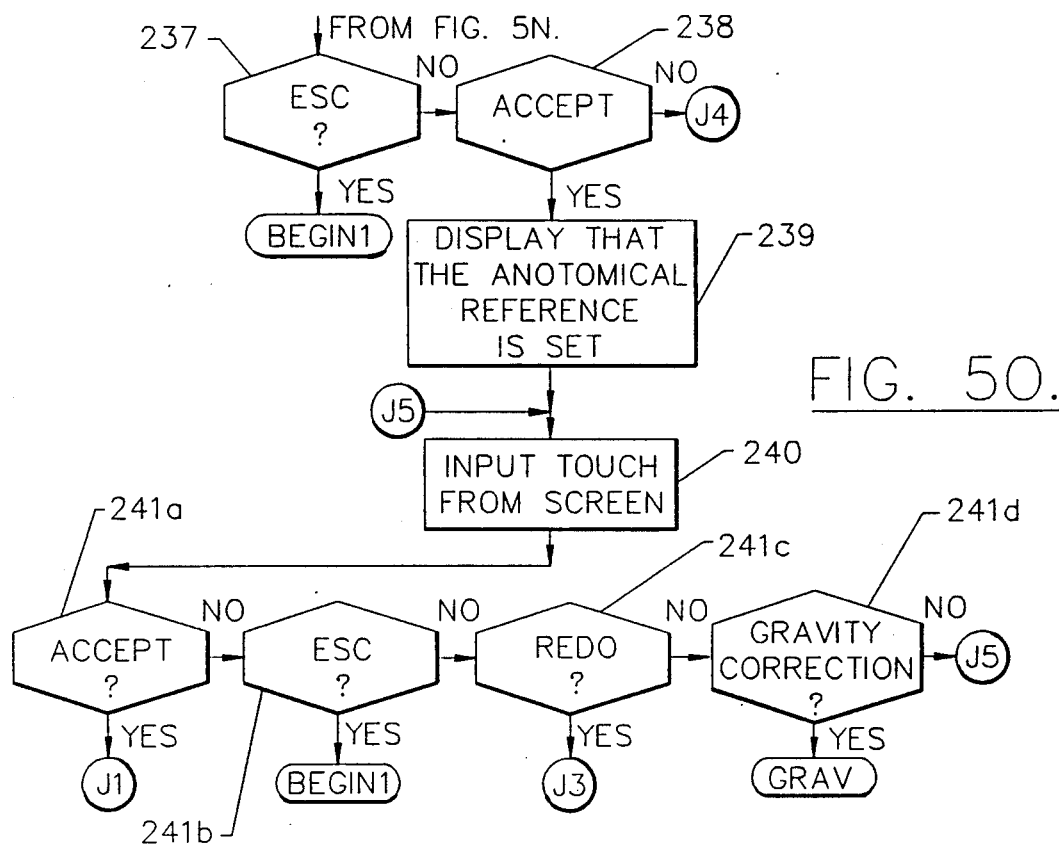

Referring to FIGS. 5N and 5O, the setting of the various parameter values for the selection of the continuous training feedback option will now be described. As previously mentioned, if the operator made an indication on the touch screen or the keyboard that he or she desired to make use of the CONTINUOUS training feedback option, control was transferred to the transition Block CONTINUE in FIG. 5M. Selection of this continuous training feedback option requires the initial setting of the start and stop angles for the range of motion in order to ensure safety during the training or evaluation procedures. The operator is prompted at 220 for the input of the STOP ANGLE via the display illustrated in FIG. 6O. The operator then proceeds to enter the stop angle value at 221 by locating the exercise element such as the exercise arm at the appropriate place for the particular patient where the rotation of the particular exercise should stop. The stop angle of the exercise machine is set according to the stop angle value at 222 entered by the operator via placement of the exercise element. Finally, the stop angle is displayed at 223 in degrees as illustrated in the example display screen in FIG. 6O.

The exercise machine also has the capability of providing an ANATOMICAL REFERENCE. This option permits anatomical reference to the patient's joint so that the correct goniometric angles can be displayed on the screen during training. Referring to FIG. 6O, the ANATOMICAL REFERENCE option is either in the "off" state or the "on" state. Selection of the option is controlled by a toggle or flip-flop. As illustrated in FIG. 6O, the ANATOMICAL REFERENCE option is presently in the "off" state. In order to toggle the state of the anatomical reference to "on", the operator must indicate at 224 selection of the ANATOMICAL REFERENCE. A determination is made at 225 whether the state of the anatomical reference was toggled by the operator. If the operator switched the state of the anatomical reference, a determination is then made at 226 as to whether the anatomical reference is "on". If the anatomical reference is in the "on" state at 226, control is transferred to transition Block J1 provided for ease of illustration to indicate that the displayed at 220 as illustrated in FIG. 6O remains on display 30a permitting the user to change the stop angle or ACCEPT the stop angle or in the alternative to ESCape the present start and stop angle initialization process.

Figure 6P:
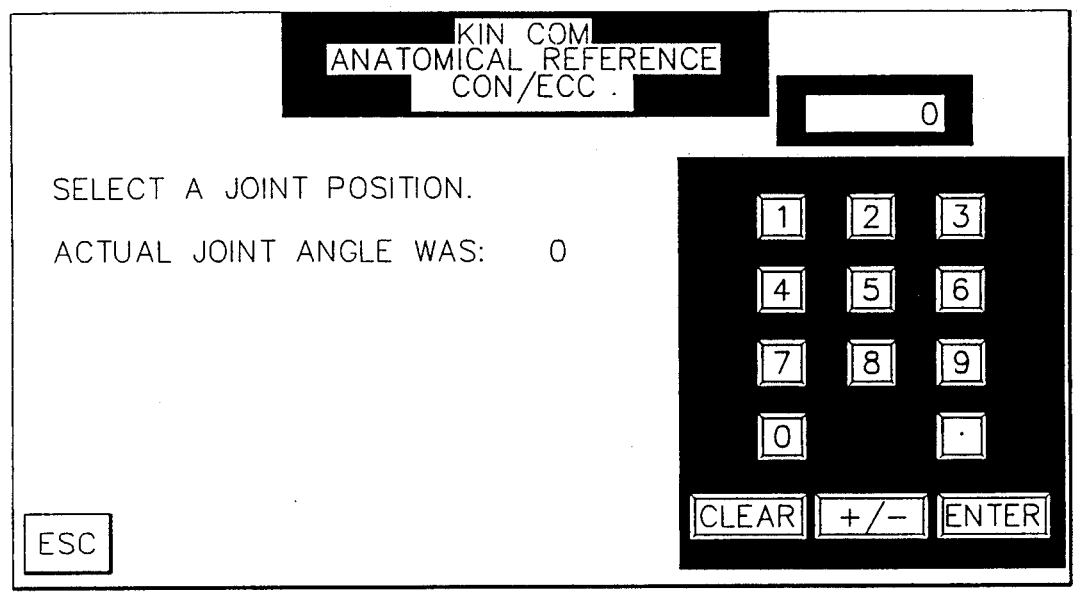

If ANATOMICAL REFERENCE is set to "off", the operator is prompted via the display illustrated in FIG. 6P to anatomically reference the exercise element with the patient's joint position. This is accomplished by moving the exercise element 227 to be used by the particular joint to be exercised to the appropriate reference angle whereby the angle will appear on the screen. The anatomical reference angle of the exercise machine is set according to the joint position at 228. The actual joint angle as the reference angle is then displayed at 229. The operator then can ACCEPT the angle or ESCape the present angle setting process to begin the exercise. Consistent with the touch screen interface, the operator selection is made at 230 making the appropriate indication on the touch screen. Based upon a determination at 231 that the ESCape option was selected by the operator, control is transferred to transition Block BEGIN1. This results in display at 101 of FIG. 5A of the exercise options, e.g. isokinetic or protocol.

A determination is made at 232 as to whether the ACCEPT option was selected. If the ACCEPT option was not selected, control is transferred to transition Block J3 provided for ease of illustration to indicate that the system waits seeking either reading of a new ANATOMICAL REFERENCE angle or selection of the ESCape or ACCEPT options via the touch screen. Based upon a determination at 232 that the ACCEPT option was selected, the touch calculator appearing in FIG. 6P will appear on the display permitting the operator to enter at 233 the displayed anatomical angle via the touch calculator. The "real" reference angle value is set at 234 according to the value entered by the operator via the touch calculator.

Figure 6Q:
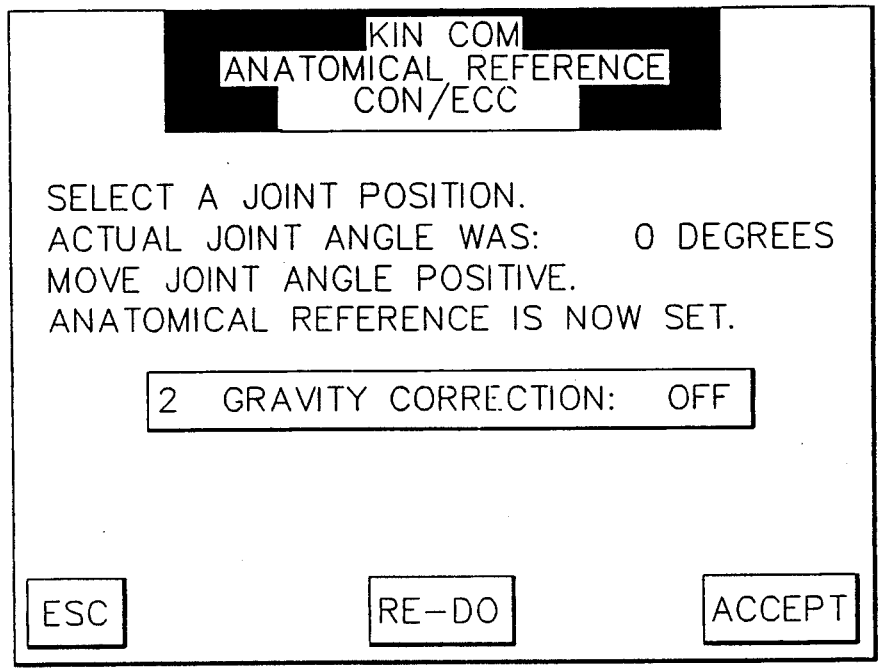

The operator is then prompted to move the joint angle in a more positive direction as appears in the display in FIG. 6Q. The exercise element is moved in a positive direction and the system reads this direction of the angle at 235. The positive direction is relative to the side of the machine which the patient is sitting on (see FIG. 1). If the patent has changed sides of the machine, the positive direction will be accordingly reversed. The operator may then either ACCEPT the angle values or ESCape the present processing mode to begin the exercise. An indication of ACCEPTANCE or ESCape is made at 236 and a determination is made at 237 as to whether the ESCape option has been selected. If the ESCape option was selected, control is transferred to transition Block BEGIN1. This results in display at 101 of FIG. 5A of the exercise options such as isokinetic and protocol.

A determination is made at 238 whether the operator selected the ACCEPT option. Based upon a determination at 238 that the ACCEPT option was not selected, control is transferred to transition Block J4 provided for illustration to indicate that the system remains unchanged, permitting the operator to enter a new direction of the angle.

Based upon a determination at 238 that the ACCEPT option was selected, the operator is notified via display 30a by a prompt at 239 that the anatomical reference is now set, as illustrated in FIG. 6Q. The operator then has the options of ESCaping the present mode, ACCEPTING the present settings, REDOing the present settings, or selecting the GRAVITY CORRECTION option. Consistent with the touch screen interface for selection of previous options, the operator enters his or her selection at 240 via the touch screen.

A determination is made as to which option was selected. The determination flow is illustrated generally at 241 by multiple decision blocks. Based upon a determination at 241a that the ACCEPT option was selected, control is transferred to transition Block J1 resulting in display at 220 of FIG. 6O permitting the operator to set the start angle or reset the stop angle. Based upon a determination at 241b that the ESCape option was selected, control is transferred to transition Block BEGIN1. This results in display at 101 of FIG. 5A of the exercise options, e.g. isokinetic or protocol. If it is determined at 241c that the REDO option was selected on a touch screen by the operator, control is transferred to transition Block J3 provided for purposes of illustration to indicate that the operator can reset the anatomical reference angle value beginning at 227.

If neither the ACCEPT, ESCAPE or REDO options were selected, a determination is made at 241d as to whether the GRAVITY CORRECTION option was selected. If the GRAVITY CORRECTION option was selected, control is transferred to transition Block Grav. This permits collection of training or evaluation data adjusted in order to allow for corrections based upon gravity. Based upon a determination at 241d that the gravity correction also was not selected, control is transferred to transition Block J5 provided for illustration to indicate that the system waits, continuing to display the display illustrated in FIG. 6Q until some positive action is taken on the part of the operator to select one of the four available options.

Based upon a determination at 225 that the ANATOMICAL REFERENCE option was not selected by the operator, a determination is made at 225b whether the ACCEPT option was selected by the operator. If the ACCEPT option was not selected, a determination is made at 225c whether the ESCape option was selected. If the ESCape option was selected, control is transferred to transition Block BEGIN1 resulting in display at 101 of FIG. 5A of the exercise options such as isokinetic and protocol. However, if the ACCEPT option and the ESCape option were not selected, control is transferred to transition Block J1 provided for ease of illustration to indicate that the system waits, continuing to display FIG. 6O until the operator takes some positive action by making an indication on the touch screen of a selection of one of the options.

Figure 6R:
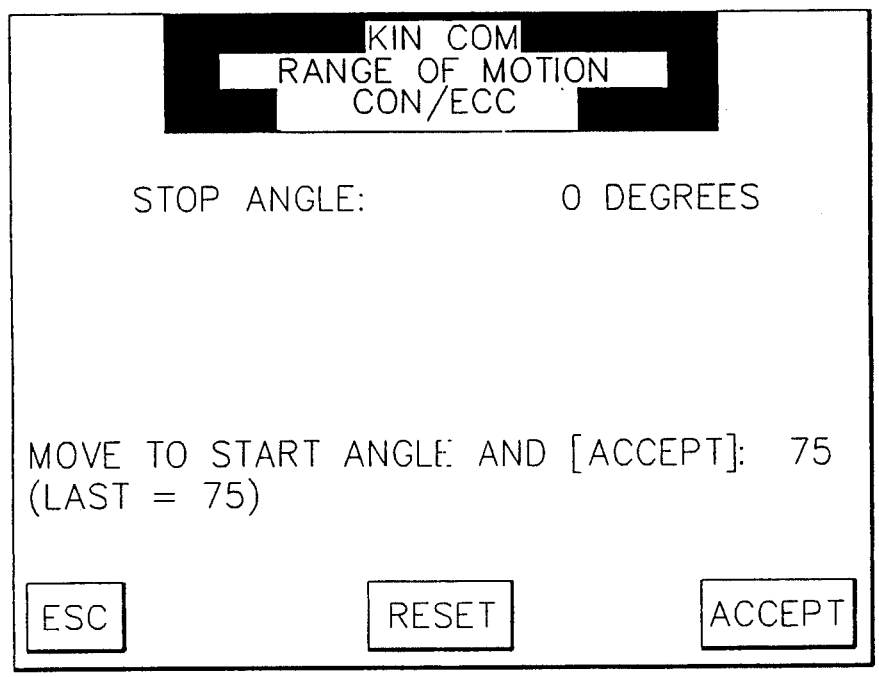

Based upon a determination at 225b that the ACCEPT option was selected, the stop angle set at 222 is stored in memory at 250. The stored stop angle is then displayed at 251 along with the present position of the exercise element. An example of the display is illustrated in FIG. 6R. The operator can then enter a start angle value at 252 by locating the exercise element at a desired position. The start angle is set at 253 equal to the angle determined by the location of the exercise element.

The operator then has the options of RESETting the stop and start angles, ACCEPTing the angles as set which appear in the display as illustrated in FIG. 6R or ESCaping the present stop and start angle setting process to select a different exercise. A selection is entered at 254 on the touch screen as is consistent with the touch screen interface. A determination is made based upon sequential multi-decision blocks, indicated generally at 255, as to which option was selected. Based upon a determination at 255a that the operator desires to RESET the stop and start angles, control is transferred to transition Block J1 resulting in the display of FIG. 6O at 220 whereby the operator can again set the stop and start angles as well as the anatomical reference. Based upon a determination at 225b that the ACCEPT option was selected, control is transferred to transition Block J6 which begins the continuous training exercise collection portion of the process.

Finally, if the RESET and ACCEPT options were not selected, a determination is made at 255c whether the operator selected the ESCape option. If the ESCape option was selected, control is transferred to transition Block BEGIN1 resulting in display at 101 of FIG. 5A of the exercise options such as isokinetic and protocol. However, if none of the options were selected by the operator, control is transferred to transition Block J2 provided for illustration to indicate that the system remains in its present state continuing to display FIG. 6O until such time as the operator takes some positive action by indicating a selection of the RESET, ACCEPT, or ESCape options via the touch screen.

DETAILED OPERATION: EXERCISING AND CHANGE BOX

Figure 5P:
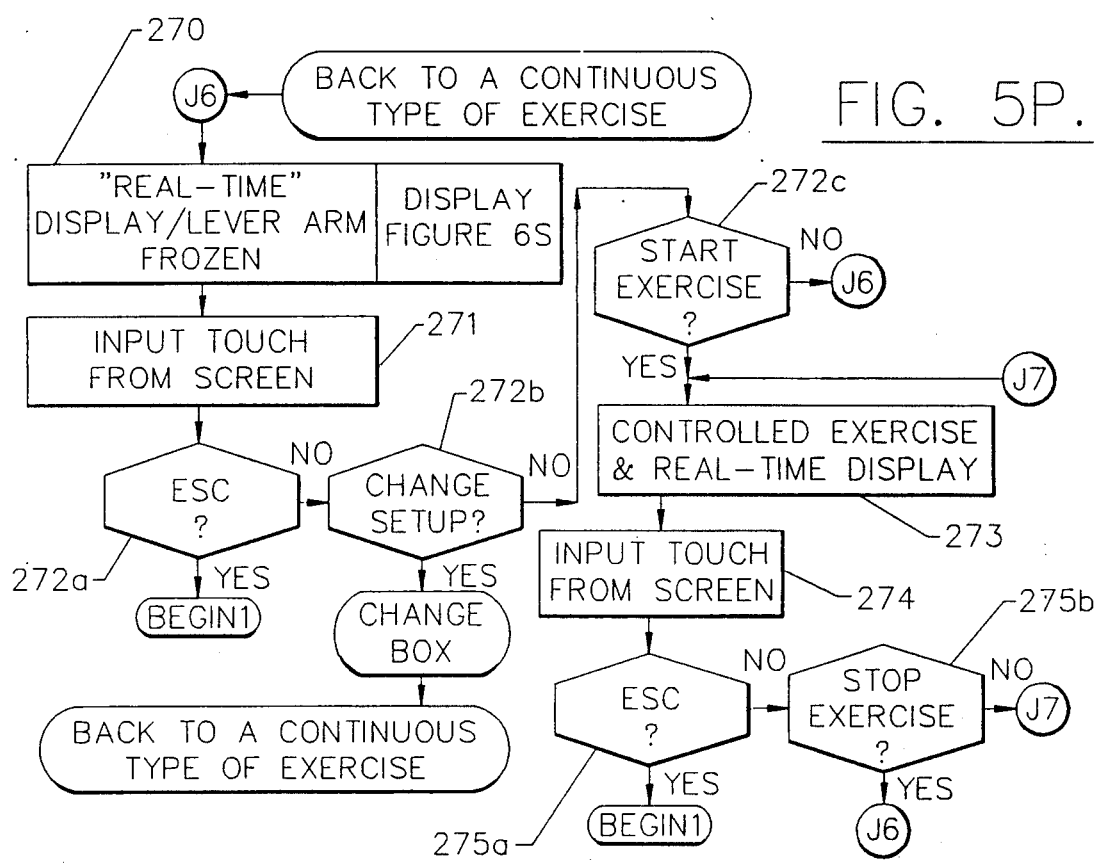
Figure 6S:
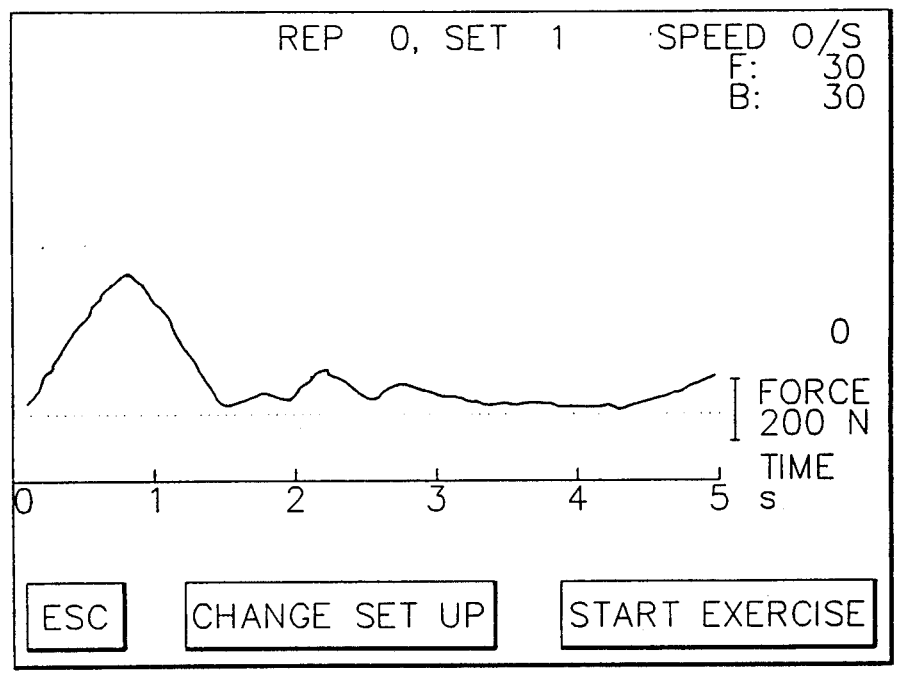

Referring to FIG. 5P, the control flow for initialization of the continuous training and exercise collection portion of the computer controller for the exercise machine will now be described. Based upon a determination at 255b of FIG. 5N that the stop and start angles were accepted, the continuous training exercise collection portion is begun resulting in a "real time" display at 270. Additionally, the exercise element is presently locked or frozen at 270 so as to prevent movement of the exercise element until actual training (exercise) or evaluation begins. The trace along with the forward and backward speed values, the reps and number of sets as well as the options to START EXERCISE, CHANGE SET UP (parameter values) or ESCape the present continuous exercise collection portion processing are displayed on a screen, an example of which is illustrated in FIG. 6S.

Consistent with the touch screen interface, the operator makes an indication of the selected option at 271 via the touch screen. A determination is made as to which option the operator has selected. This determination is illustrated generally at 272 by sequential multiple decision blocks. Based upon a determination at 272a that the ESCape option was selected, control is transferred to transition Block BEGIN1 resulting in display at 101 of FIG. 5A of the exercise options, e.g. isokinetic and protocol. This permits the operator to abort the present exercise and select a different exercise.

If it is determined at 272b that the operator selected the CHANGE SETUP option on the touch screen, control is transferred to transition Block CHANGE BOX. CHANGE BOX permits the operator to change the values of protocol parameters and then return to the exercise. Once CHANGE BOX processing is complete, control is transferred back to the continuous type of exercise collection portion resulting in the real time display and continual locking of the exercise element at 270.

Following a determination that the ESCape and the CHANGE SETUP option were not selected, a determination is made at 272c whether the START EXERCISE option was selected. If the START EXERCISE option was not selected, the display illustrated in FIG. 6S remains on display 30a and the computer controller for the exercising machine waits until the operator selects one of the options on the touch screen.

Figure 6T:
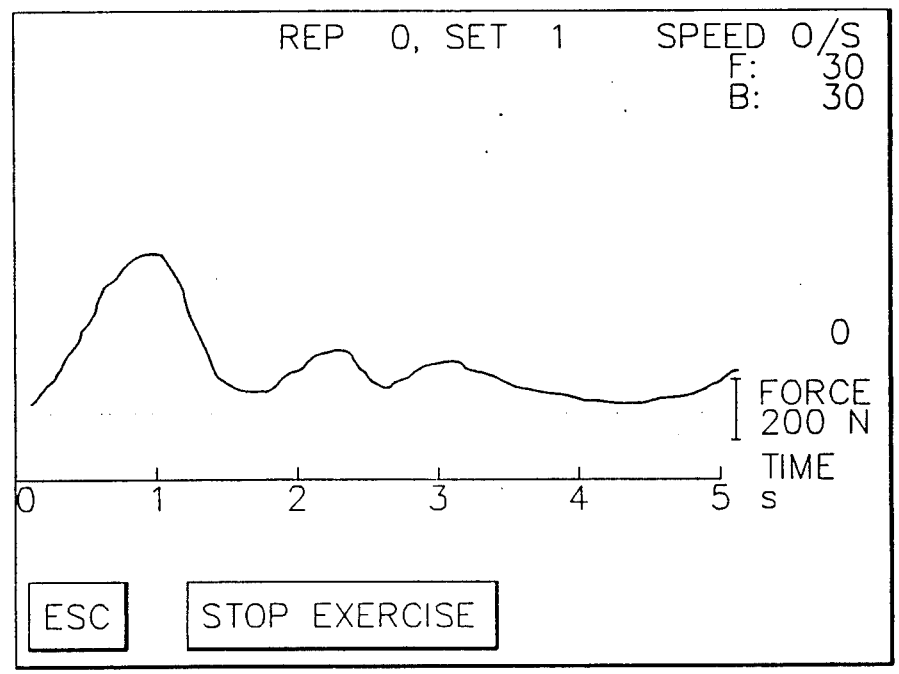

Based upon a determination at 272c that the START EXERCISE option was selected, the exercising machine is controlled by the computer controller based upon the parameter values for the protocol selected containing any operator defined protocol parameter values (Block 273). A real time display containing the forward and backward speed, a count of the exercise repetitions and sets, and a trace of the exercise (training) or evaluation progress appears on the display 30a at 273, an example of which is illustrated in FIG. 6T. The exercise or training by the patient continues until the operator selects either the ESCape or the STOP EXERCISE option. Consistent with the touch screen interface for option selection, an option is selected by making an indication of the desired option on the touch screen at 274.

A determination is made as to whether the ESCape or the STOP EXERCISE option was selected. This determination is illustrated generally at 275 as sequential multiple decision blocks. Based upon a conclusion at 275a that the escape option was selected, control is transferred to transition Block BEGIN1 resulting in display at 101 of FIG. 5A of the exercise options such as isokinetic or protocol. This permits the operator to abort the present exercise and select a new exercise.

Based upon a determination at 275b that the STOP EXERCISE option was selected, control is transferred to transition Block J6 provided for illustration purposes to indicate that the display, such as the example illustrated in FIG. 6S, appears on the display 30a portion of monitor 30 and the exercise element such as the lever arm will be frozen to prevent movement of the exercise element as a safety precaution against injury (Block 270). This permits the operator to stop the exercise and readjust parameter values. If neither the ESCape or STOP EXERCISE options are selected, the exercise machine will continue to be controlled by the computer controller in accordance with the parameter values for the particular protocol selected and the results of the exercise or evaluation will continue to be displayed at 273 similar to the example in FIG. 6T. Exercise continues until the ESCape or STOP EXERCISE option is selected by the operator or the number of repetitions and sets is equivalent to the corresponding parameter values.

Figure 5Q:
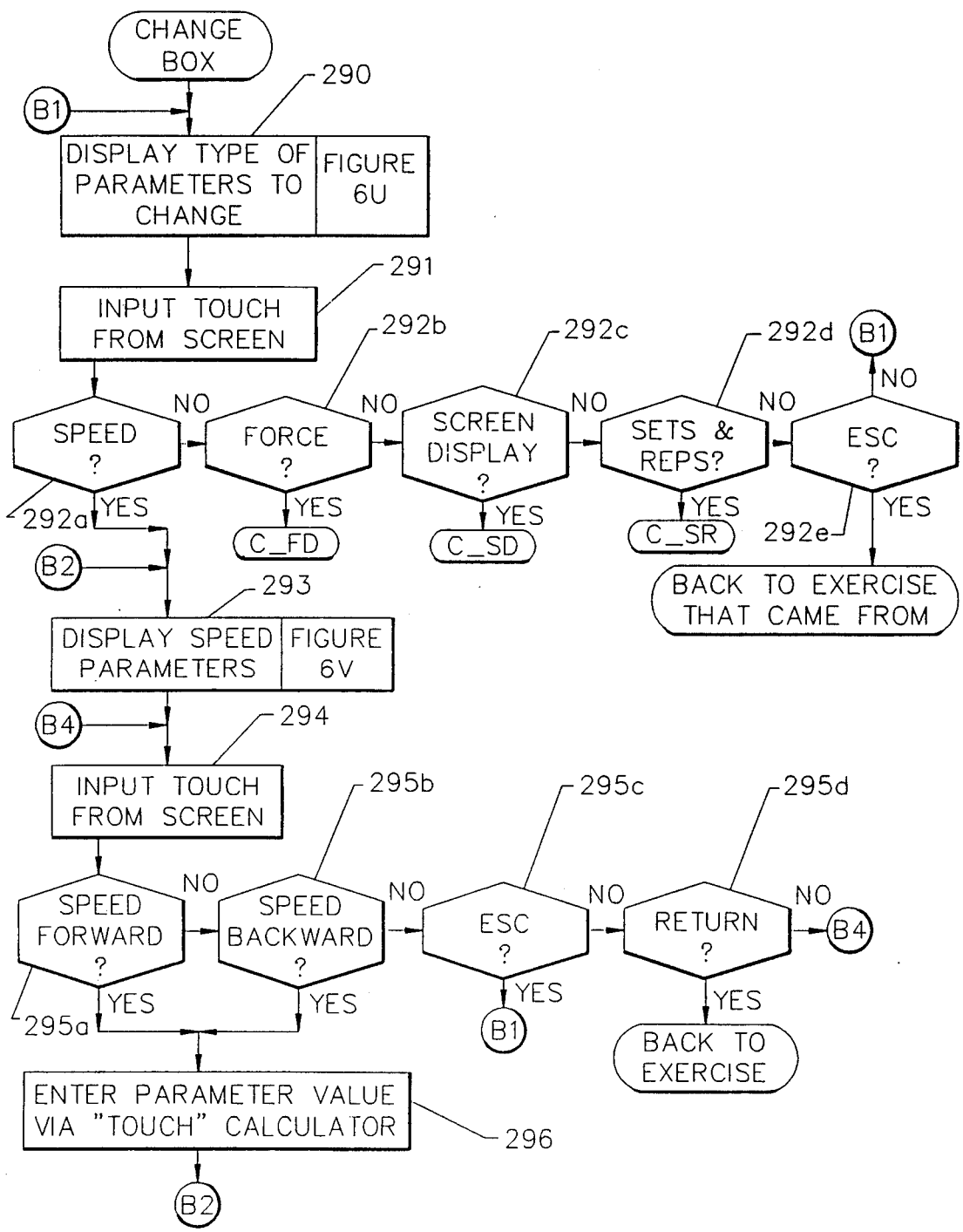
Figure 6U:
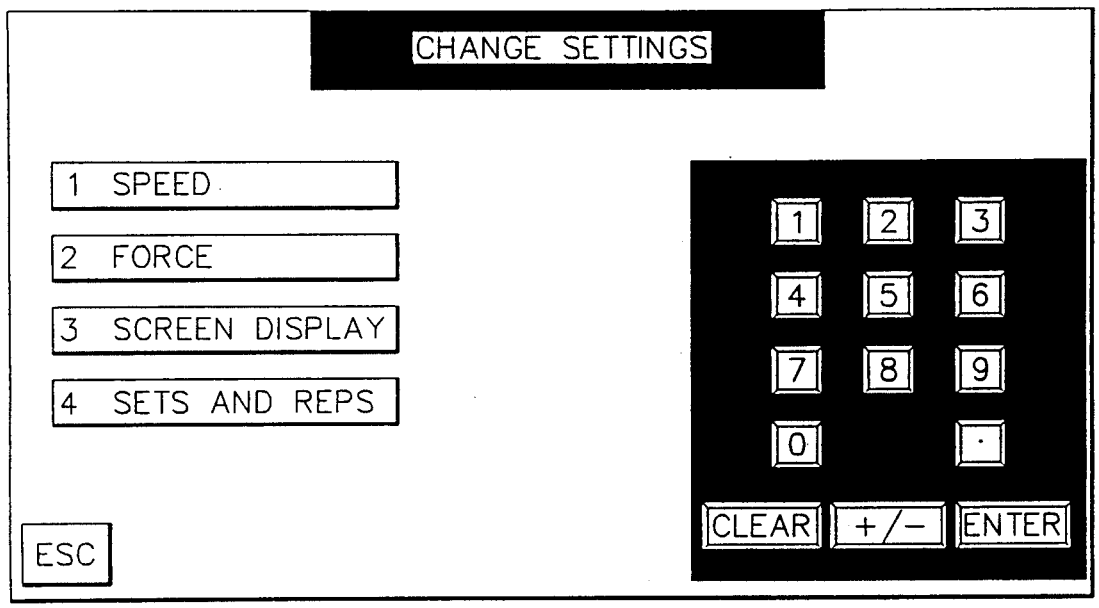

Referring to FIG. 5Q, the control flow of the process for changing protocol parameter values during an exercise based upon a determination at 272b of FIG. 5P of a selection of the CHANGE SETUP option will now be described. Selection of the CHANGE SETUP option results in the display at 290 of the type of protocol parameters which can be changed. An example of the display appearing on display 30a is illustrated in FIG. 6U. Consistent with the touch screen interface selection of options, a selection of the protocol parameter to be changed is entered via the touch screen at 291.

Figure 6V:
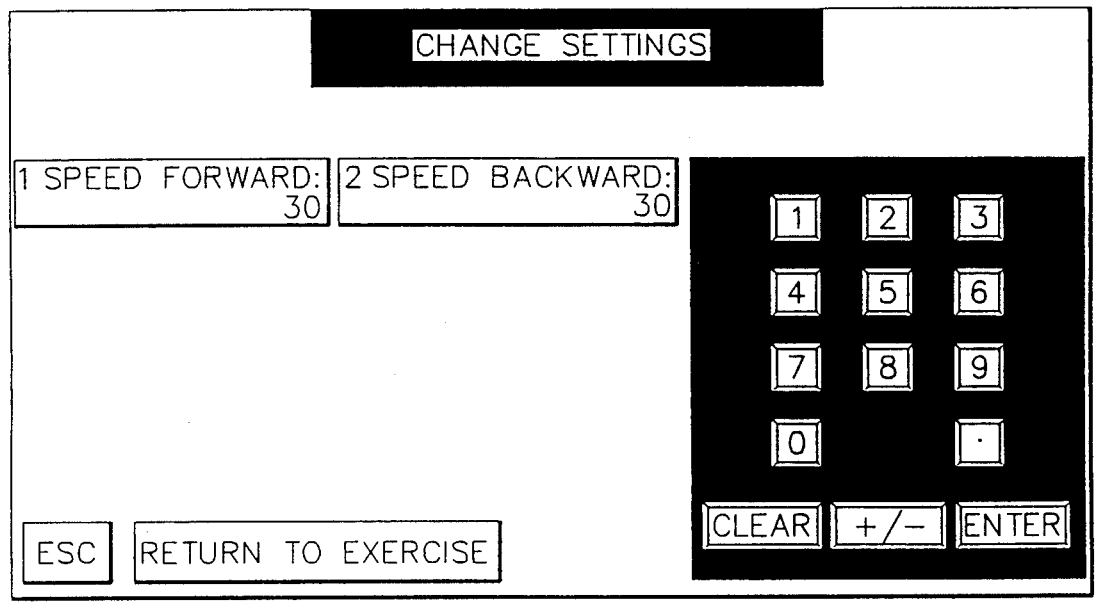

A determination is made generally at 292 as to which option the operator selected. This determination is illustrated as sequential multiple decision blocks. Based upon a conclusion at 292a that the SPEED protocol parameter is to be changed, the SPEED protocol parameters will be displayed at 293 on display screen 30a, an example of which is illustrated in FIG. 6V. As previously described in relation to selecting the speed parameter values, the operator first selects at 294 the speed parameter to be set via the touch screen. The SPEED FORWARD and SPEED BACKWARD parameters can be set in either order and are set by making an indication of the parameter to be set on the touch screen followed by entry of the parameter value on the touch calculator located on the right portion of the screen as illustrated in FIG. 6V.

Based upon a determination at 295a that the SPEED FORWARD parameter was selected to be set or at 295b that the SPEED BACKWARD parameter is to be set, the parameter value is entered at 296 via the touch calculator. Control is then transferred to transition Block B2 resulting in display at 293 of the new values for the speed parameters selected. The display of the speed parameters and the new values, if changed, will remain on display 30a until the operator either changes the parameters again, selects the ESCape option, or selects the RETURN TO EXERCISE option.

Based upon a determination at 295c that the ESCape option was selected, control is transferred to transition Block B1 resulting in display at 290 of the protocol parameters which can be changed, as illustrated in FIG. 6U. If neither the SPEED FORWARD or SPEED BACKWARD parameters were selected and the ESCape option was not selected, a determination is made at 295d whether the RETURN option was selected. If the RETURN option was selected, control is returned back to the exercise from which CHANGE BOX receives control. However, if it is determined that the RETURN option also is not selected, the system waits continuing to display FIG. 6V until the operator makes a selection of one of the options via the touch screen.

If it is determined at 292a that the SPEED protocol parameter option was not selected, a determination will be made sequentially as to whether the FORCE, SCREEN DISPLAY, or SETS AND REPS protocol parameter options were selected. Based upon a conclusion at 292b that the FORCE protocol parameter option was selected to be changed, control is transferred to transition Block C_FD, where the operator can change the force parameters and then return to the exercise. If it is concluded at 292c that the operator selected the SCREEN DISPLAY protocol parameters to be changed, control is transferred to transition Block C_SD. This permits the operator to change the settings of the screen display options and then return to continue the training or evaluation of the patient. Based upon a determination at 292d that the SETS AND REPS option was selected by the operator, control is transferred to transition Block C_SR. Selection of the SETS AND REPS protocol parameter permits the operator to change the number of sets or number of repetitions per set as well as the recovery time and then return to continue the training or evaluation based upon the new values.

Finally, if none of the protocol parameters have been selected, a determination is made at 292e whether the ESCape option was selected. If the ESCape option illustrated in FIG. 6U was selected, control is transferred back to the exercise from which the CHANGE BOX routine received control. However, if the ESCape option also was not selected, the display illustrated in FIG. 6U will continue to be displayed until the operator selects one of the protocol parameters to be changed or the ESCape option by making an indication at the appropriate location on a touch screen.

Figure 5R:
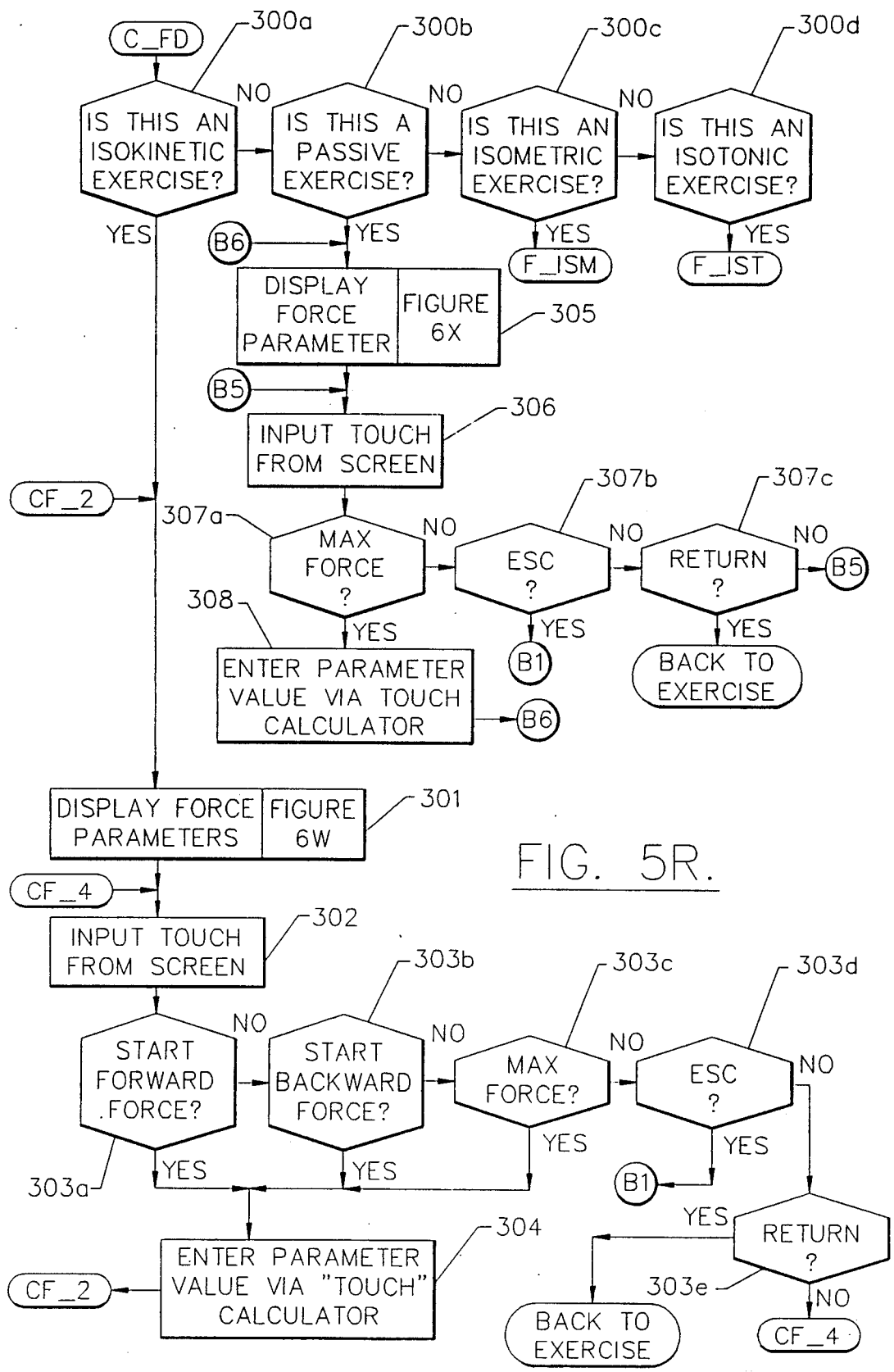

Referring to FIG. 5R, the control flow of modification of the force protocol parameters will now be described. Transition Block C_FD received control based upon a determination at 292b (FIG. 5Q) that the operator selected the FORCE parameters at 290 to be changed. A determination is first made as to which type of exercise is presently being performed. This determination, generally at 300, is made as consistent with other determinations where a multiple sequential decision block is required.

Figure 6W:
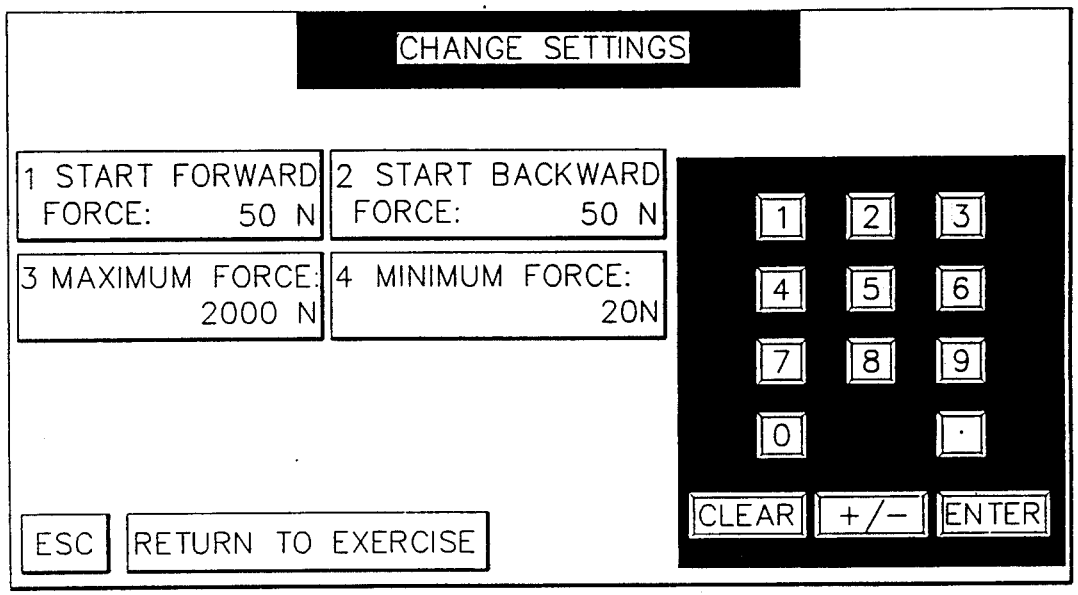

Based upon a determination at 300a, that the present exercise is an isokinetic exercise, the force parameters and values are displayed at 301. An example of the display is illustrated in FIG. 6W. Consistent with the touch screen interface, the operator makes the selection of the force parameter to be modified by indicating the selection at the appropriate location on the touch screen (Block 302) and entering the new parameter value for the selected force parameter via the touch calculator located on the right side of the display illustrated in FIG. 6W. A decision is made generally at 303 as to which of the options the operator has selected. This is illustrated as a multiple sequential decision block. Based upon a determination at 303a that the START FORWARD FORCE parameter was selected, at 303b that the START BACKWARD FORCE parameter was selected, or at 303c that the MAXIMUM FORCE parameter was selected, the value for that particular parameter selected is entered at 304 via the touch calculator. Control is then returned to transition Block CF_2 provided for purposes of illustrating that the display illustrated in FIG. 6W continues to be displayed containing the new values until the values of any of the parameters are charged or the ESCape or RETURN TO EXERCISE options are selected.

Based upon a conclusion at 303d that the ESCape option was selected by the operator, control is transferred to transition Block B1 resulting in display at 290 of FIG. 5Q of the protocol parameters which can be changed in mid-exercise. This permits the operator to change other protocol parameter values before returning to the exercise. If it is determined at 303e the operator selected the RETURN TO EXERCISE option, control is returned back to the exercise from which the CHANGE BOX routine received control. The exercise or evaluation then continues as controlled by the computer controller based upon the old parameter values and any new values set during the CHANGE BOX procedure. In the event none of the options are selected, the system waits, continuing to display the force settings as illustrated in FIG. 6W until the operator indicates the desire to change values of one or more of the force parameters or selects the escape or return to exercise option.

Figure 6X:
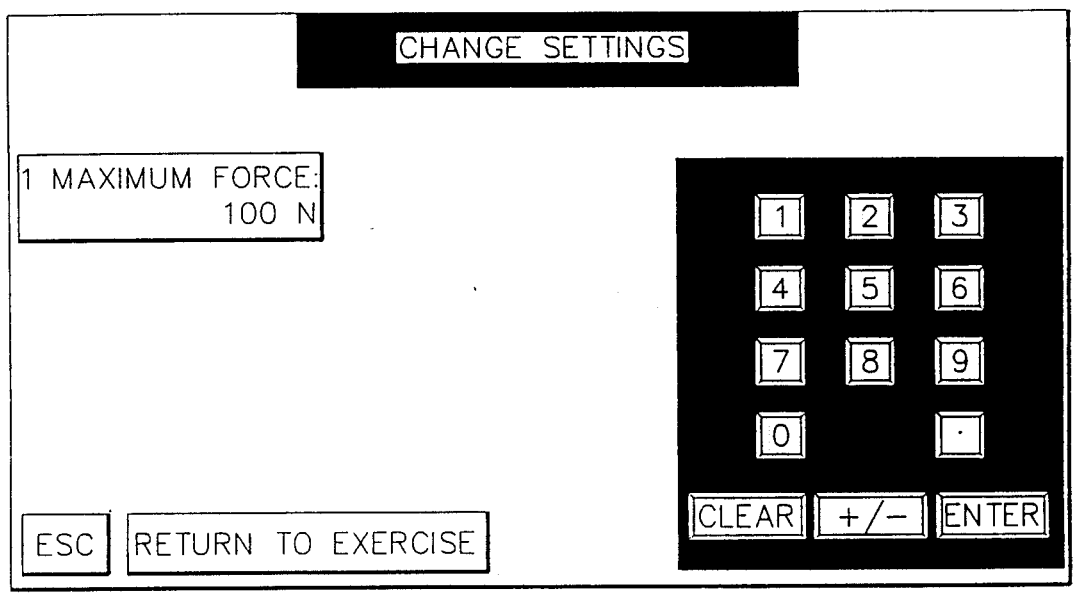

Based upon a conclusion at 300b that the present exercise is a passive exercise, the force parameters will be displayed at 305. An example of the display is illustrated in FIG. 6X. Consistent with previous forms of input, the operator selects the passive exercise force parameter to be changed at 306 by making an indication on the touch screen. Since this is a passive exercise, only the MAXIMUM FORCE parameter can be changed. A determination is made at 307a whether the MAXIMUM FORCE parameter has been selected for modification. If the MAXIMUM FORCE parameter was selected, the new value is entered at 308 on the touch calculator located at the right side of FIG. 6X. The new value for the maximum force parameter will be indicated in newtons of force adjacent to the maximum force parameter. The system waits until the operator changes the maximum force parameter value again or selects the ESCape or RETURN TO EXERCISE option.

Based upon a conclusion at 307a that the MAXIMUM FORCE parameter was not selected for modification, a determination is made at 307b whether the ESCape option was selected by the operator. If the ESCape option was selected by the operator, control is transferred to transition Block B1 resulting in display of the protocol parameters at 290 of FIG. 5Q which may be changed by the operator and which are illustrated in FIG. 6U. Alternatively, if it is determined at 307c that the RETURN TO EXERCISE option was selected, control is transferred back to the exercise from which the CHANGE BOX procedure received control resulting in the patient continuing training or evaluation whereby the exercise machine is controlled based upon the old parameter values and any new parameter values selected by the operator. If none of the options were selected, the computer controller waits as indicated by transition Block B5 until the operator indicates a desire to change the MAXIMUM FORCE parameter or selects the ESCape or RETURN TO EXERCISE option.

Based upon a determination at 300c in FIG. 5R that the present exercise is an isometric exercise, control is transferred to the transition Block F_ISM. Transition Block F_ISM transfers control to permit the operator to change the force parameters for isometric exercises so that the exercise machine can be controlled based on new values for the isometric exercise force parameters. Finally, based upon a conclusion at 300d that the present exercise is an isotonic exercise, control is transferred to transition Block F_IST. This permits the operator to change the force parameters related to isotonic exercises so as to control the exercise machine pursuant to the new values for the isotonic exercise currently in progress.

Figure 5S:
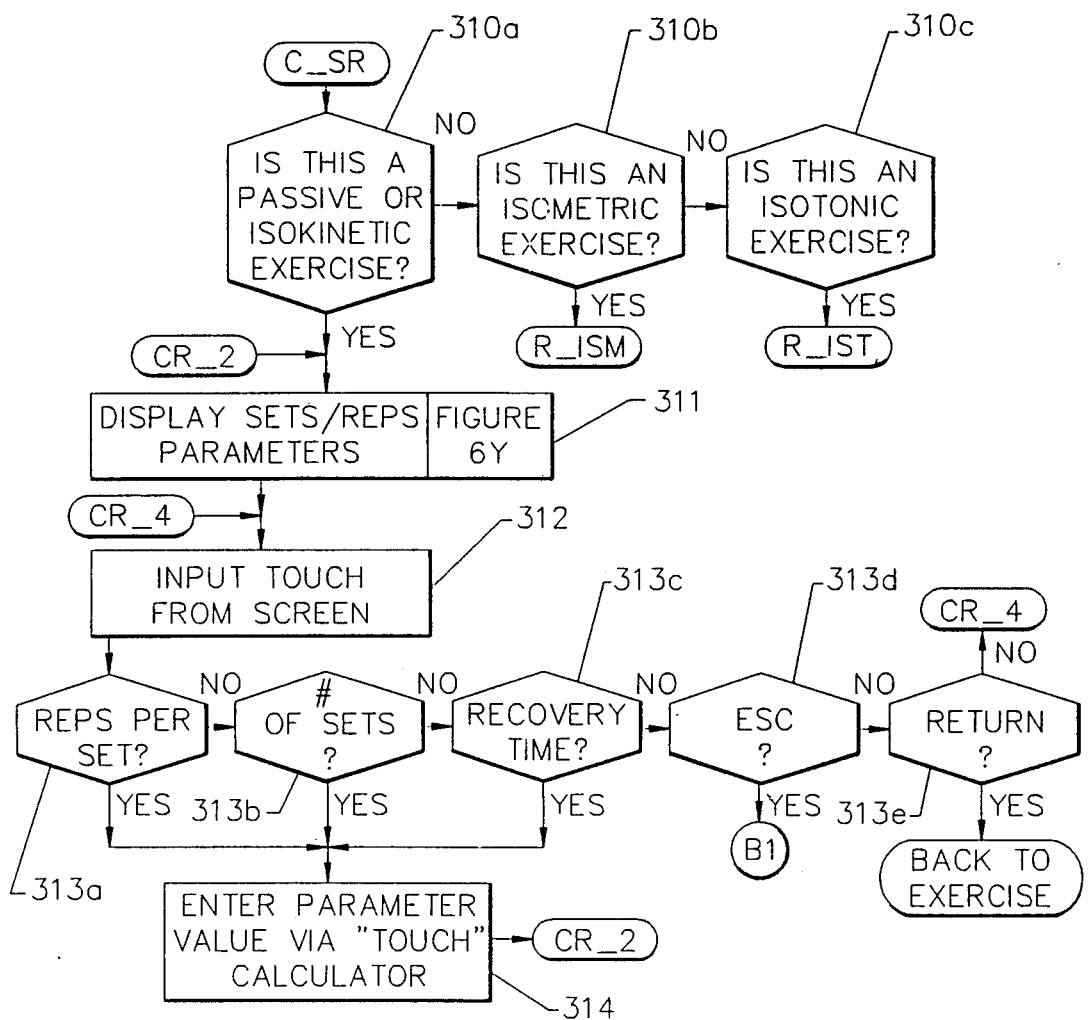
Figure 6Y:
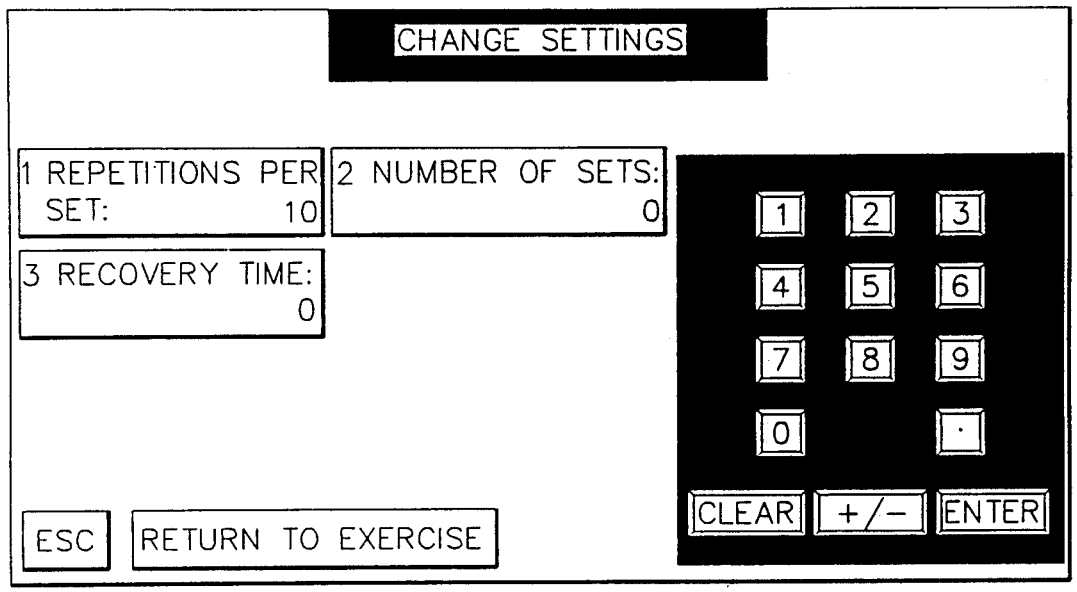

Referring to FIG. 5S, the control flow for modification of the sets and repetitions protocol parameters will now be described. Control is received as a result of a determination at 292d of FIG. 5Q that the operator indicated a desire to change the SETS AND REPS parameters. As was the case with the force parameter, a determination is made generally at 310 as to the type of present exercise. This is illustrated using a multiple sequential decision block. Based upon a conclusion at 310a that the present exercise is either a passive or isokinetic exercise, the present values for the repetitions and sets parameters as well as the recovery time are displayed at 311, an example of which is illustrated in FIG. 6Y. Consistent with the touch screen interface, the operator selects a parameter to be changed or the ESCape or RETURN TO EXERCISE option by making an indication in the appropriate location on the touch screen (Block 312).

Referring generally to 313 in FIG. 5S, the multiple decision block processing used to determine which option was selected by the operator is illustrated. Based upon the determination at 313a, 313b, and 313c, respectively, that the operator indicated a desire to modify the REPETITIONS PER SET value, to modify the NUMBER OF SETS value, or to modify the RECOVERY TIME value, the new value is entered at 314 via the touch calculator located on the right side of the display as illustrated in FIG. 6Y. As indicated by transition Block CR_2, control is returned to the display at 311 of the sets and repetitions parameters to permit further modification of the sets and repetitions parameters or selection of the ESCape or RETURN TO EXERCISE options.

Based upon a determination at 313d that the operator selected the ESCape option, control is transferred to transition Block B1 resulting in display of the protocol parameters at 290 in FIG. 5Q which the operator can change pursuant to the present exercise. These protocol parameters are displayed as illustrated in FIG. 6U. Finally, based upon a conclusion at 313e that the operator selected the RETURN TO EXERCISE option, control is transferred back to the exercise from which the CHANGE BOX processing received control. The patient will then continue the training or evaluation procedure whereby the exercise machine is controlled by the computer controller based on the old parameter values for the particular protocol and any new values set for the parameters during the CHANGE BOX processing.

Based upon a conclusion at 310b that the present exercise is an isometric exercise, control is transferred to transition Block R_ISM. This permits modification of the parameters for controlling the sets and repetitions options for an isometric exercise on the muscle exercise machine. Finally, if a determination is made at 310c that the present exercise is an isotonic exercise, control is transferred to transition Block R_IST. This permits modification by the operator of the values for the sets and repetition parameters for an isotonic exercise resulting in computer control of the exercising machine during an isotonic exercise based upon the new sets and repetition parameter values.

Figure 5T:
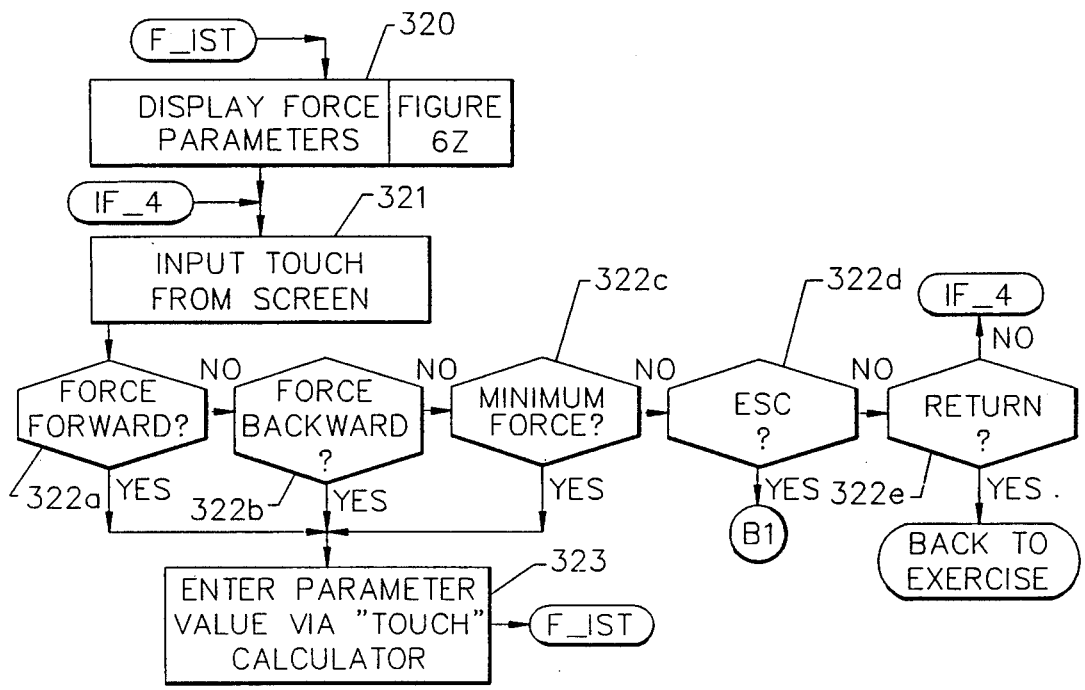
Figure 6Z:
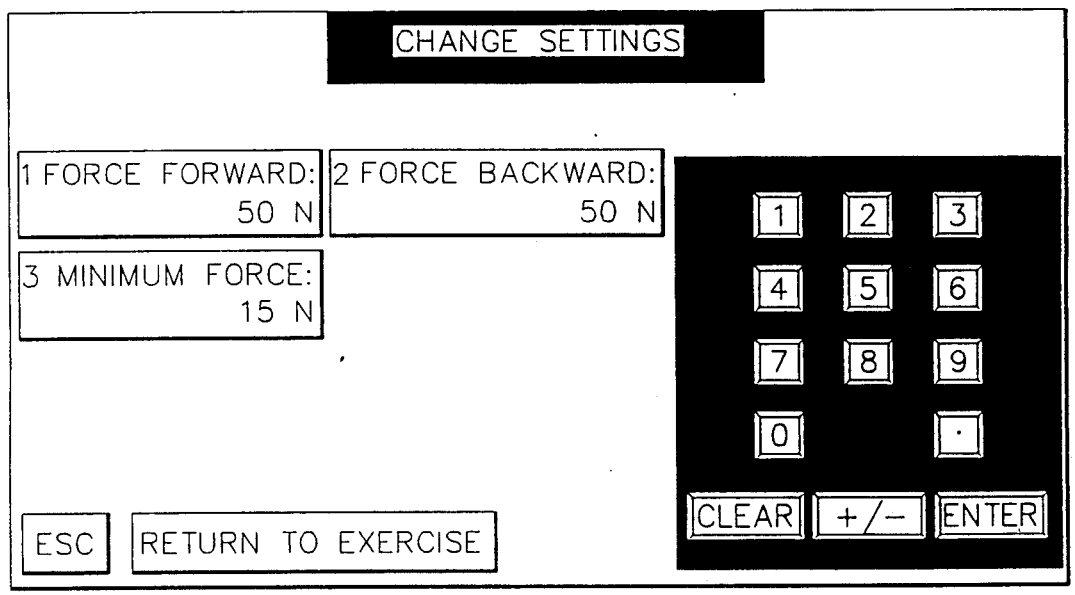
Figure 6A:
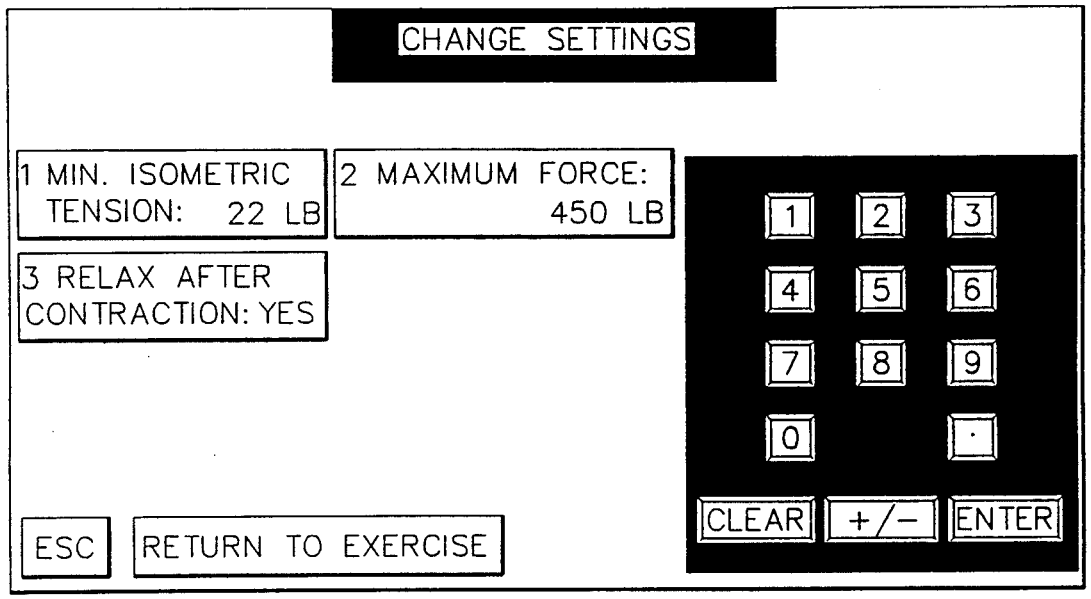
Figure 6B:
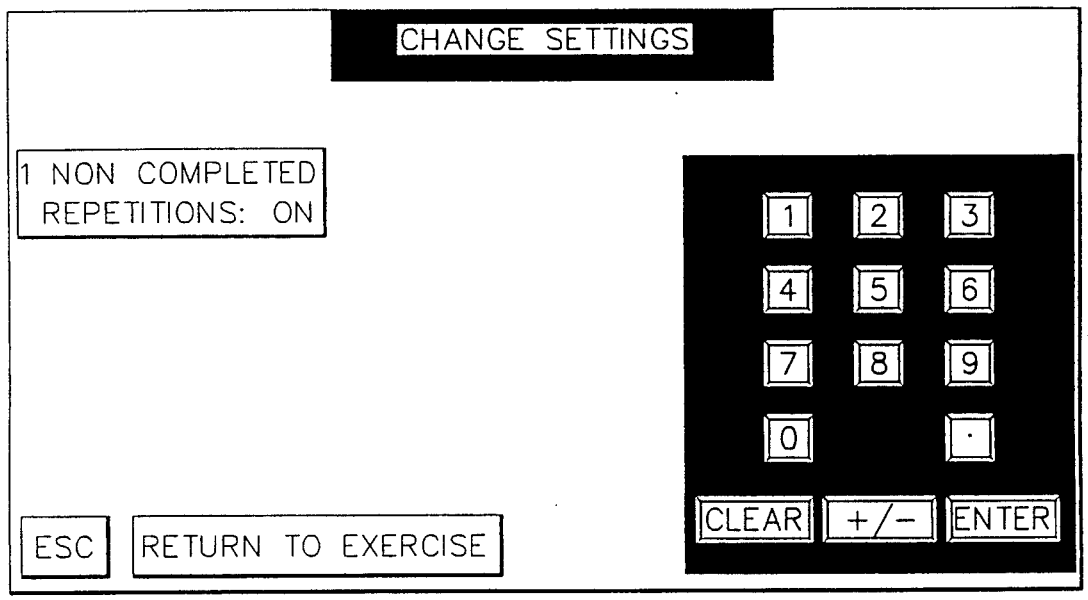
Figure 6C:
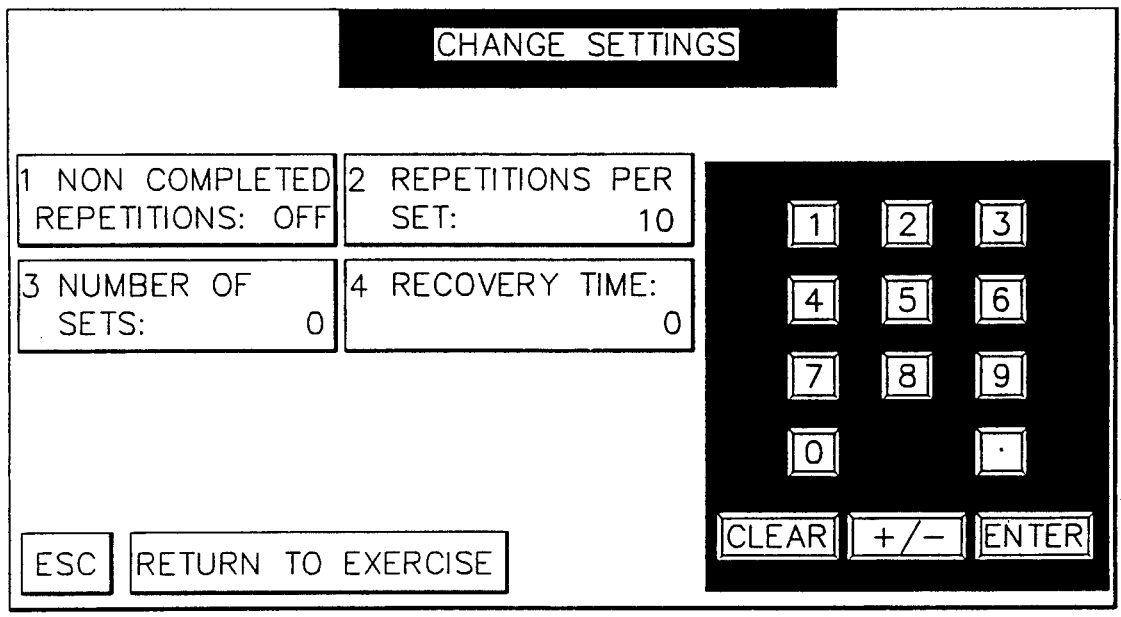
Figure 6D:
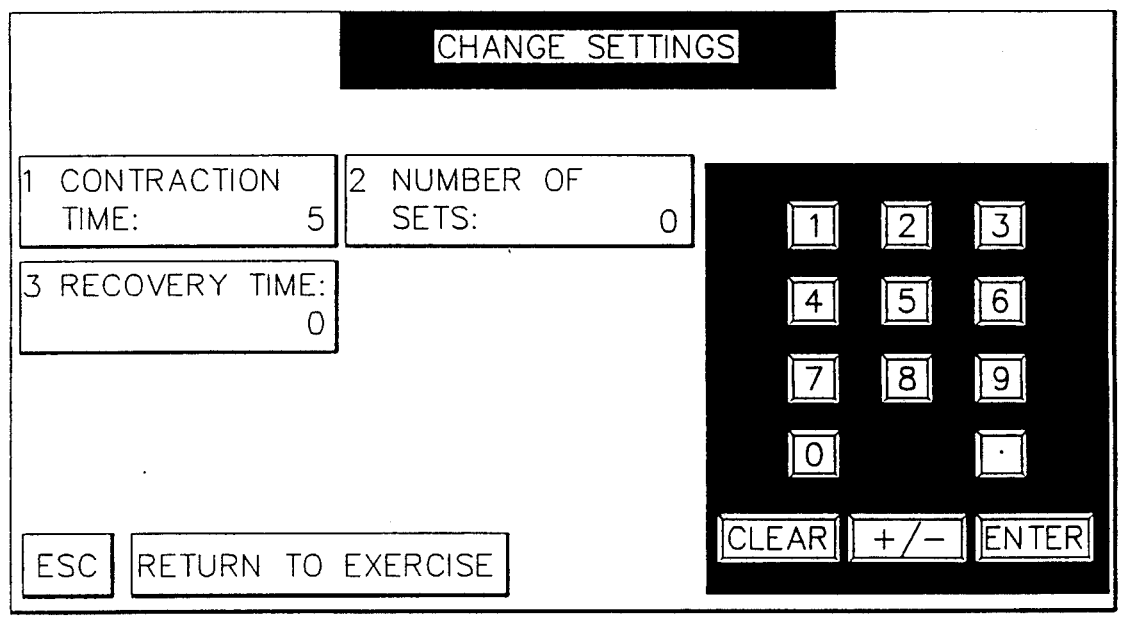
Figure 6E:
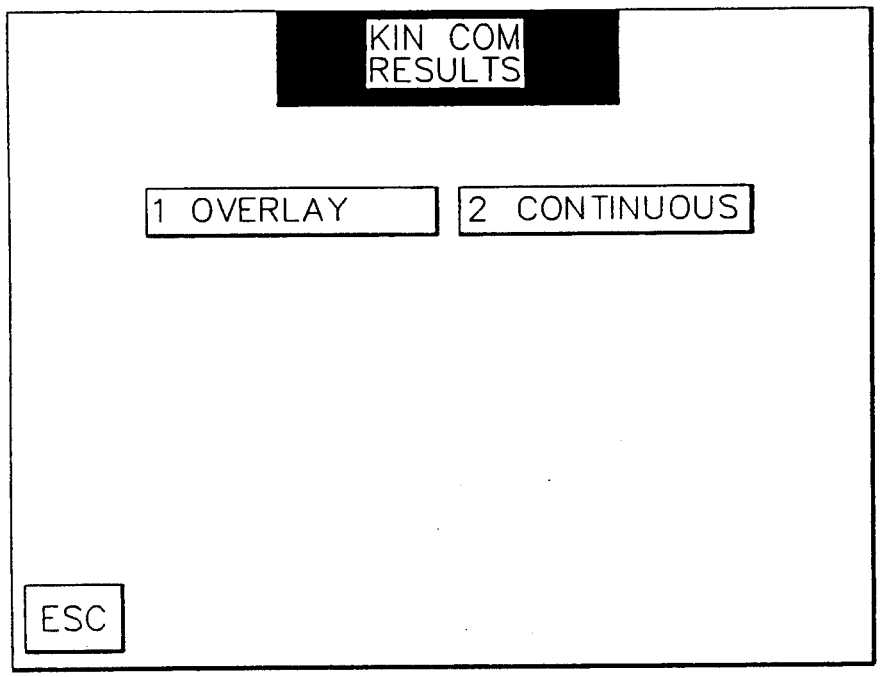
Figure 6F:
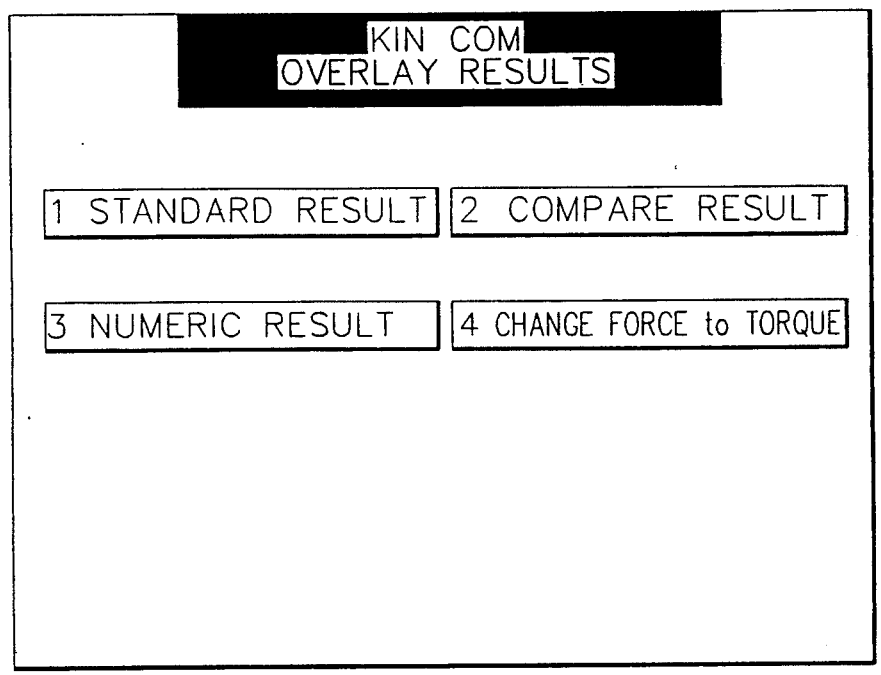
Figure 61I:
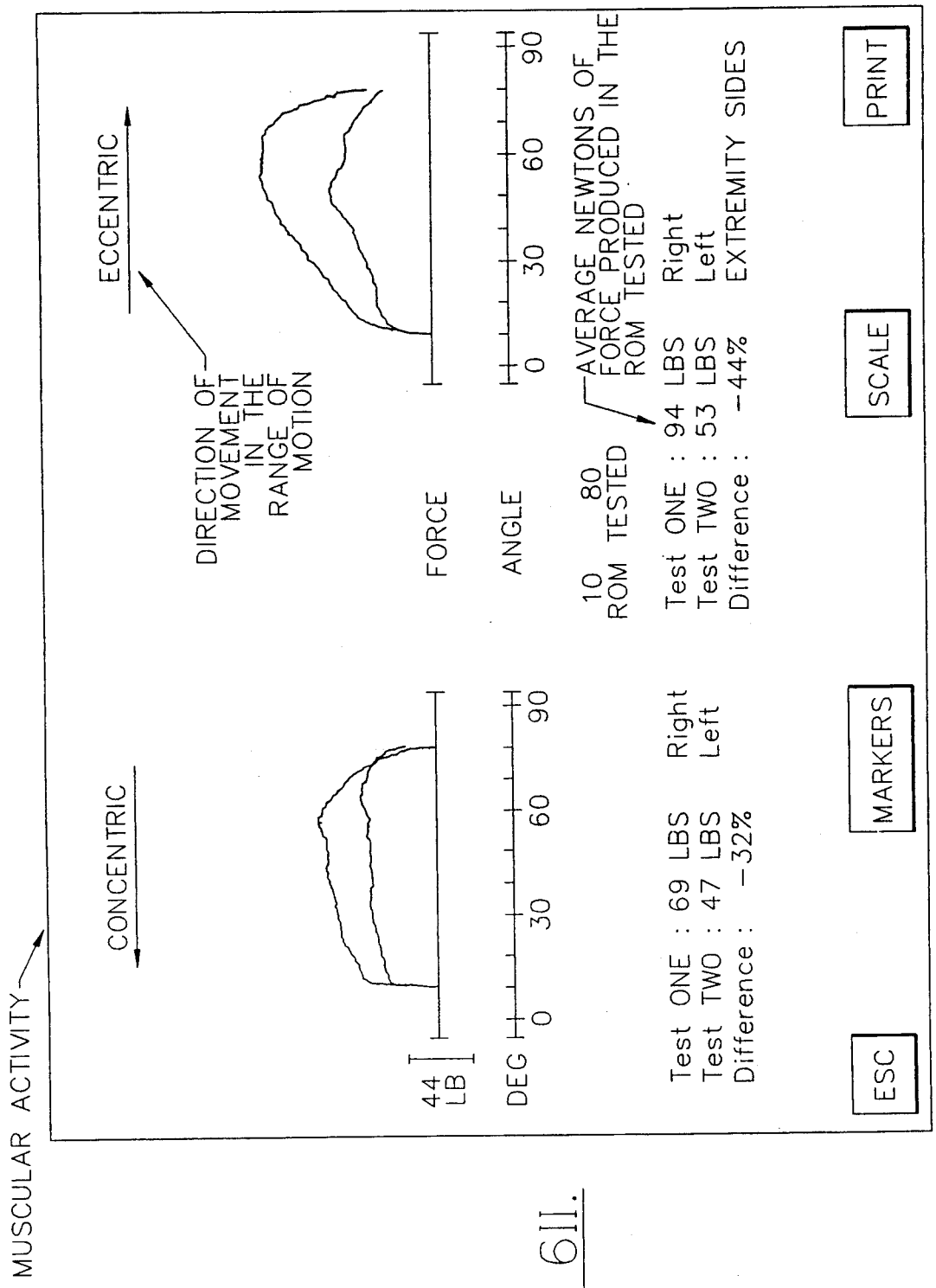
Figure 6J:
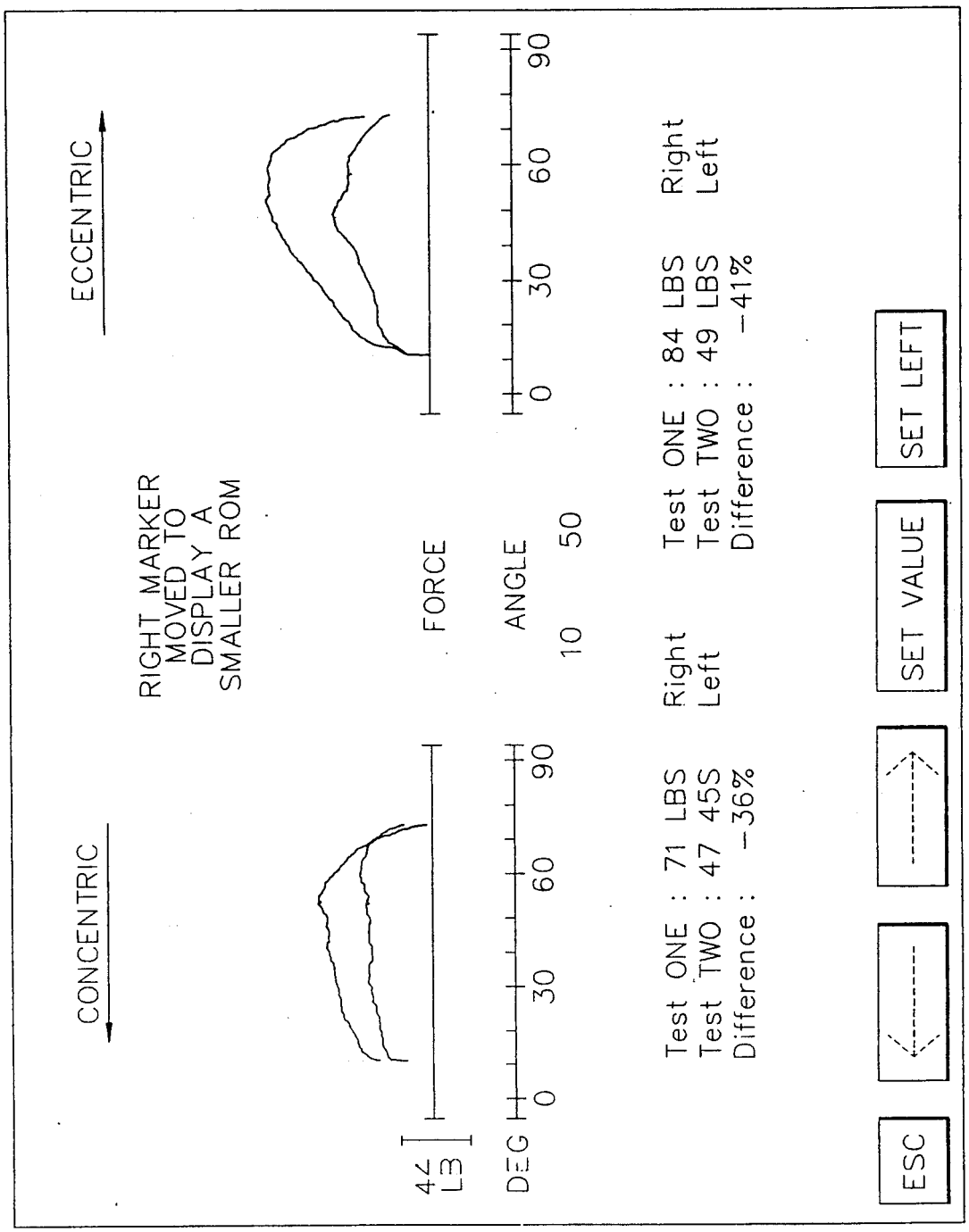
Figure 6M:
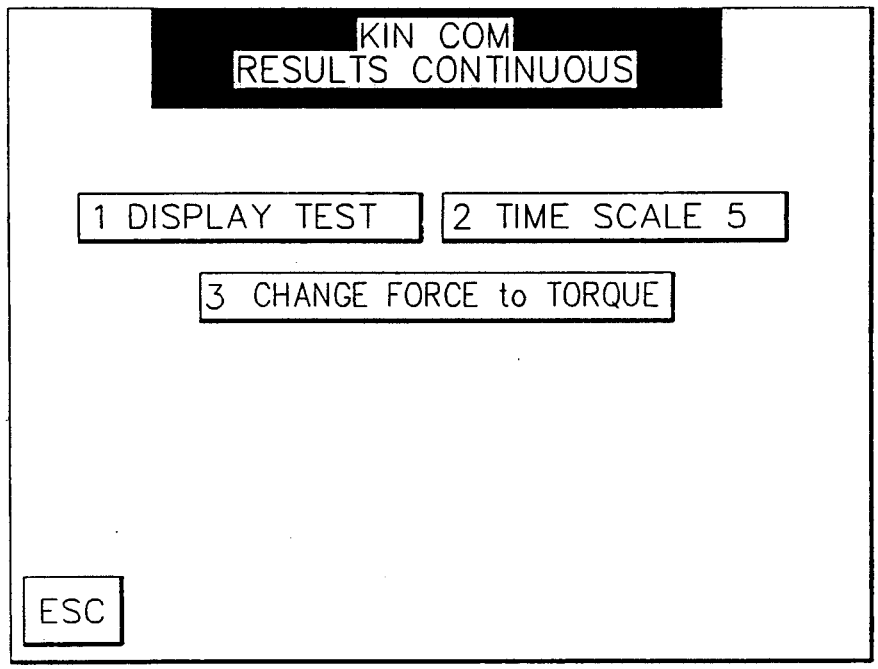
Figure 6N:
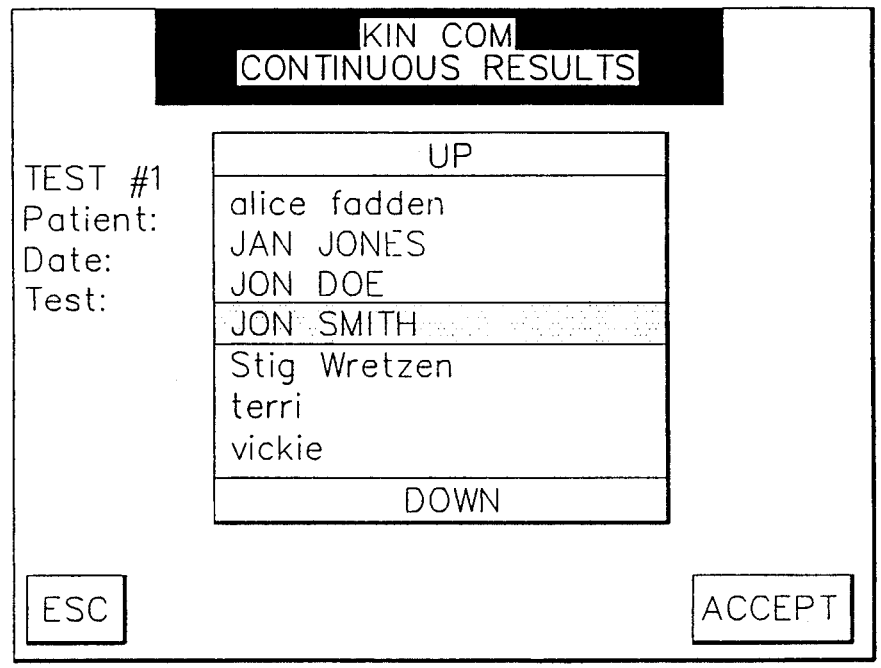
Figure 6Q:
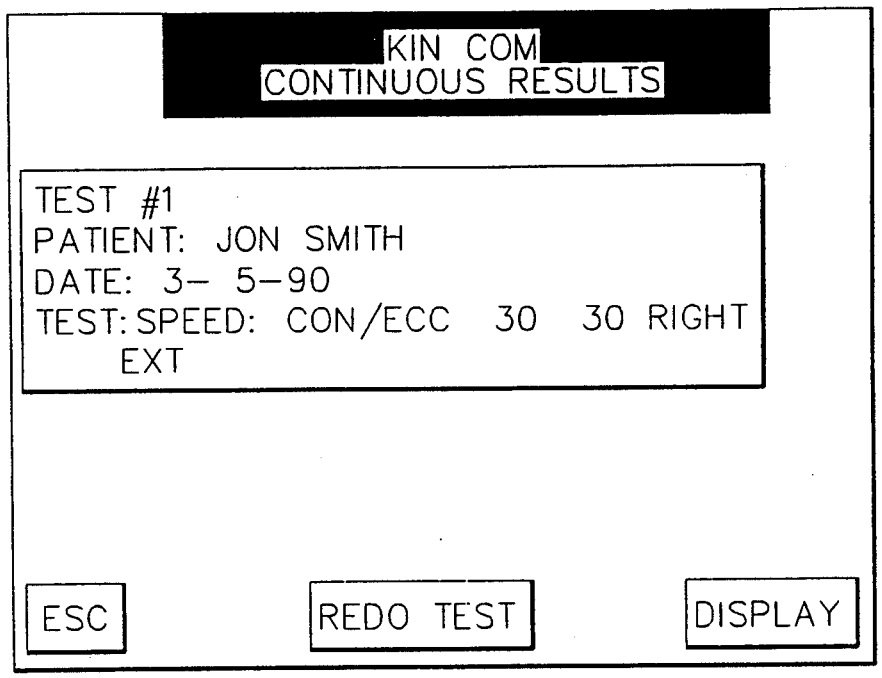
Figure 6R:
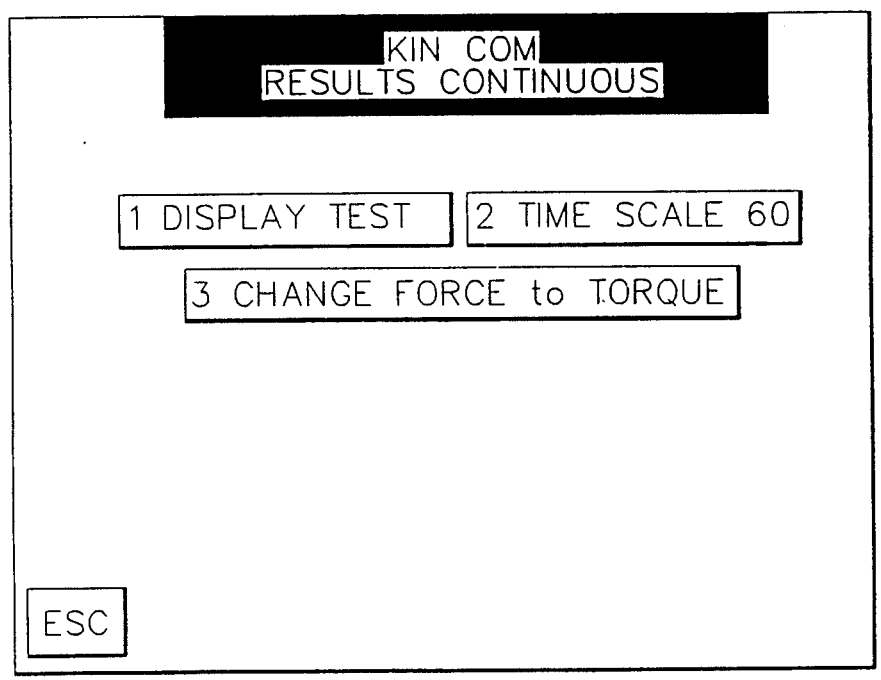
Figures 6S, 6T:
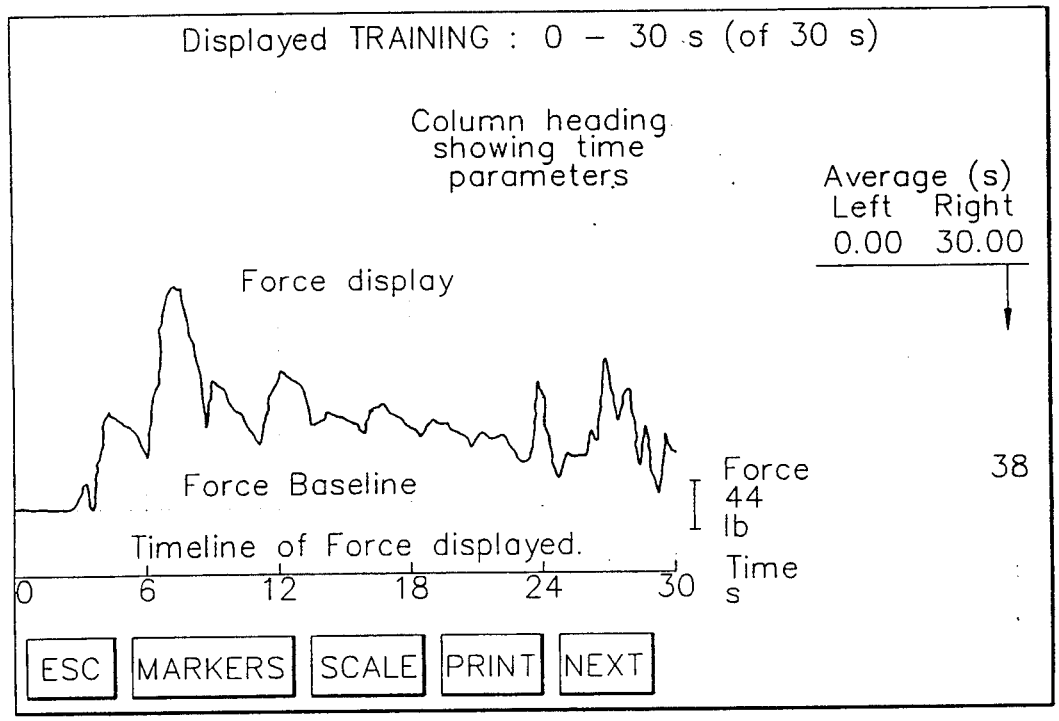
Figures 6U, 6V:
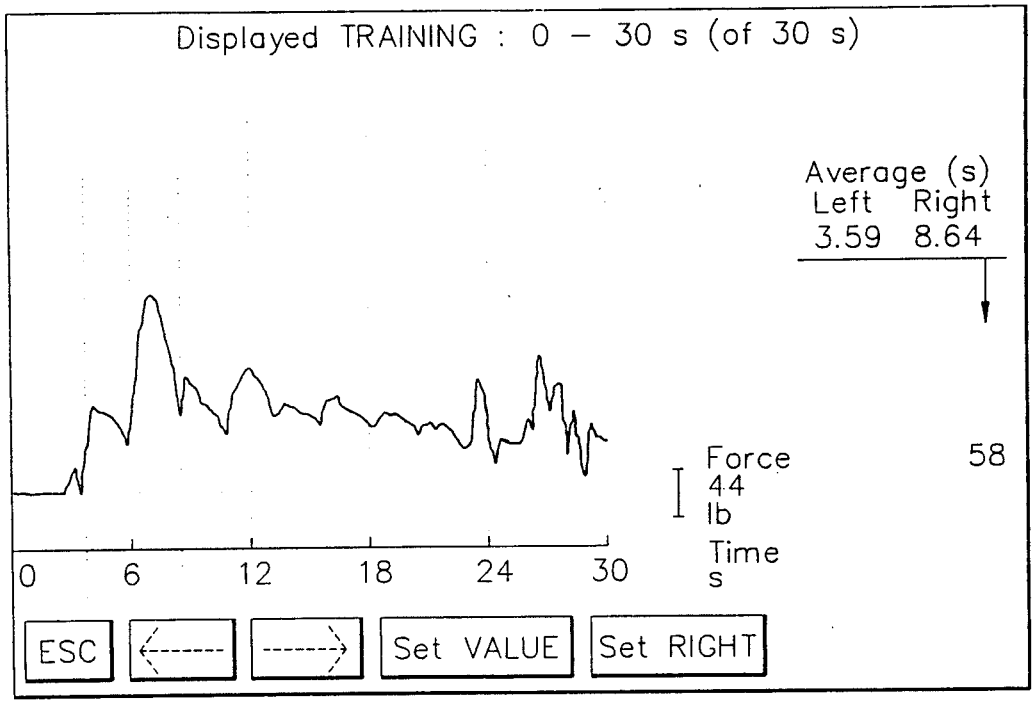
Figure 6W:
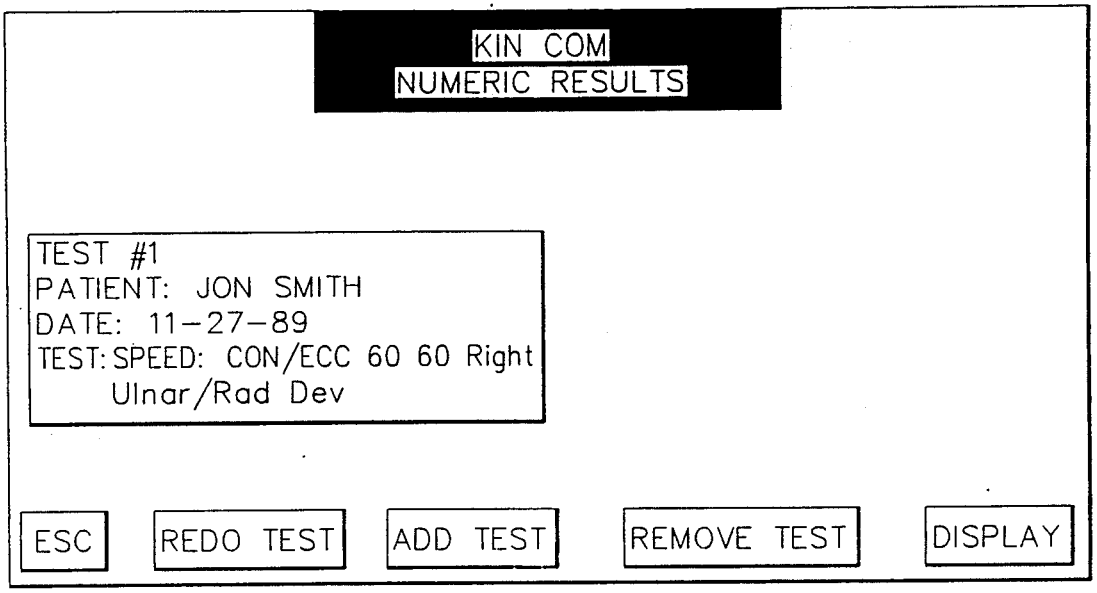
Figure 6X:
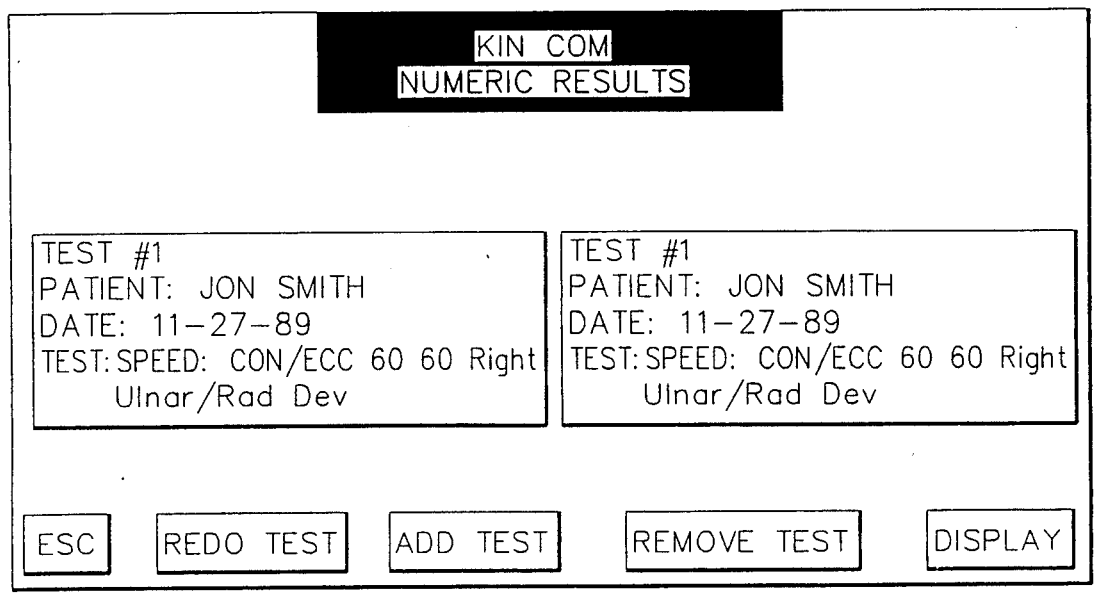

Referring to FIG. 5T, the modification procedure for changing the force parameters associated with an isotonic exercise will now be described. The force parameters and values for an isotonic exercise are displayed at 320 as a result of a determination at 300d in FIG. 5R that the present exercise for which the operator desires to change the force protocol parameters is an isotonic exercise. The force parameters displayed at 320 appear on display 30a as illustrated in FIG. 6Z. Consistent with the touch screen interface, the operator makes a selection of a parameter to be changed or the ESCape or RETURN TO EXERCISE option at 321 by making an indication on the touch screen at the appropriate location.

As indicated generally by 322, a multiple sequential decision block illustrates the decision process by the computer controller in deciding which of the force parameters the operator is changing or whether the ESCape or RETURN OPTION was selected. Based upon a determination at 322a that the FORCE FORWARD parameter was selected to be changed, at 322b that the FORCE BACKWARD parameter was selected to be changed, or at 322c that the MINIMUM FORCE parameter was selected to be changed, the new value for the selected parameter is entered at 323 via the touch calculator located on the right side of the display as illustrated in FIG. 6Z. Control is transferred to transition Block F_IST provided for ease of illustration to indicate that the display will continue to be displayed on the monitor containing the new value for the parameter which was changed until another parameter is selected for modification or one of the ESCape or RETURN TO EXERCISE options are selected.

Based upon a determination at 322d that the operator selected the ESCape option, control is transferred to transition Block B1 resulting in display at 290 in FIG. 5Q of the protocol parameters which the operator can change during the exercise. These protocol parameters are illustrated in FIG. 6U. Finally, a determination is made at 322e whether the operator selected the RETURN TO EXERCISE option. If the RETURN TO EXERCISE option was selected, control is returned to the present isotonic exercise whereby the patient continues the exercise or evaluation process on the exercise machine as controlled by the computer controller based upon the protocol parameters in light of any changes made by the operator to the values of those parameters. If none of the parameters have been selected or changed nor the options selected by the operator, the system remains in its present state as indicated by transition Block IF_4 resulting in continued display of the force parameters associated with an isotonic exercise which may be changed by the operator until one or more of the force parameters are modified or one of the ESCape or RETURN TO EXERCISE options is selected.

Figure 5U:
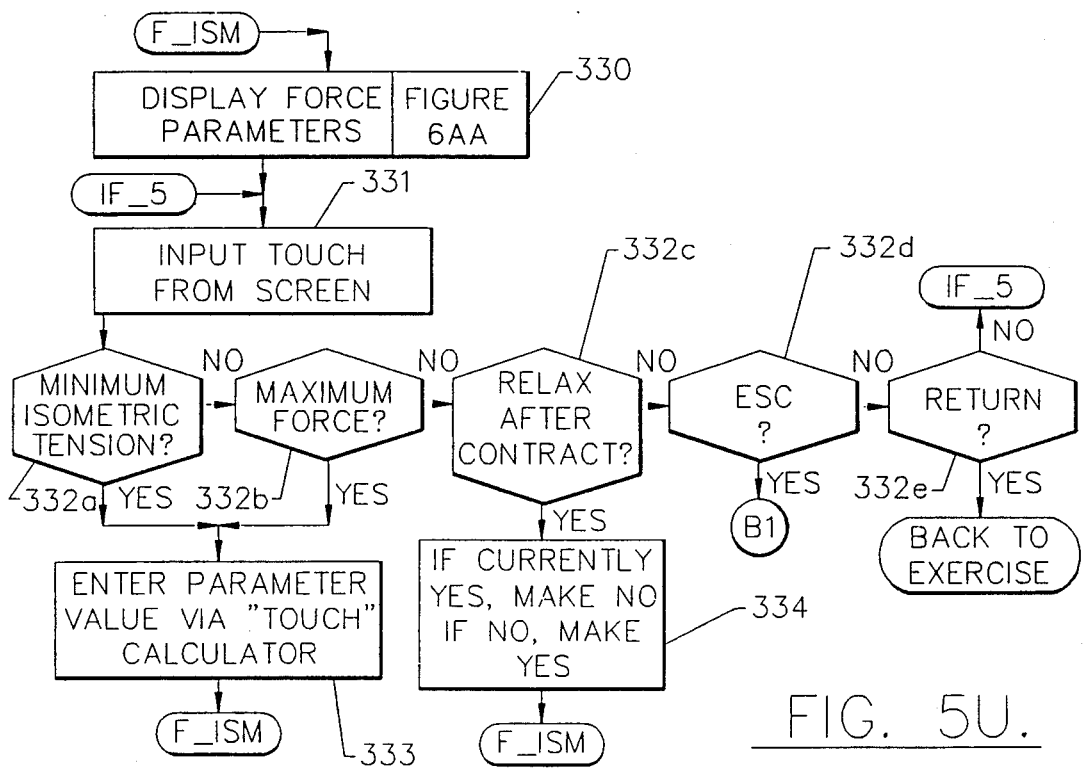

Referring to FIG. 5U, the control flow of the process for changing the force parameters associated with an isometric exercise will now be described. Based upon a determination at 300c of FIG. 5R that the present exercise is an isometric exercise and a desire by the operator to change the force parameters, the force parameters associated with the present isometric exercise will be displayed at 330. These force parameters and their values are displayed to the operator on the display portion of monitor 30 as illustrated in FIG. 6AA. Consistent with the touch screen interface, the operator selects the parameter to be changed or the ESCape or RETURN TO EXERCISE option at 331 by making the appropriate indication on the touch screen. A multiple sequential decision block is provided at 332 generally to illustrate the determination of which option was selected. Based upon a determination at 332a that the operator selected the MINIMUM ISOMETRIC TENSION to be changed or at 332b the operator selected the MAXIMUM FORCE parameter to be changed, the new value for the selected parameter is entered at 333 via the touch calculator located on the right side of the display as illustrated in FIG. 6AA. Once the new value for the parameter has been entered, the new value is indicated on the display at 330 after which the operator can select another parameter to be changed or select the ESCape or RETURN TO EXERCISE option.

Based upon a determination at 332c that the operator desired to change the for RELAX AFTER CONTRACTION, the parameter's value is changed at 334. The RELAX AFTER CONTRACTION parameter is a toggle or flip-flop parameter whereby a value of "yes" is changed to "no" or a value of "no" is changed to "yes" at 334. This results in the display showing the new value for the RELAX AFTER CONTRACTION parameter and continued display at 330 of the force parameters from isometric exercise. The operator then can select one or more of the parameters to be changed or the ESCape or the RETURN TO EXERCISE option.

Based upon a determination at 332d that the ESCape option was selected, control is returned to transition Block B1 resulting in display of the protocol parameters at 290 of FIG. 5Q which the operator can change. Finally, a determination is made at 332e whether the operator selected the RETURN TO EXERCISE option. If the RETURN TO EXERCISE option was selected, control is returned to the exercise to permit the patient to continue the training or evaluation process on the muscle exercise machine as controlled by the computer controller based upon the parameters associated with the protocol including any new values for the parameters set by the operator. If none of the force parameters associated with the isometric exercise were selected or changed and neither the ESCape or RETURN TO EXERCISE options were selected, the computer controller waits, continuing to display the parameters as illustrated in FIG. 6AA until the operator selects one or more of the parameters to be changed or either the ESCape or RETURN TO EXERCISE option.

Figure 5V:
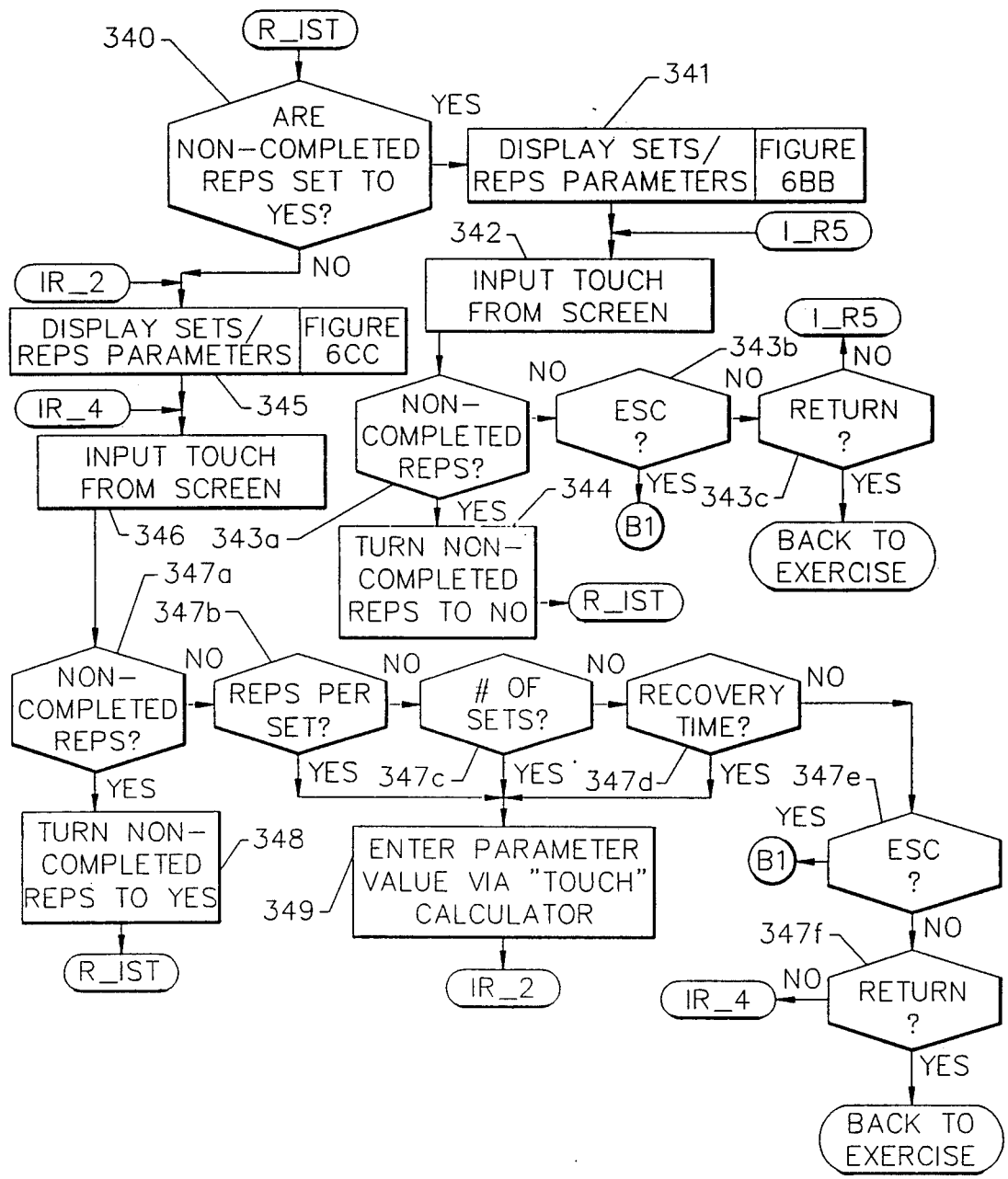

Referring to FIG. 5V, the control flow for changing the sets and repetition parameters associated with an isotonic exercise will now be described. Based upon a determination at 310c in FIG. 5S that the present exercise is an isotonic exercise and that the operator desired to change the values of the sets and repetition parameters, a decision is made at 340 as to whether NONCOMPLETED REPETITIONS is set to "yes". If NONCOMPLETED REPETITIONS is set to "yes", the computer controller does not count repetitions and the patient does not have to perform "complete" repetitions, i.e. proceed the entire distance back and forth from the start angle to the stop angle.

If the NONCOMPLETED REPETITIONS flag is set to "yes", the sets and repetition parameters limited only to the NONCOMPLETED REPETITION flag are displayed at 341 as illustrated in FIG. 6BB. Consistent with the touch screen interface, the operator can select either to change the NONCOMPLETED REPETITIONS parameter or the ESCape or RETURN TO EXERCISE options at 342 by indicating at the appropriate location on the touch screen. A determination is made at 343a whether the NONCOMPLETED REPETITION parameter was selected to be changed by the operator. If the NONCOMPLETED REPETITIONS parameter was selected by the operator to be changed, the value of the parameter is toggled at 344 resulting in switching of the value from "yes" to "no". Control is transferred to transition Block R_IST provided for ease of illustration to indicate that a query is made at 340 whether the NONCOMPLETED REPETITIONS parameter is set to "yes".

Based upon a determination at 343b that the operator selected the ESCape option, control is transferred to transition Block B1. This results in the display of the protocol parameters at 290 in FIG. 5Q which the operator can change. Finally, a determination is made at 343c whether the operator selected the RETURN TO EX- ERCISE option. If the RETURN TO EXERCISE option was selected by the operator, control is transferred back to the exercise from which the CHANGE BOX processing received control permitting the patient to continue training or evaluation on the exercise machine as controlled by the computer controller based on the protocol and any new values for protocol parameters. If the parameter to be changed or the ESCape or RETURN TO EXERCISE options were not selected, the system remains in its present state as indicated by transition Block IR_5 until the operator indicates a desire to change the NONCOMPLETED REPETITIONS parameter or selects the ESCape or RETURN TO EXERCISE option.

Based upon a conclusion at 340 that the noncompleted repetitions parameter is not set to "yes", i.e. is set to "no", the sets and repetition parameters are displayed at 345 as illustrated in FIG. 6CC. If NONCOMPLETED REPETITIONS is set to "no", the patient must complete each repetition before starting the next repetition, i.e. changing directions. In other words, the patient must move the exercise element the entire distance from the start angle to the stop angle. Since the noncompleted repetitions parameter is set to no, all the reps and sets parameters are displayed. Consistent with the touch screen interface, the operator can indicate the parameter to be changed or the option to be selected at 346 by touching the appropriate location on the touch screen. A determination is made as to which parameter the operator has selected to change. This determination is performed sequentially as illustrated generally at 347 by the multiple sequential decision blocks. Based upon a conclusion at 347a that the operator selected the NONCOMPLETED REPETITIONS parameter to be changed, the value of the noncompleted repetitions parameter will be toggled from "no" to "yes" at 348. Control is then transferred to transition Block R_IST resulting in the query at 340 as to whether the noncompleted repetitions parameter is set to yes.

Based upon a determination at 347b that the REPETITIONS PER SET parameter was selected, at 347c that the NUMBER OF SETS parameter was selected or at 347d that the RECOVERY TIME parameter was selected, the new value for the parameter chosen to be changed is entered at 349 via the touch calculator located on the right side of the display as illustrated in FIG. 6CC. Control is then transferred to transition Block IR_2 resulting in continual display at 345 of the sets and repetition parameters containing any change in values made to permit further parameter value changes or selection of the ESCape or RETURN TO EXERCISE option.

Based upon a determination at 347e that the ESCape option was selected, control is transferred to transition Block B1. This results in the display at 290 in FIG. 5Q of the protocol parameters which the operator can choose to change or modify. Finally, a determination is made at 347f whether the operator indicated a desire to return to the exercise. If the RETURN TO EXERCISE option was selected, control is returned back to the exercise from which the CHANGE BOX processing and ultimately the change set up processing received control. Thus, the patient can continue training or evaluation exercising on the muscle exercising machine as controlled by the computer controller based upon the parameters and any new values designated by the operator. If none of the parameters were selected for change and neither the ESCape or RETURN TO EXERCISE option was selected, the computer controller remains in its present state and continues to display the sets and reps parameters at 345 until the parameters are selected for change or one of the ESCape or RETURN TO EXERCISE options is selected.

Figure 5W:
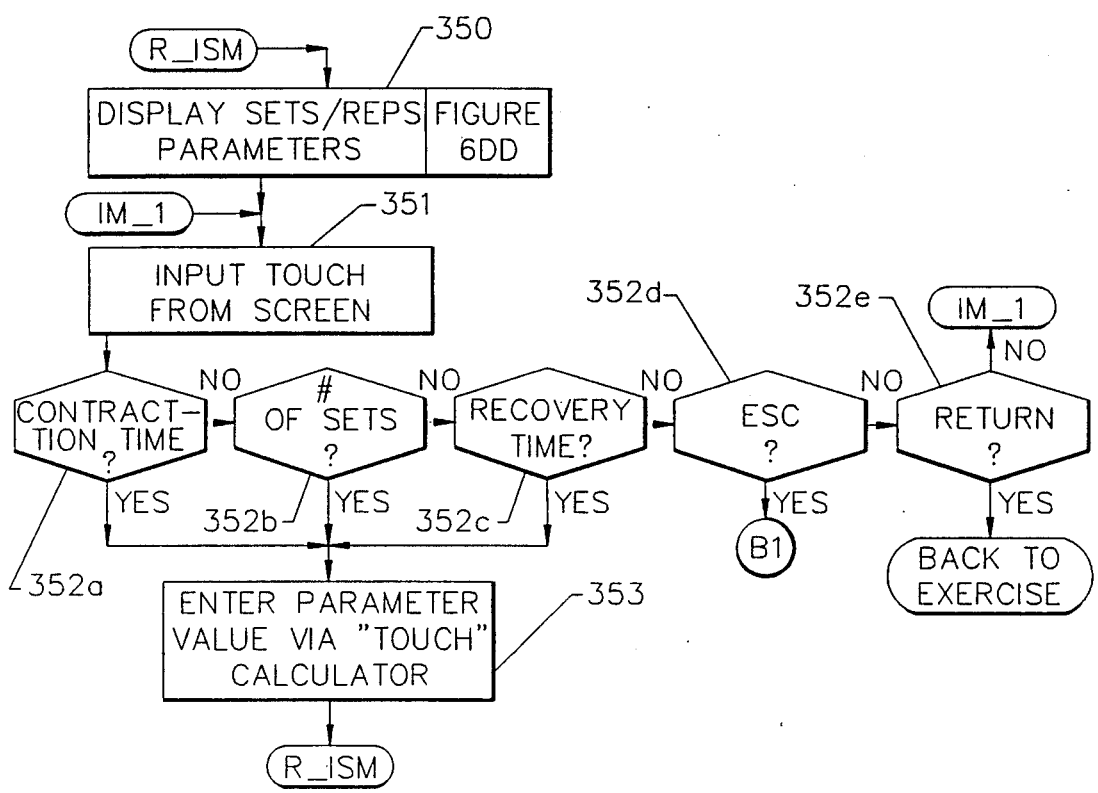

Referring to FIG. 5W, the control flow for operator change of the sets and repetition parameters associated with an isometric exercise will now be described. As a result of a determination at 310b of FIG. 5S that the present exercise is an isometric exercise and a desire by the operator to change the values of the sets and repetition parameters, the sets and reps parameters will be displayed at 350 as illustrated in FIG. 6DD. Consistent with the touch screen interface, input from the touch screen is made at 351 by the operator as a result of an indication on the touch screen at the appropriate location for the parameter or option selected. If one of the sets and reps parameters was selected to be changed, the new value is entered at 353 via the touch calculator located on the right side of the display as illustrated in FIG. 6DD. Control is then transferred to transition Block R_ISM provided for illustration purposes to indicate that the sets and reps parameters continue to be displayed containing any new values set by the operator until the operator selects a parameter to be changed or one of the ESCape or RETURN TO EXERCISE options. More specifically, based upon a determination at 352a that the CONTRACTION TIME was selected to be changed, at 352b that the NUMBER OF SETS was selected to be changed, or at 352c that the RECOVERY TIME was selected to be changed, the operator can enter the new value at 353 via the touch calculator.

Based upon a determination at 352d that the ESCape option was selected by the operator, control is transferred to transition Block B1. This results in display of the protocol parameters at 290 in FIG. 5Q which the operator can change in association with the present exercise. Finally, a determination is made at 352e whether the operator selected the RETURN TO EXERCISE option. If the RETURN TO EXERCISE option was selected, control is transferred back to the exercise which was in progress prior to the selection of the CHANGE SETUP option and ultimately CHANGE BOX processing. This permits the patient to continue training or exercise evaluation on the muscle exercise machine as controlled by the computer controller based on the parameters for the particular protocol incorporating any new values for the parameters selected by the operator. If none of the parameters were selected to be changed, and neither the ESCape nor RETURN TO EXERCISE options selected, the system will remain in its present state and continue to display the sets and reps parameters illustrated in FIG. 6DD until the operator selects a parameter to be changed or one of the ESCape or RETURN TO EXERCISE options.

DETAILED OPERATION: RESULT FORMATTING

Figure 5X:
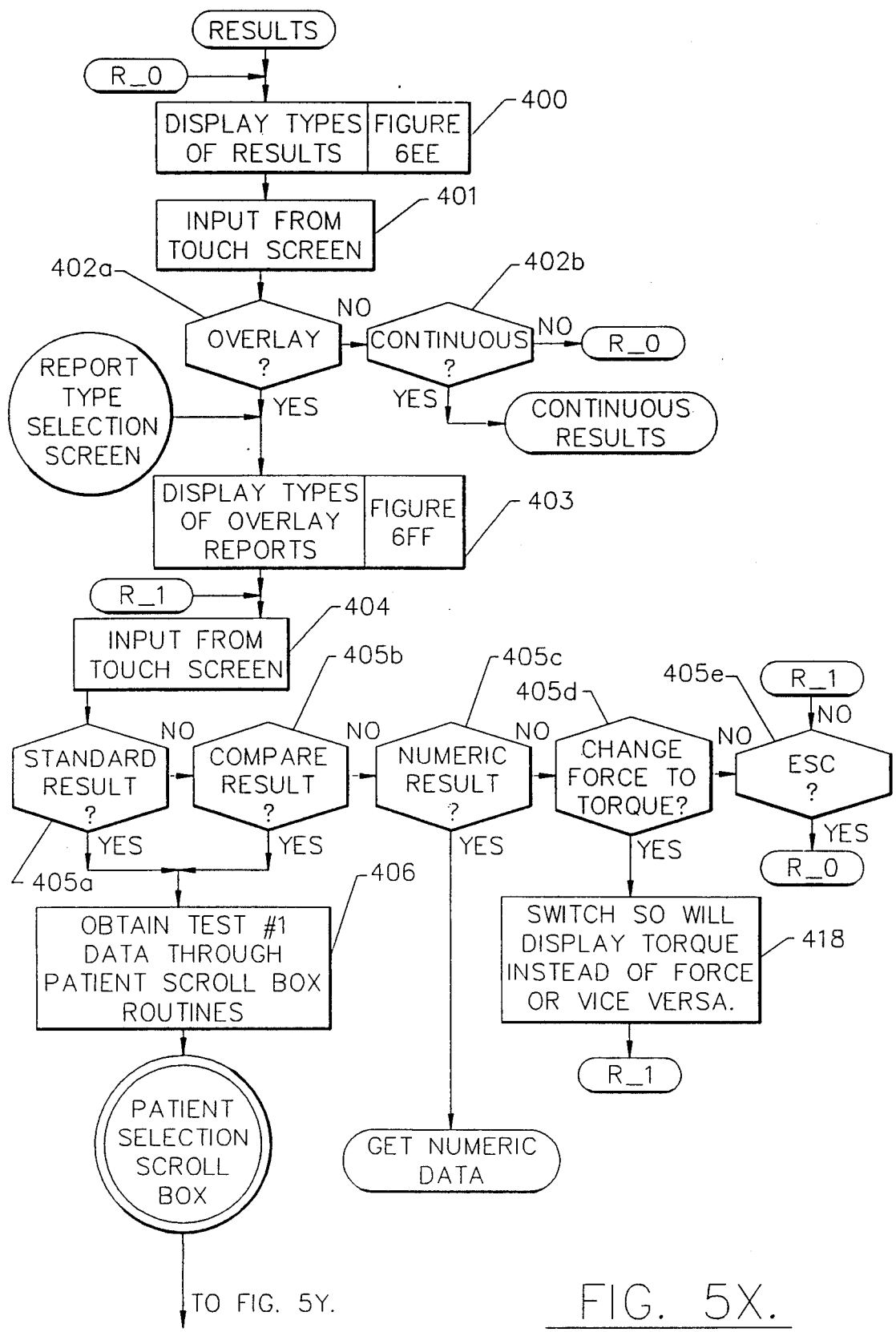
Figure 5Y:
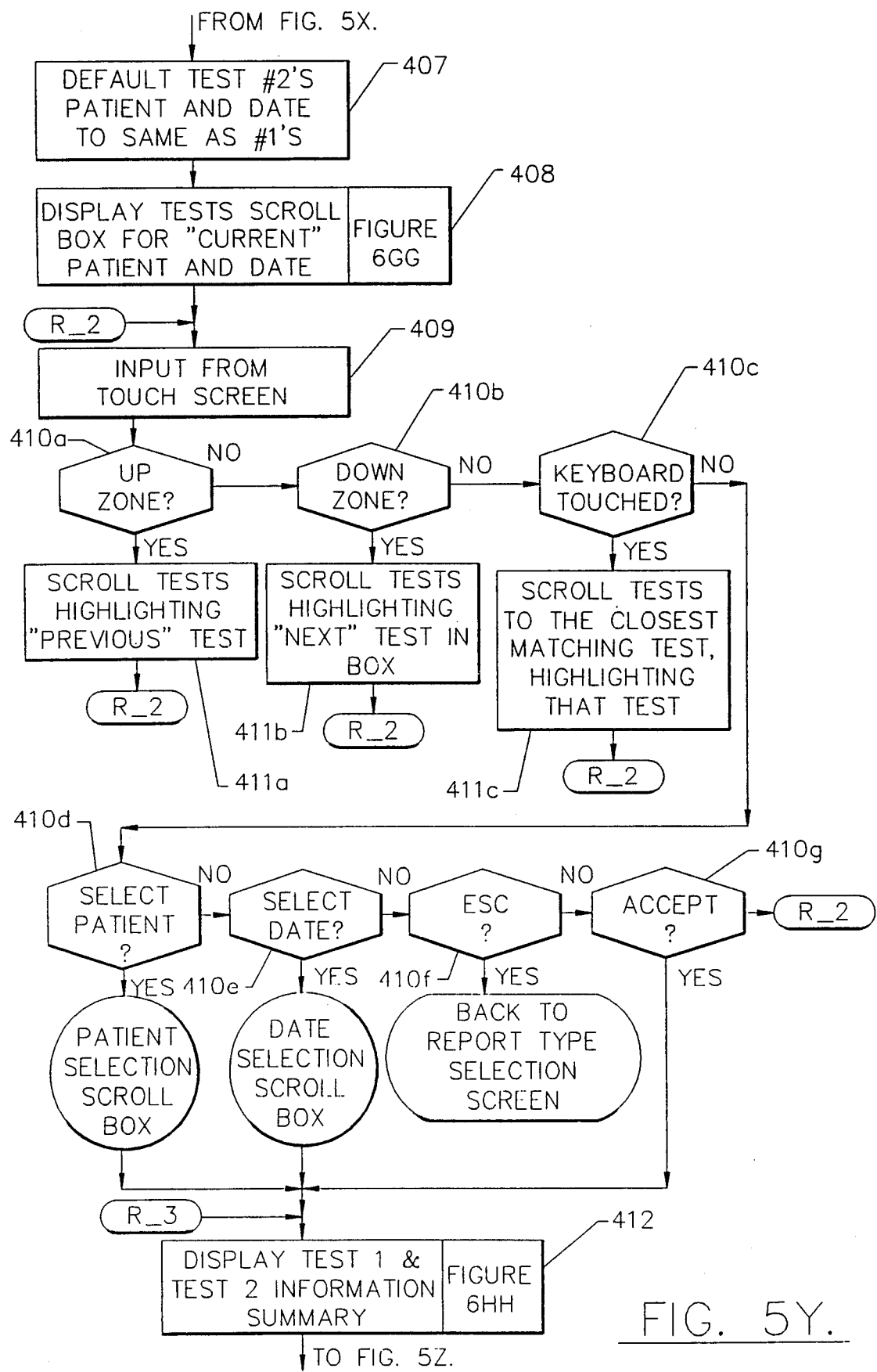
Figure 5Z:
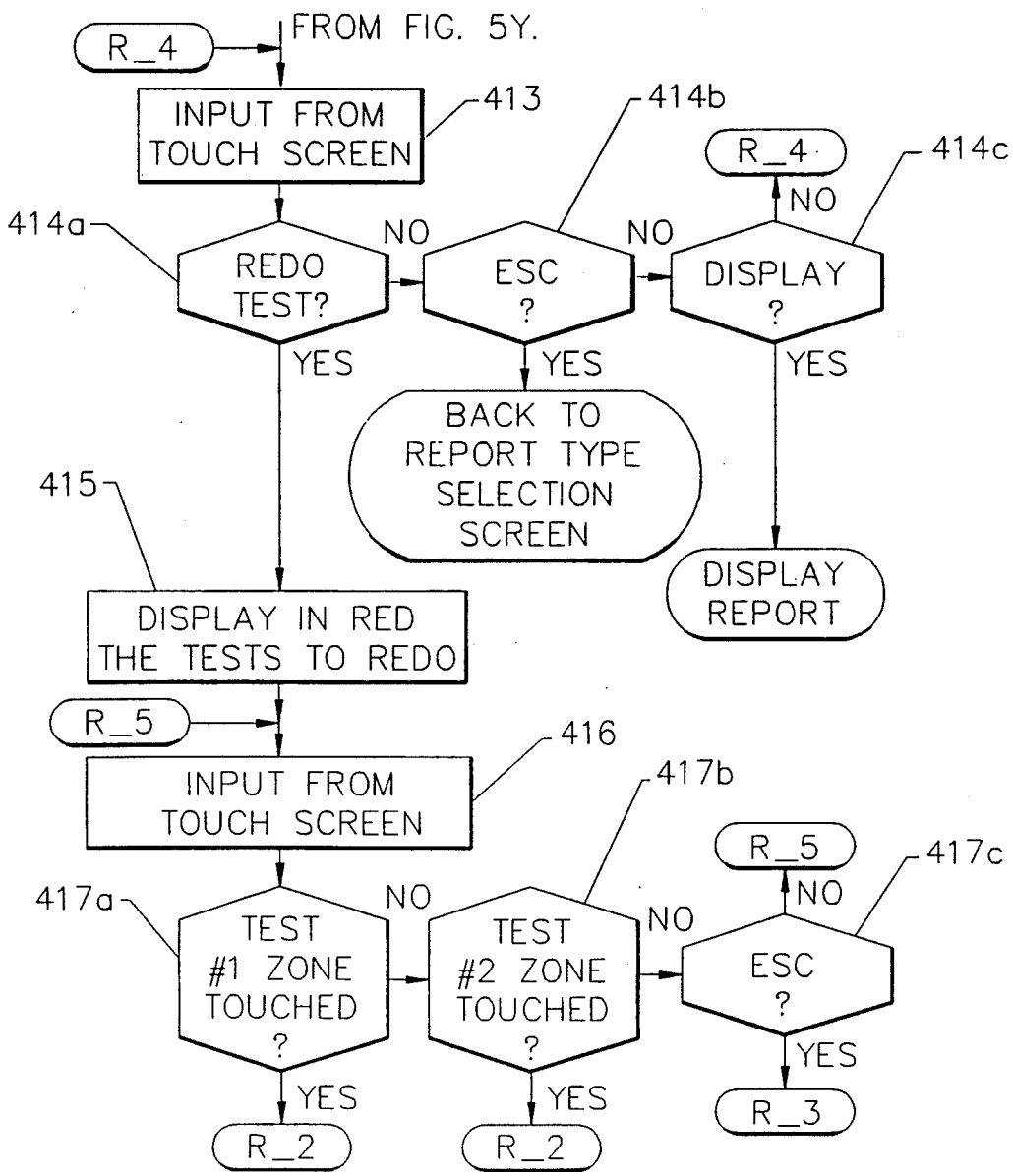
Figure 5A:
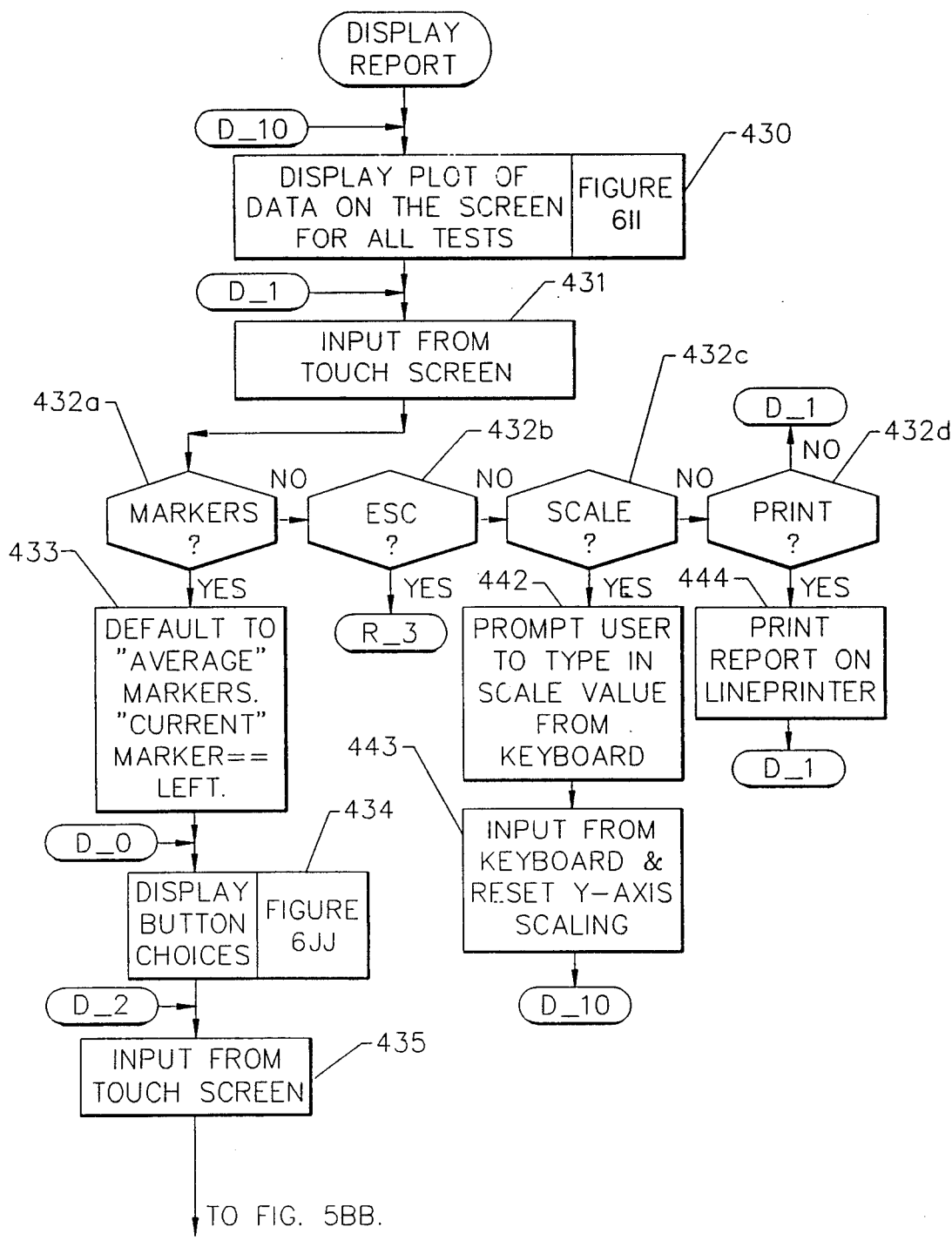
Figure 5B:
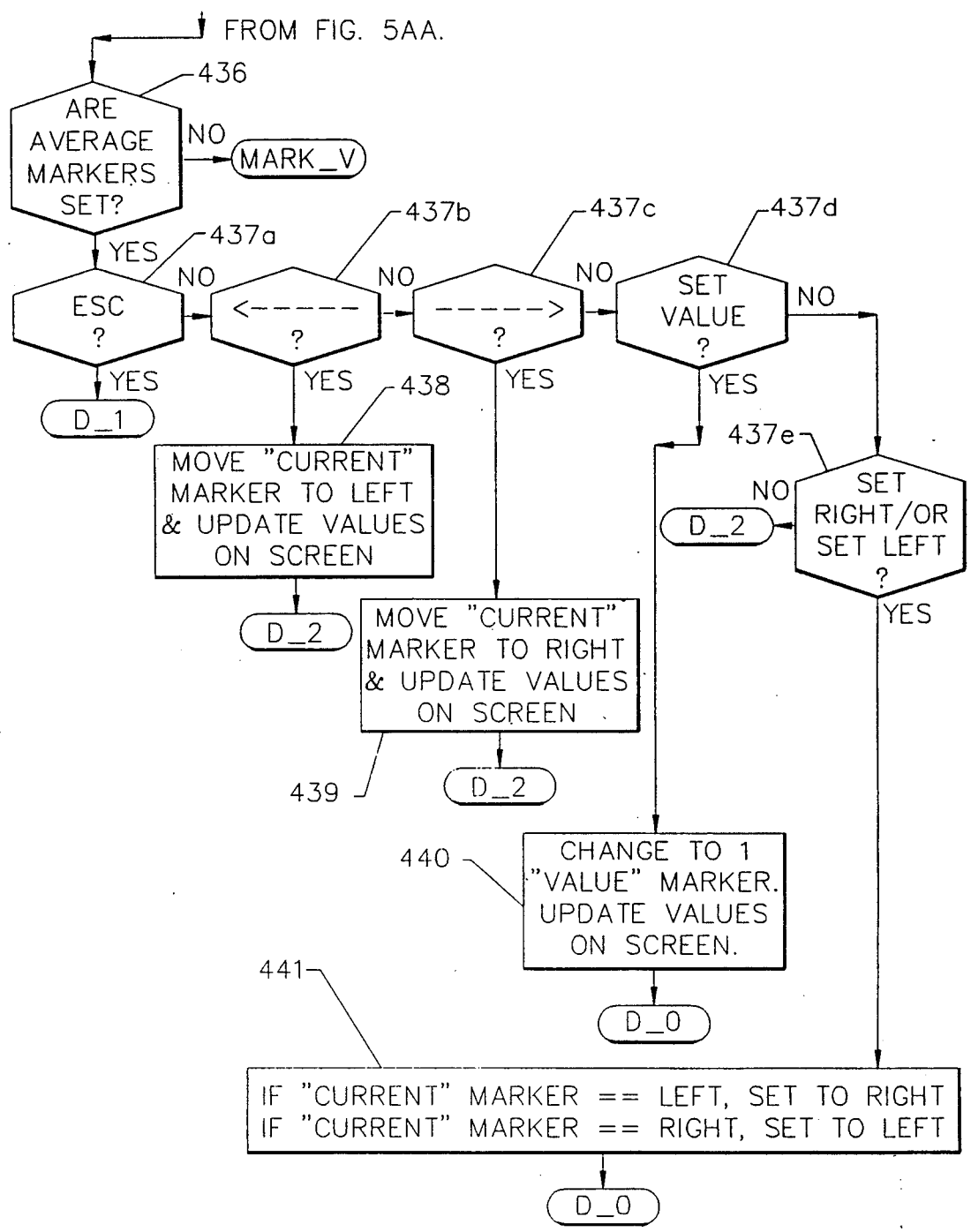
Figure 5C:
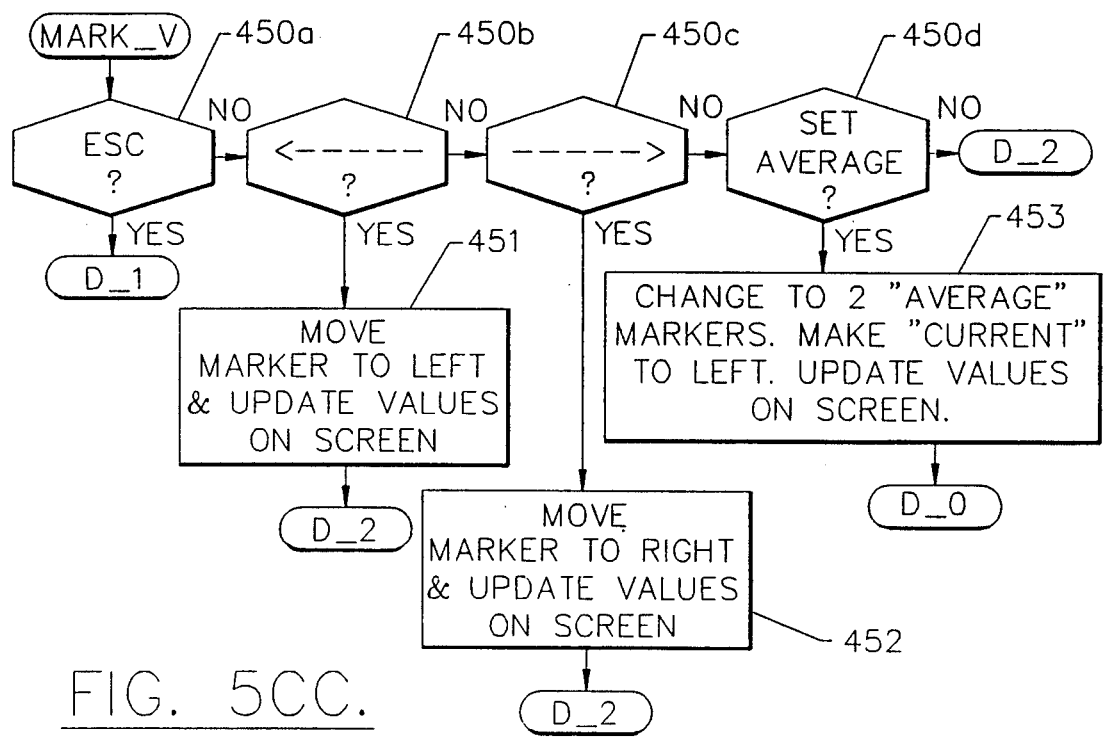
Figure 5D:
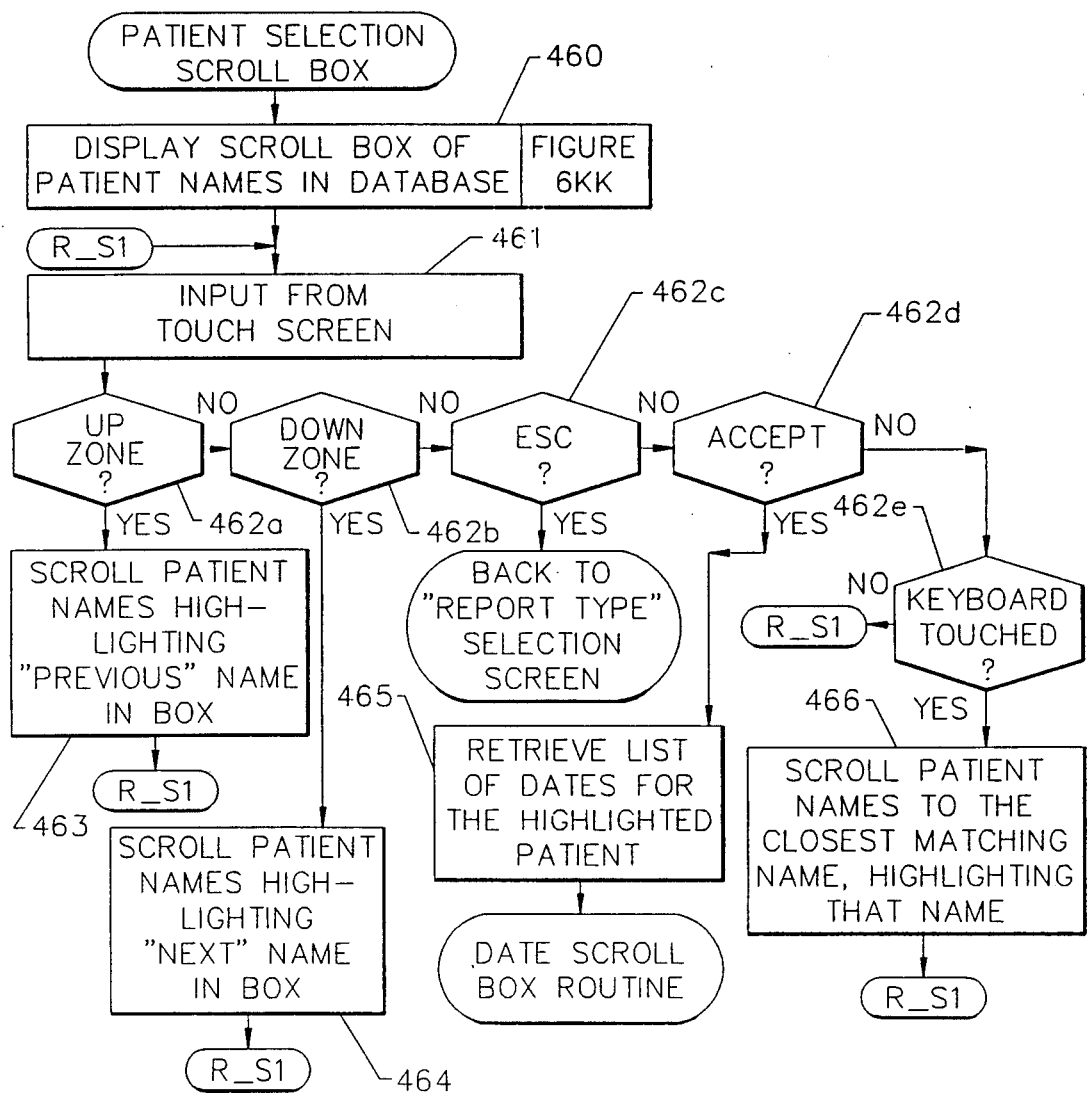
Figure 5E:
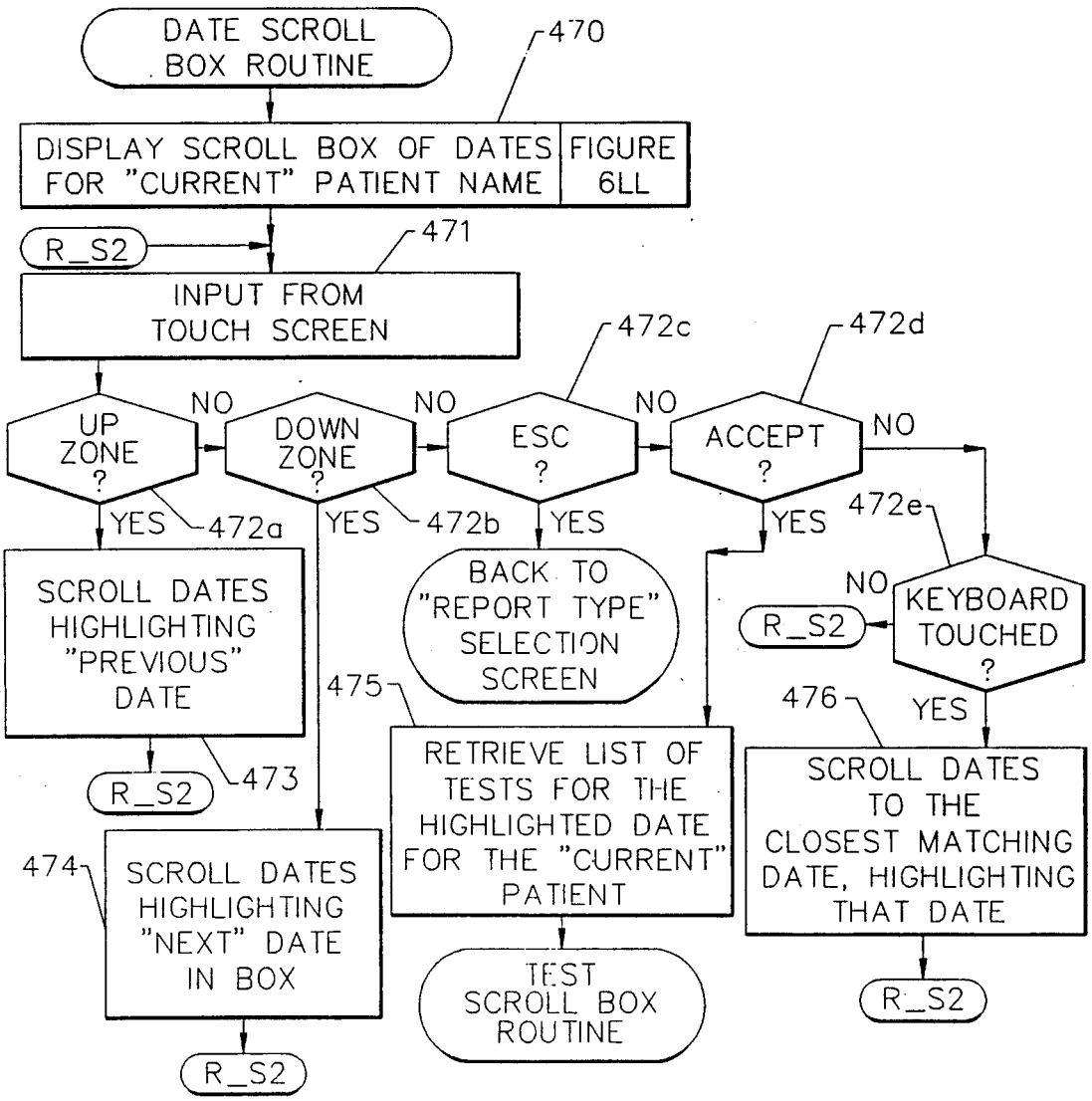
Figure 5F:
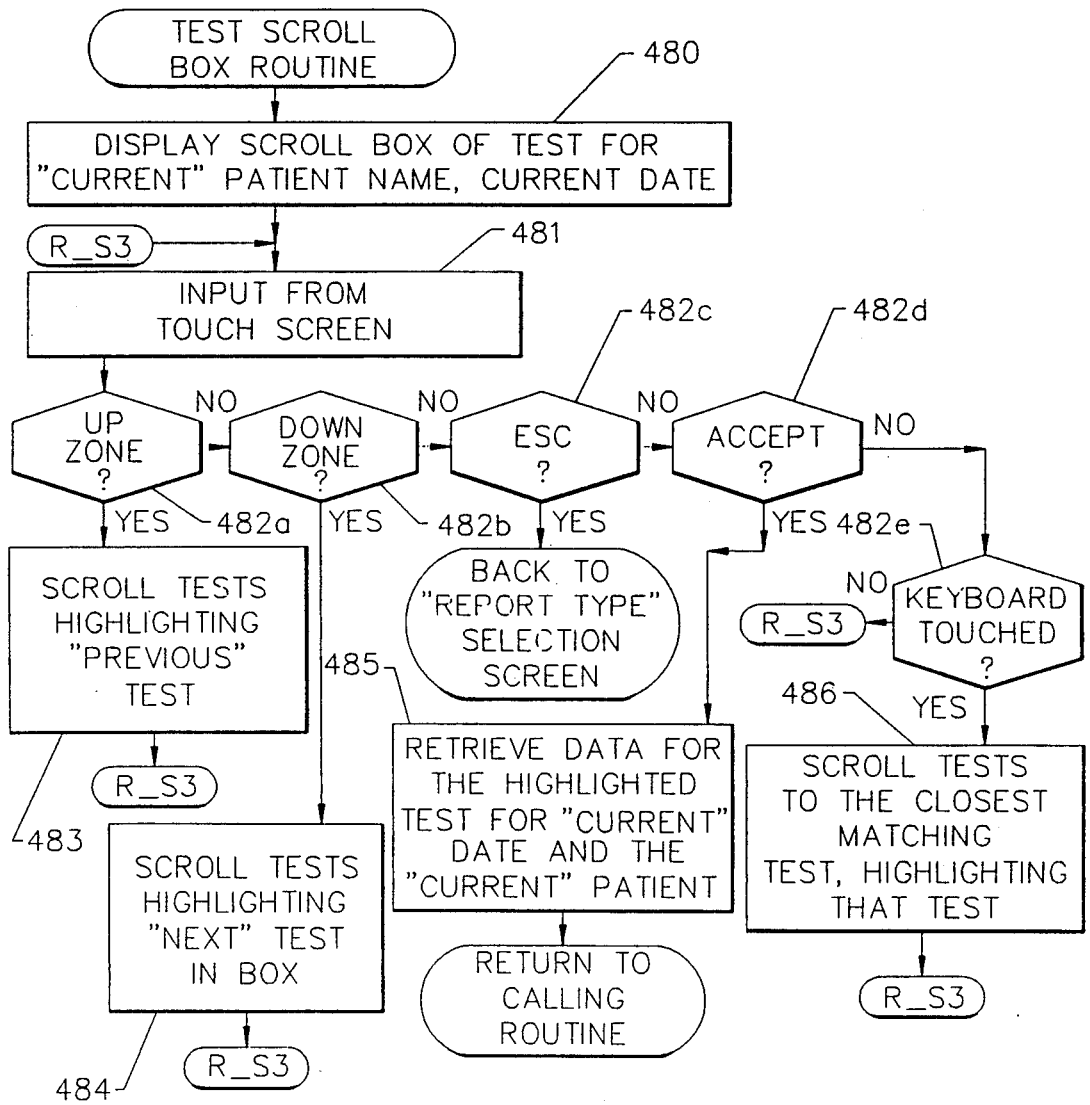
Figure 5G:
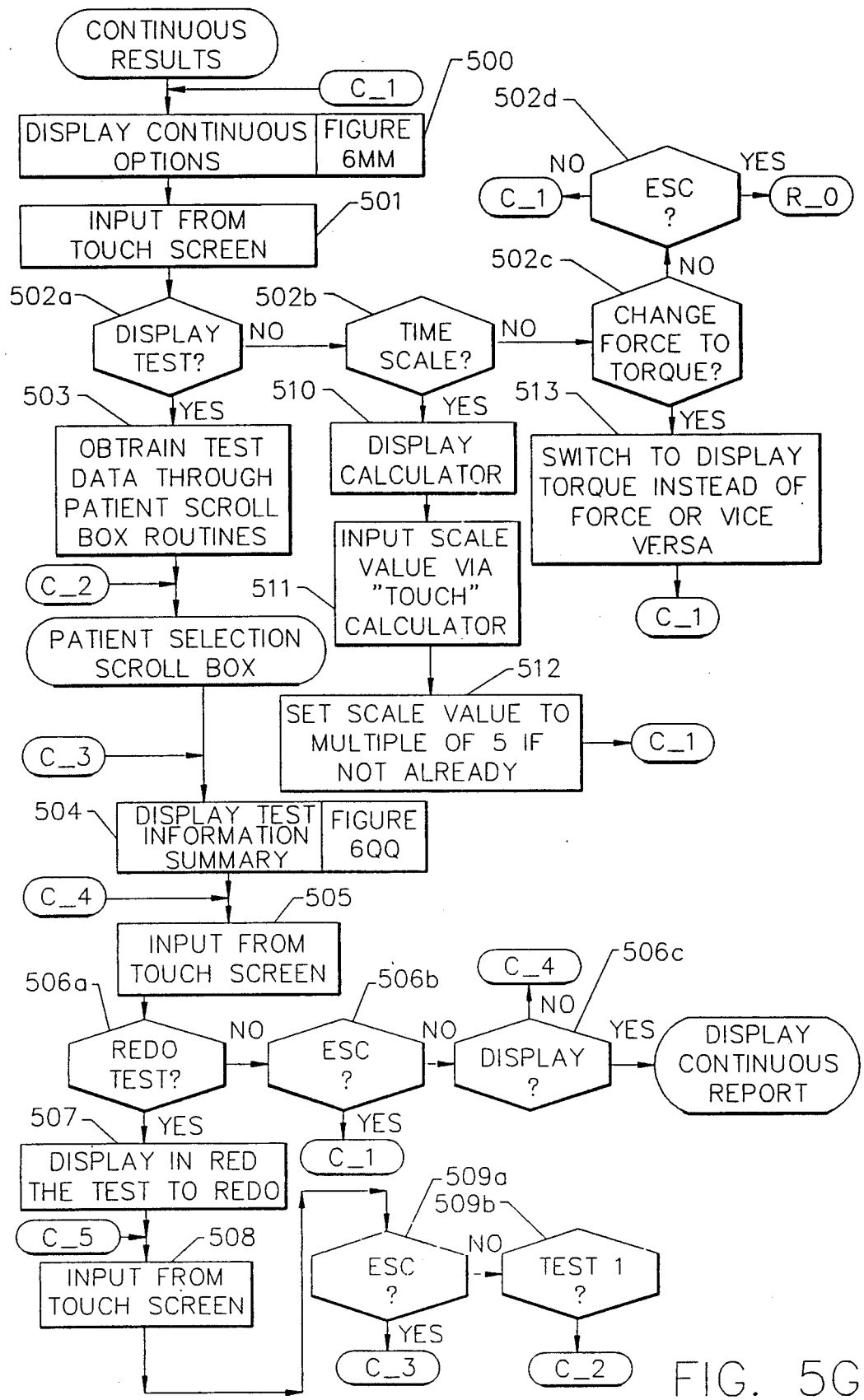
Figure 5H:
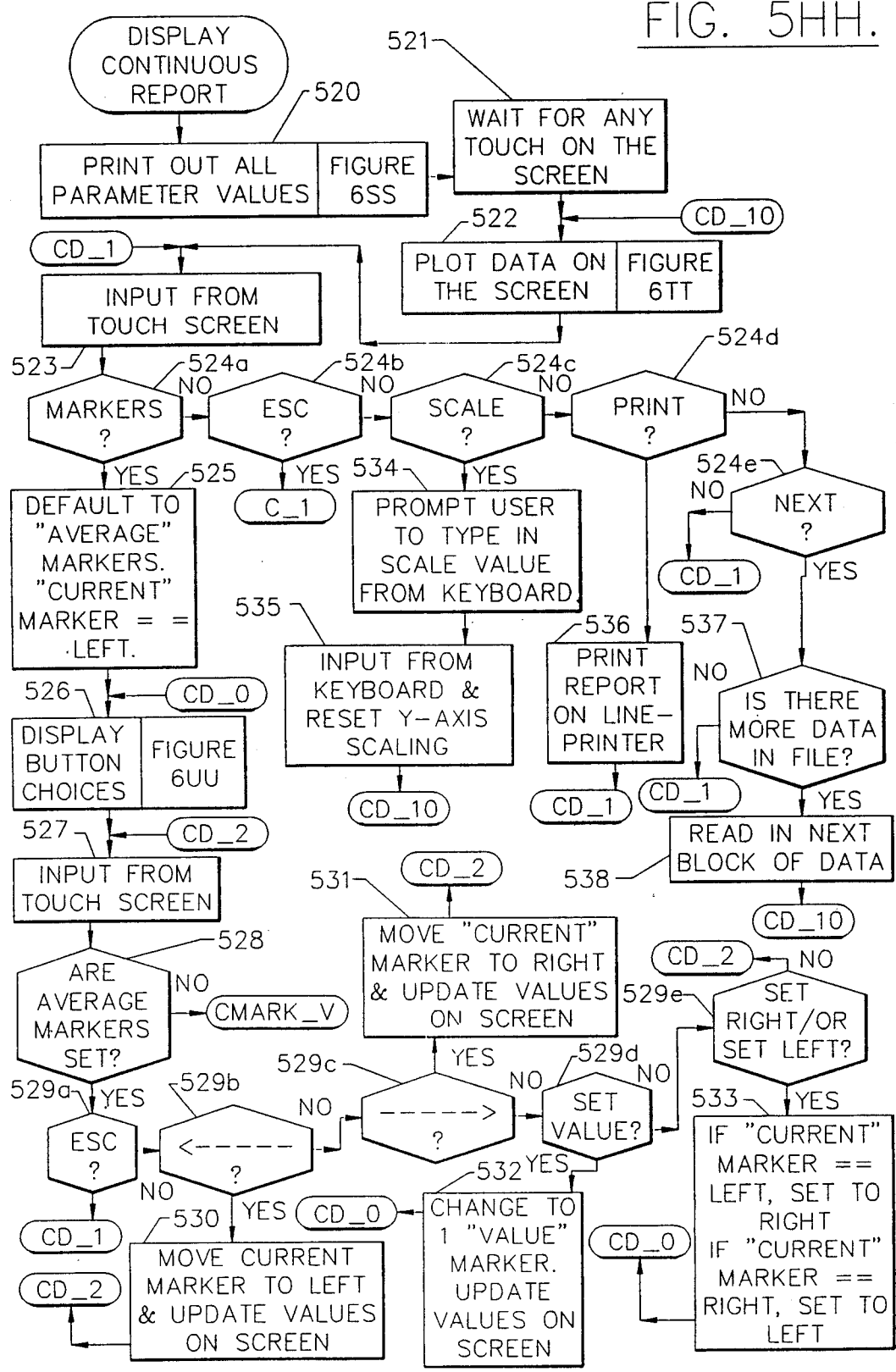
Figure 5I:
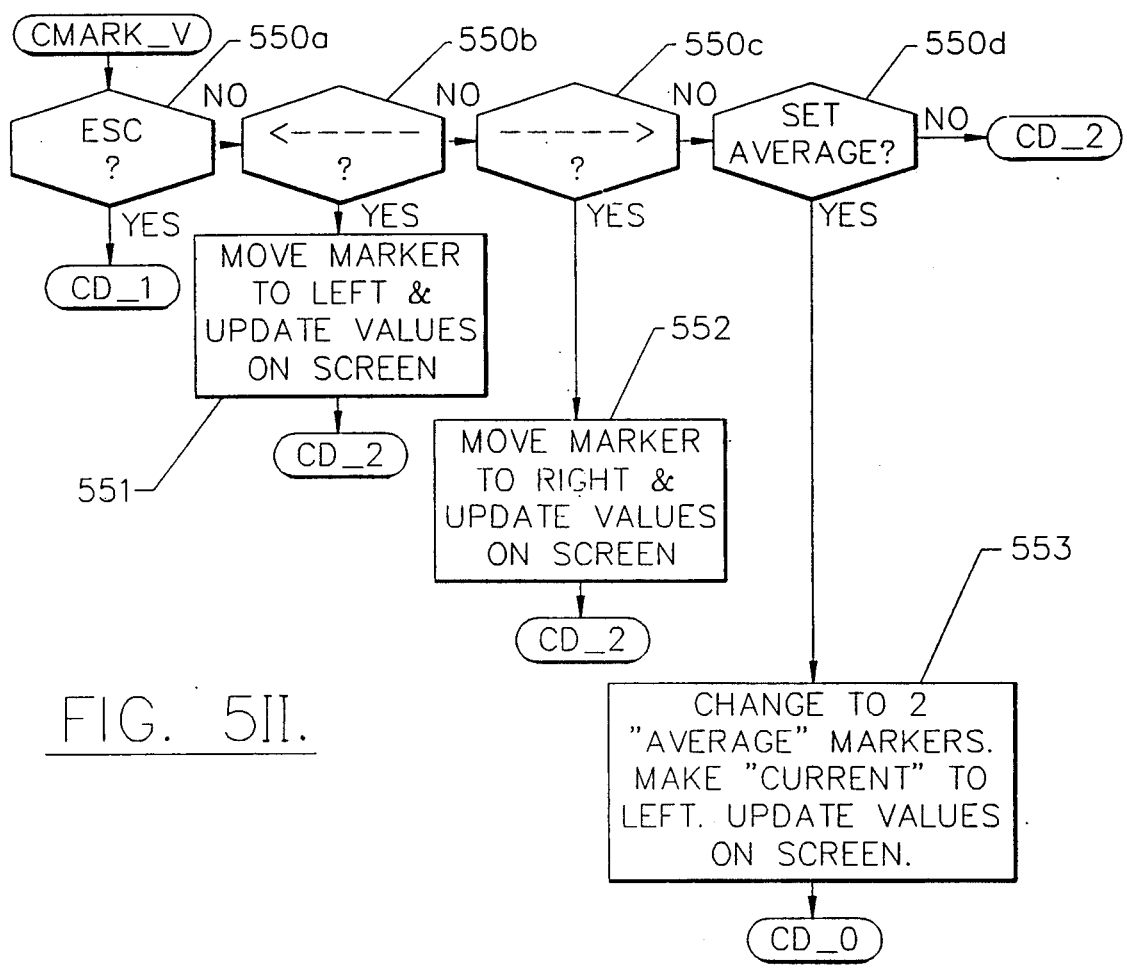
Figure 5J:
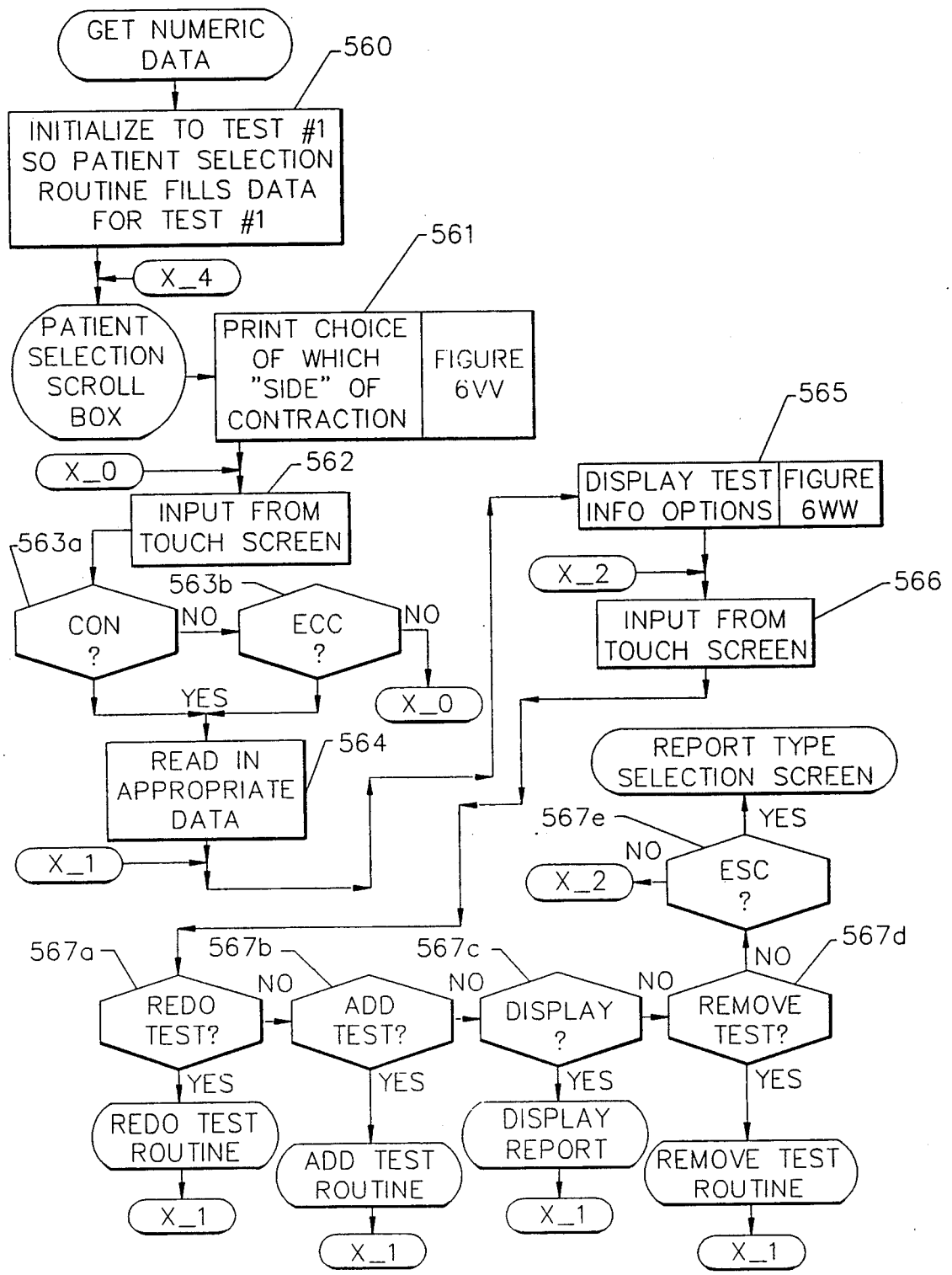
Figure 5K:
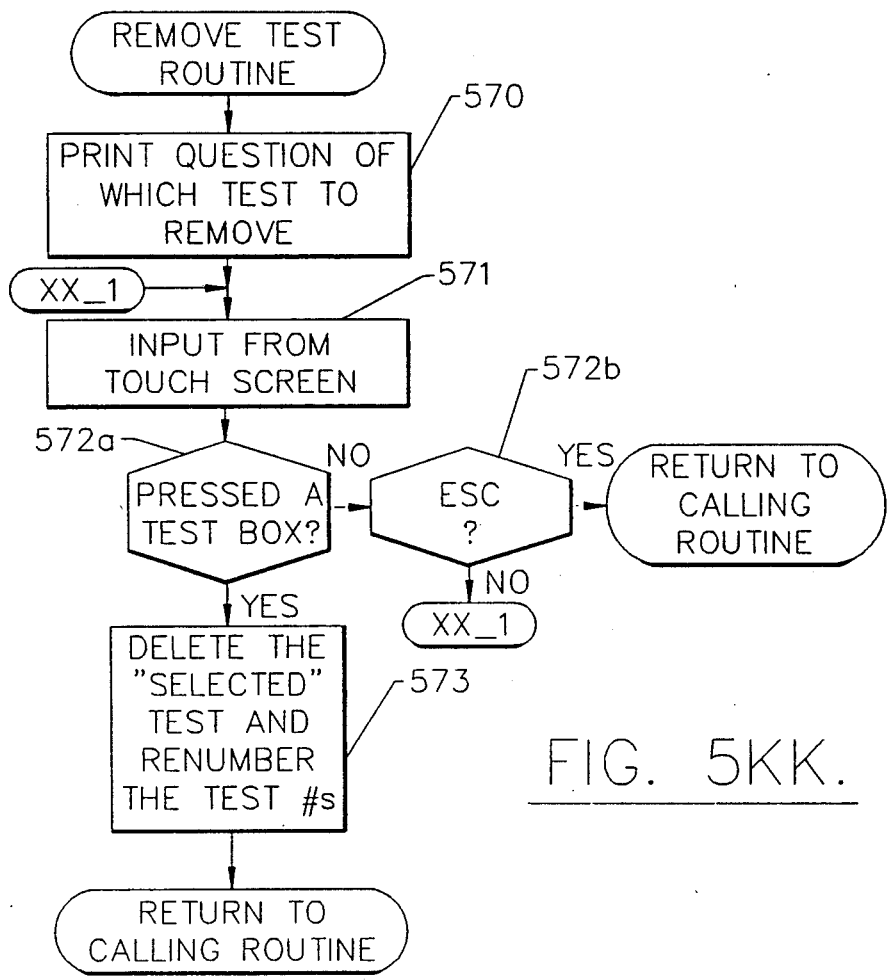
Figure 5L:
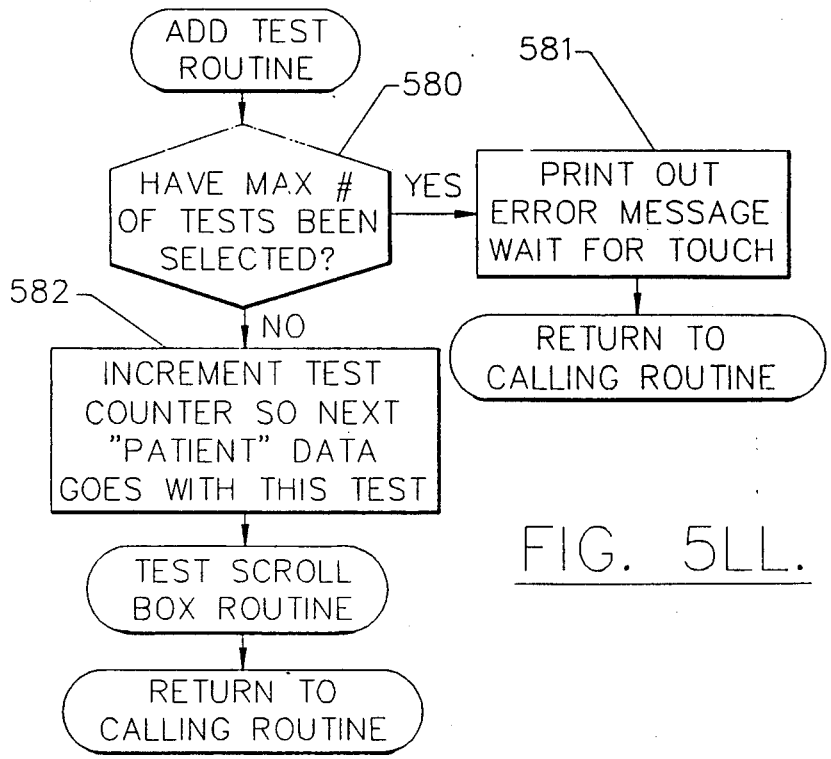
Figure 5M:
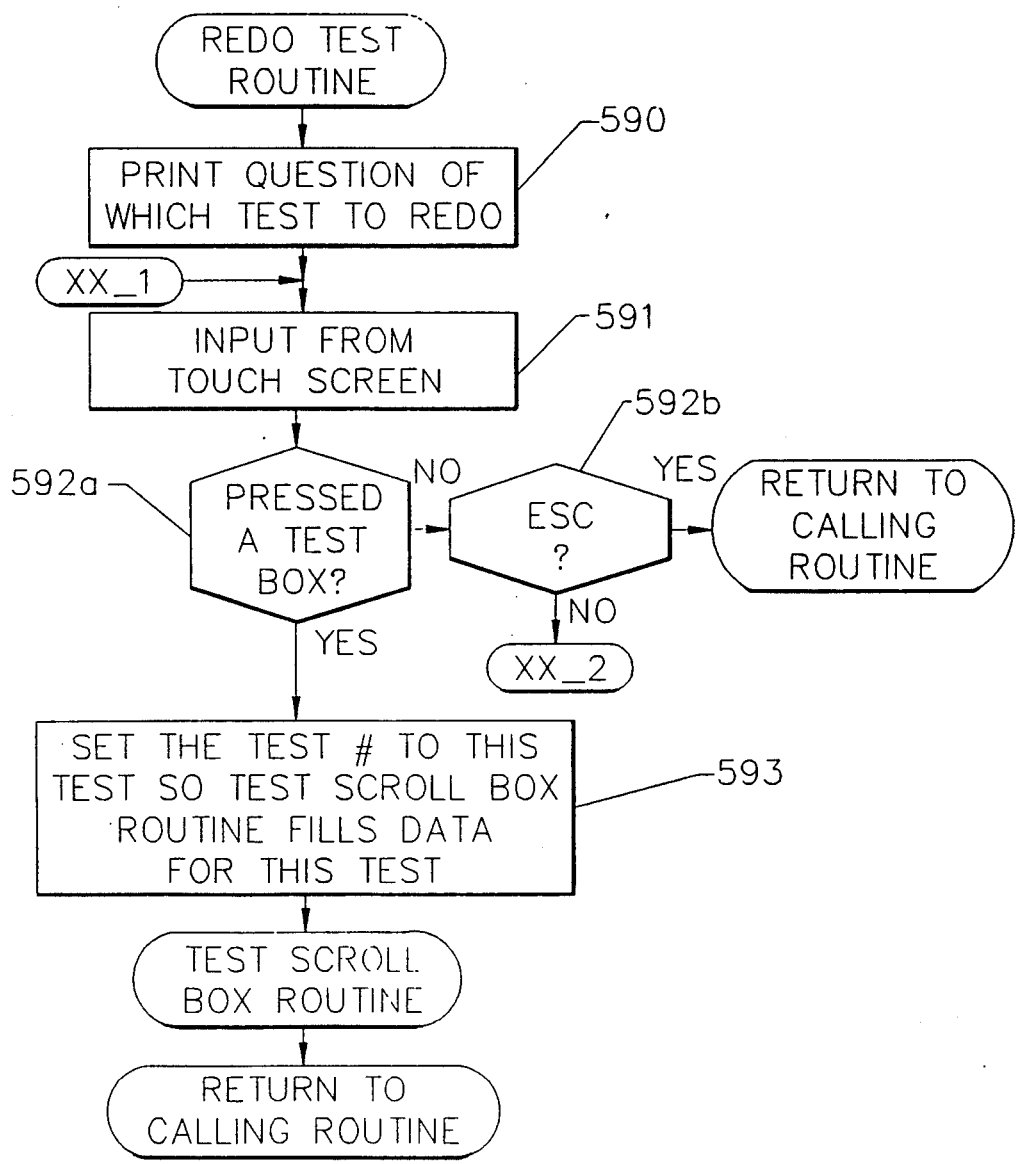

Referring to FIGS. 5X, 5Y, and 5Z, the control flow of processing of training results will now be described. The operator can select the type of display for displaying the results of an exercise. Additionally, the scroll box listing patients is used in selecting the patient, the test date, as well as the particular test results to be displayed. Consistent with the use of the scroll box or window in regards to selection of protocols, the names of the patients or users are displayed on display 30a from within the window or scroll box. The operator selects a patient name from the window by scrolling up or down the list of names, a portion of which is contained within the window. Scrolling the list is accomplished by indicating the direction to be scrolled by pressing the appropriate UP or DOWN box option on the scroll box. When the desired patient name appears within the highlighted or horizontal selection area of the window, the operator can ACCEPT that name via the touch screen or the keyboard.

Another scroll box containing a partial list of test dates associated with the selected patient or user name will then appear on the screen. As was the case with the list of patient names, the operator can select a particular date by scrolling up or down the total list of dates by making the appropriate indication in the UP or DOWN portions of the scroll box resulting in the desired test date being located in the horizontal selection area of the scroll box. The operator can ACCEPT the date located within the horizontal selection area of the scroll box by making an indication on the touch screen or the keyboard.

It is also possible to then select a particular test or evaluation performed on the selected data. This is also accomplished via a scroll box having a partial list of the tests or evaluations appearing in the window. The operator can make a selection by scrolling UP or DOWN the list of tests by indicating the direction to scroll on the touch screen. Once the desired test is located in the horizontal selection area, the operator can ACCEPT or select this test by making the appropriate indication on the touch screen or on the keyboard.

More particularly, in referring to FIG. 5X, control is transferred to transition Block RESULTS as a result of the operator selection of a desire to produce results from an evaluation session. As previously mentioned, the operator has the option of selecting TRAINING, EVALUATION, RESULTS or UTILITIES and SETUP. A display is made at 400 of the type of results, including OVERLAY which refers to interrupted stroke and CONTINUOUS, which the operator can select. An example of the display which will appear on display screen 30a is illustrated in FIG. 6EE. Consistent with the touch screen interface, the operator makes a selection of the type of results at 401 by making the appropriate indication on the touch screen or entering the digit to the left of the type of results on a keyboard. Based upon a determination at 402a that the OVERLAY type of result was not selected, a determination is made at 402b whether the CONTINUOUS type of result was selected. Based upon a determination at 402b that CONTINUOUS was not selected, the types of results continue to be displayed at 400 as indicated by the transfer of control to transition Block R__O until the operator makes a selection. If CONTINUOUS was selected, control is transferred to transition Block CONTINUOUS RESULTS which will be described following the description of OVERLAY results.

Based upon a determination at 402a that OVERLAY results were selected, the types of overlay results including STANDARD, COMPARE, NUMERIC and CHANGE FORCE TO TORQUE types of overlay reports are displayed at 403 as illustrated in FIG. 6FF. Consistent with the touch screen interface, the operator selects the desired type of overlay report at 404 by making the appropriate indication on the touch screen or entering the digit to the left of the type on the keyboard.

Consistent with the processing of previous situations where the operator can select from a number of options, a sequential multi-block decision flow is illustrated generally at 405. Based upon a conclusion at either 405a that a STANDARD RESULT was selected or at 405b that COMPARE RESULT type of overlay report was selected, the data for test number 1 is obtained at 406 using the patient scroll box processing. Control is transferred to transition Block PATIENT SELECTION SCROLL BOX which results in selection of the desired patient name from the data files. As previously described, the access logic provided by the database architecture utilizes ISAM (Indexed Sequential Access Method). The particular test date and test for the selected patient will also be obtained during the patient selection scroll box process. Upon return of control from the PATIENT SELECTION SCROLL BOX processing, the patient, test date and test for the second test to appear in the results will be defaulted to the patient and date for the first test (Block 407).

The second test is then processed in order to permit modification of the default for the second test. A scroll box containing the tests for the "current" patient and date are displayed at 408. An example of the display is illustrated in FIG. 6GG. The display contains the test number in terms of the number of the test and the results, the patient name and the date of the evaluation or test. The window contains a partial list of the actual tests conducted on the particular date. Consistent with the touch screen interface, the operator selects at 409 the desired test for the specified date using the scroll box or entering the test name via the keyboard.

A determination is made generally at 410 as to which of the options appearing in FIG. 6GG was selected by the operator. This determination process is illustrated using sequential multiple decision blocks. Based upon a determination at 410a that the operator made an indication to scroll UP the list of test names located in the window, the partial list within the window will move downward in a vertical direction resulting in the previous test in alphabetical order being located in the horizontal selection area or highlighted area (Block 411). If it is concluded at 410b that the operator indicated on the touch screen a desire to scroll DOWN the list of test names appearing in the window, the list within the window will move upward in a vertical direction at 411b resulting in the next test in alphabetical order appearing in the highlighted or horizontal selection area. Whether the UP zone, i.e. the UP box portion of the scroll box, or the DOWN zone, i.e. the DOWN portion of the scroll box, was touched by the operator, once the scrolling procedure is complete at 411a or 411b, control is transferred to transition Block R__2 resulting in the display remaining unchanged until the operator makes another test name selection or option selection.

Based upon a conclusion at 410c that the operator entered a test name via the keyboard, the scroll box automatically scrolls the list of test names appearing in the window portion until the test name closest to that entered by the operator appears in the highlighted or horizontal selection area (Block 411c). Once the test name closest to that keyed in by the operator appears in the horizontal or highlighted selection area, control is transferred to transition Block R__2, resulting in the continued display as illustrated in FIG. 6GG with the closest match appearing in the horizontal selection area. This permits the operator to then either scroll the test names, key in another test name, or select one of the options on the touch screen.

If neither the UP or DOWN zone were selected and the keyboard was not touched by the operator, a determination is made at 410d whether the operator indicated a desire to select a patient. This permits the operator to change the patient for the second test whose results are to be displayed. If the SELECT PATIENT option was chosen by the operator, control is transferred to transition Block PATIENT SELECTION SCROLL BOX. This results in selection of a patient name, test date and test. Based upon a determination at 410e that the operator indicated a desire to choose the SELECT DATE option, control is transferred to transition Block DATE SELECTION SCROLL BOX. This transfer of control permits the operator to select a different test date where evaluations were performed by a particular patient.

A determination is made at 410f whether the operator selected the ESCape option. Based upon a determination that the ESCape option was selected, control is transferred back to the report type selection display resulting in display of the type of results at 400 as illustrated in FIG. 6EE. Finally, a determination is made at 410g whether the operator selected the ACCEPT option. If the ACCEPT option was selected, processing continues with the display of the information for test 1 and test 2. However, if the ACCEPT option was not selected, control is transferred to transition Block R—2 provided for purposes of illustration to indicate that the display remains unchanged until the operator either selects a test name, enters a test name via the keyboard, selects a patient or a data, accepts the selections or selects the escape option.

In the event the patient or date was selected to obtain a different Test 2 or the tests were accepted, the computer controller locates the data in the data files associated with the patient name, date, and tests selected. This data access occurs as previously described in conjunction with the data base architecture using the indexed sequential access method. The information for the first and second tests obtained from the data files is displayed at 412. An example of the display is illustrated in FIG. 6HH. Consistent with the touch screen interface, the user can select one of the options appearing on the display including the ESCape option, the REDO TEST option, or the DISPLAY option at 413. A determination is made at 414 generally as to which of the options was selected by the operator. This determination is illustrated using multiple sequential decision blocks.

Based upon a conclusion at 414a that the REDO TEST option was selected, the test to be redone will be displayed at 415 in red. Consistent with the touch screen environment, the operator selects at 416 which test is to be redone by making an indication on the touch screen. Whether the operator selects test number 1 on the touch screen or test number 2 on the touch screen at 417a or 417b to be redone, control is transferred to transition Block R—2 resulting in display of the current patient name and date as appears in the example in FIG. 6GG selected from one of the test summaries located in FIG. 6HH. This permits the operator to select a different test whether it be for a different patient or different date or simply a different test to replace the test previously selected to be displayed in the results.

The operator also can select the ESCape option to exit the REDO processing. Based upon a determination at 417c that the ESCape option was selected, control is transferred to transition Block R—3 resulting in display of the summary for the two tests selected, an example which is illustrated in FIG. 6HH. In other words, this permits the operator to escape the REDO processing to permit the selection of a different option such as ESCape from the report type selection or to DISPLAY the reports. If the ESCape option also is not selected while in the REDO processing, control is transferred to transition Block R—5 provided for illustration to indicate that the system waits until the operator selects one of the options by making an indication on the touch screen.

Based upon a determination at 414b, that the operator selected the ESCape option among the choices displayed on the summary of the selected tests, an example of which is illustrated in FIG. 6HH, control is transferred back to the report type selection screen resulting in display of the types of overlay reports at 404, as illustrated in FIG. 6FF. Finally, a determination is made at 414c as to whether the operator has selected the DISPLAY option. Based upon a conclusion at 414c that the operator did not select the DISPLAY option, the computer controller waits until the operator selects an option on the touch screen or the keyboard. However, if the DISPLAY option is selected, control is transferred to transition Block DISPLAY REPORT resulting in processing of various parameters to enable the computer controller to display the reports in a desired format.

Returning generally to 405, i.e. the sequential decision block, based upon a determination at 405c that the numeric result option was selected at 404 from the types of overall reports displayed at 403 as illustrated in FIG. 6FF, control is transferred to transition Block GET NUMERIC DATA. GET NUMERIC DATA will be described following the description of CONTINUOUS RESULTS.

Based upon a determination at 405d that the option to CHANGE FORCE TO TORQUE for the overlay results was selected, an internal toggle is switched so the display at 418 is switched from torque to force or from force to torque depending on its current setting. This display parameter is simply a flip-flop or toggle switch as used for other parameters within the present invention and is known to those skilled in the art. Control is then transferred to transition Block R—1 resulting in the continued display of the types of overlay reports at 404 as illustrated in FIG. 6FF. This permits the operator to make another selection of type of overlay report.

Finally, a determination is made at 405e whether the ESCape option was selected by the operator. If the ESCape option was selected, control is transferred to R—0 resulting in display of the type of results at 400 including overlay or continuous results. These types of results appear on the display screen 30a as illustrated in FIG. 6EE. However, if none of the options of type of overlay reports were selected, control is transferred to transition Block R—1 provided for illustration to indicate that the computer controller providing result processing waits until the operator selects an option by making an indication upon the touch screen or the keyboard.

Referring to FIGS. 5AA and 5BB, the control flow of display report processing will now be described. As a result of a determination at 414c that the operator selected the DISPLAY option from those illustrated in FIG. 6HH during the results processing, control was transferred to transition Block DISPLAY REPORT.

This trasfer of control results in generation of the reports based upon the data contained in the data records accessed from the data files pursuant to the particular patient names, dates and tests selected by the operator. The operator has the option of controlling the generation of reports in terms of various factors including markers, the scale, and the medium upon which the report is printed.

The data for each of the two tests selected is plotted at 430 on display 30, an example of which is illustrated in FIG. 6II. Consistent with the touch screen interface, the operator selects at 431 one of the report display options including MARKERS, SCALE and PRINT to adjust the display. A multiple sequential decision block, generally at 432, determines which of the options was selected by the operator. Based upon a determination at 432a that the MARKERS option was selected, the markers are defaulted to "average" markers. Average markers means there are two markers present and the numeric data on the display refers to the average of the data between the two markers. Additionally, the "current" marker, i.e. the one currently being adjusted, is set to left (Block 433). The adjustment options are then displayed at 434 on the result display, an example which is illustrated in FIG. 6JJ.

The operator has the option of setting the left marker and then the right marker. Consistent with the touch screen interface, the operator selects one of the marker options at 435 by indicating the selection at the appropriate location on the touch screen. A determination is made at 436 whether the average markers are set. If the average markers are not set, control is transferred to transition Block Mark_V. This permits the operator to then set the average values.

Based upon a conclusion at 436 that the average markers are set, a determination is then made as generally indicated at 437 as to which marker option the operator selected via touch screen. This determination is illustrated as a sequential multiple decision block. Based upon a conclusion at 437a that the operator selected the ESCape option, control is transferred to transition Block D_1 resulting in display of the result plot and markers permitting the operator to further modify the plot by selecting a plot parameter option at 431.

The operator can move the "current" marker to the left or to the right resulting in adjustment of the values on the screen. Based upon a determination at 437b that the operator selected the LEFT ARROW (←) as illustrated in FIG. 6JJ indicating a desire to move the "current" marker to the left, the computer controller shifts the "current" marker to the left at 438 and then adjusts the values on the screen accordingly. Control is then transferred to transition Block D_2 permitting the operator then to make another selection at 435 to further adjust any of the marker options. If it is determined at 437c that the operator selected the RIGHT ARROW (→) touch key as illustrated in FIG. 6JJ indicating a desire to move the "current" marker to the right, the computer controller shifts the "current" marker to the right and adjusts the data displayed on display 30a in accordance with the new location of the "current" marker (Block 439). As an example of a left shift, referring to FIGS. 6II and 6JJ, the marker has been moved to the left resulting in change of the range of motion from 10 to 80 degrees in FIG. 6II to 10 to 50 degrees in FIG. 6JJ. The computer controller then recomputes the averages for the tests based upon this newly defined range of motion.

The operator can also switch from average markers to value marker by selecting the SET VALUE touch key. Based upon a determination at 437d that the SET VALUE option was selected, the marker is changed to one value marker and the computer controller will adjust the display to indicate this change (Block 440). Value marker means that just one marker is present and the numeric data on the display refers to the data values under the marker. The value marker can be moved to the right or left, thus moving the display of the data as it is under the marker.

Finally, the operator can select which marker is defined as the "current" marker to permit movement of both the right and the left markers. This permits the operator to shift the right marker if desired once the left marker has been shifted and vice versa. Based upon a conclusion at 437e that the SET LEFT/SET RIGHT option was selected, the "current" marker will be toggled to equal the right marker at 441. The "current" marker flag is a toggle or flip-flop and merely has one of two values. If the value of the "current" marker is set to left and the SET LEFT/SET RIGHT option is selected, the "current" marker will be set to right. Similarly, if "current" marker is presently set to right, selection of the SET LEFT/SET RIGHT option will result in the "current" marker being set to left. Control is then transferred to transition Block D_0 provided for purposes of illustration to indicate that the operator can select another option in order to further adjust the format of the markers in the display of the test results. Similarly, if none of the options were selected by the operator, control is transferred to D_2 provided for purpose of illustration to indicate that the system waits, i.e. the report will remain unadjusted, until the operator either selects the ESCape option or one of the marker adjustment options.

Returning to the multiple decision block generally at 432, based upon a determination at 432b that the ESCape option as illustrated in FIG. 6II was selected, control is transferred to transition Block R_3. This results in display of the summary information at 412 for the two tests selected by the operator, the example of which is illustrated in FIG. 6HH. This permits the operator then to either select a different test or display the test again or change the report type. Based upon a determination at 432c that the operator selected the SCALE option as illustrated in FIG. 6II, the computer controller will prompt the operator at 442 to enter a new scale value from the keyboard. Key entry via the keyboard at 443 of the new scale value causes the computer controller to adjust the Y axis as well as the values located along the Y axis of the tests presently being displayed according to the new scale. Control is then trasferred to transition Block D_10 which results in adjustment of the test results on the display causing a new plot of the test data on the display for all test results being displayed at 430.

Finally, a determination is made at 432d whether the PRINT option was selected by the operator via the touch screen or the keyboard. Based upon a determination at 432d that the PRINT option was selected, the test result report presently displayed on display 30a is printed on the line printer (Block 444). This permits the operator to maintain a "hard copy" of the test result whether it be in standard, comparison, or any other type of report as selected by the operator at 405 of FIG. 5X. Control is then transferred to transition Block D_1 provided for purposes of illustration indicating that the operator can make another selection of the report format options including MARKERS, SCALE and PRINT. Control is also transferred to transition Block D—1 based upon a determination at 432d that the PRINT option was not selected. This transfer of control to transition Block D—1 is a result of a determination that generally at 432 that none of the options were selected, and is provided for purposes of illustration indicating that the system remains in a wait state until the operator makes a selection of one of the options.

Referring to FIG. 5CC, control of the processing following a determination at 436 of FIG. 5BB that the average markers were not set will now be described. A sequential multiple decision block is provided generally at 450 to determine which of the options is selected by the operator when the average markers are not set. Based upon a determination at 450a that the ESCape option was selected, control is transferred to transition Block D—1 permitting the operator to make a selection of one of the display parameters at 431, an example of which is illustrated in FIG. 6II, including MARKERS, SCALE and PRINT.

The operator may also shift the marker to the left or the right even though the average markers are not set. Based upon a determination at 450b that the operator selected the LEFT ARROW (←) expressing a desire to move the marker to the left, the marker is moved to the left at 451 resulting in the computer controller adjusting the values according to the new marker location. Based upon a determination at 450c that the operator indicated a desire to move the marker to the right by touching the RIGHT ARROW (→) on the touch screen, the marker is shifted to the right at 452 resulting in the computer controller adjusting the values on the display in accordance with the new location of the marker. Whether the operator selected the left arrow or the right arrow to shift the marker one direction or the other, control is transferred to transition Block D—2 once the adjustment of the marker and the values has been made on the display by the computer controller. Transfer of control to transition Block D—2 permits the operator to make another selection as to marker format at 435 of FIG. 5AA.

Finally, a determination is made at 450d whether the operator selected the SET AVERAGE option. Based upon a conclusion that the operator selected the SET AVERAGE option, the marker is changed to two average markers at 453. As previously described, this means that two markers appear on the display with the numeric data referring to the average of the data between the two markers. Additionally, the "current" marker is set to the left marker at 453. Finally, the computer controller adjusts the values on the display in accordance with the new locations of the markers and the new "average" markers (Block 453). Control is then transferred to transition Block D—0 resulting in a new plotting of the test results based upon any adjustments to the markers and values made by the operator. This permits the operator to make further adjustments to the test result display format parameters.

If none of the options including ESCape, SHIFT LEFT, SHIFT RIGHT, or SET AVERAGE were selected by the operator, control is transferred to transition Block D—2 indicating that the system waits until the operator selects one of the options.

Referring to FIG. 5DD, the control flow of the PATIENT SELECTION SCROLL BOX processing will now be described. Generally, this processing permits operator selection of patient names and ultimately test dates and individual tests using the scroll box containing a window portion and UP/DOWN selection options. This scroll box permits data retrieval using the window and UP/DOWN options without requiring the operator to know how the data is organized and without requiring the operator to assign or remember a particular file name for the data. The data is stored as previously described in reference to the database architecture utilizing ISAM (Indexed Sequential Access Method).

More specifically, as a result of operator selection of the STANDARD RESULT, COMPARISON RESULT, or NUMERIC RESULT type of overlay report formats at 404 of FIG. 5X and based upon a determination that one of these formats was selected, the scroll box is displayed at 460 of FIG. 5DD on display 30a containing a partial list of the patient names. An example of the display appearing on display 30a containing the scroll box with a partial list of patient names appearing in the scroll box is illustrated in FIG. 6KK. The patient names will appear in either upper or lower case or both upper and lower case depending upon the key entry of the patient name by the operator. Consistent with the touch screen interface, the operator selects one of the options at 461 including scrolling UP or DOWN the list of patient names, entering a patient name via the keyboard, or selecting either the ESCape or ACCEPT option. A determination is made generally at 462 as to which option was selected by the operator as indicated by the sequential multiple decision block.

Based upon a conclusion at 462a that the operator touched the UP zone of the window or scroll box on the touch screen, the list of names located in the window will be moved downward in a vertical direction resulting in the previous name being located in the highlighted or horizontal selection area within the window (Block 463). Similarly, based upon a determination at 462b that the operator indicated a desire to scroll down the list of patient names by touching the DOWN zone of the scroll box, the list of names appearing in the scroll box is moved upward in a vertical direction resulting in the next name in alphabetic order being located in the highlighted or horizontal selection area within the scroll box (Block 464). Once the scrolling is completed by the computer controller, regardless of the direction of scrolling, control is transferred to transition Block R—S1 provided for illustration purposes to indicate that the system waits, continuing to display the adjusted partial list within the window, i.e. either the next or previous name located in the highlighted or horizontal selection area, until the operator selects another option.

A determination is made at 462c whether the operator selected the ESCape option. Based upon a determination at 462c that the ESCape option was selected, control is transferred to the processing whereby the types of overlay reports are displayed on display 30a, an example of which is illustrated in FIG. 6FF. This permits the operator to select a different overlay type format for the test report results. The types of overlay reports are then displayed at 403 of FIG. 5X.

Based upon a determination at 462d that the operator selected the ACCEPT option, the list of dates or tests associated with the patient name located within the highlighted or horizontal selection area of the window or scroll box are retrieved at 465. Thus, selection of the ACCEPT option results in the operator's accepting the patient name appearing in the selection area. The list of dates for the selected patient are retrieved at 465 in accordance with the process described by the database architecture. Control is then transferred to transition Block DATE SCROLL BOX ROUTINE. This permits the operator to select the desired test date using the scroll box similar to the selection of the patient name.

Finally, a determination is made at 462e whether the operator touched the keyboard rather than indicated a selection of one of the options on the touch screen. Based upon a conclusion at 462e that the operator did touch the keyboard, the partial list of patient names appearing in the window are scrolled to locate the name closest to the name entered by the operator on the keyboard (Block 466). Thus, the closest matching name to that keyed in by the operator is located in the highlighted or horizontal selection area of the window. Control is then transferred to transition Block R_S1 permitting the operator to make another selection of one of the options including scrolling UP or DOWN of the list of names, entering a name via the keyboard, or selecting either the ACCEPT or ESCape option.

If none of the options were selected by the operator, control is transferred to transition Block R_S1 provided for illustration purposes to indicate that the system remains unchanged until the operator indicates his or her selection of scrolling the list of patient names, entering a patient name via the keyboard, or selection of the ESCape or ACCEPT options at 461.

Referring to FIG. 5EE, the control flow of processing for selecting the test date for a particular patient will now be described. Based upon an operator's acceptance at 461 as determined at 462d of a particular patient name, the list of test dates for the particular patient was retrieved at 465. This transferred control to transition Block DATE SCROLL BOX ROUTINE. This transfer of control results in display of the test dates associated with the "current" patient name, i.e. the patient selected by the operator (Block 470). The list of test dates is displayed in the scroll box whereby a partial list of test dates appears in the scroll box, an example which is illustrated in FIG. 6LL. The test dates can be stored in a number of different orders. This particular embodiment stores the test dates in numeric order based on ASCII representation. Consistent with the touch screen interface, the operator can either scroll the list of test dates UP or DOWN, enter a test date via the keyboard, or select either the ESCape or ACCEPT option by making an indication at the appropriate location on the touch screen at 471.

A determination is made generally at 472 as to which option the operator selected. The decision is illustrated generally at 472 by a sequential multiple decision block. Based upon a determination at 472a that the operator indicated a desire to scroll up the list of test dates by touching the UP zone of the scroll box, the list of test dates in the window is moved downward in a vertical direction at 473 resulting in the previous date in reverse chronological order being located in the highlighted or horizontal selection area within the window. Similarly, based upon a decision at 472b that the operator indicated a desire to scroll down the list of test dates by touching the DOWN zone of the scroll box, the list of test dates appearing in the window is moved upward in a vertical direction at 474 resulting in the next date in chronological order being located in the highlighted or horizontal selection area of the window. Whether the operator scrolled UP or DOWN the list of test dates, control is transferred to transition Block R_S2 permitting the operator to select another option including further scrolling of the test dates, key entry of a test date, or selection of either the ESCape or ACCEPT option.

If it is determined at 472c that the operator selected the ESCape option, control is transferred back to the report type selection screen, i.e. FIG. 6FF. This results in display of the types of overlay reports at 403 of FIG. 5X, including STANDARD RESULT, COMPARISON RESULT, NUMERIC RESULT, or CHANGE FORCE TO TORQUE, which the operator may select to display the test results.

Based upon a determination at 472d that the ACCEPT option was selected, the list of tests conducted on the particular selected date are retrieved. In other words, once the operator has determined the particular test date for which he or she wants to review the results, all the tests conducted on that date will be retrieved. The acceptance causes retrieval for all tests conducted on the particular date located in the highlighted or horizontal selection area of the window or scroll box. Retrieval of the tests is consistent with the database architecture previously described using ISAM (Indexed Sequential Access Method). This retrieval occurs at Block 475. Control is then transferred to transition Block TEST SCROLL BOX ROUTINE.

Finally, a determination is made at 472e whether the operator touched the keyboard. Based upon a determination at 472e that the operator did touch the keyboard, the computer controller scrolls the list of dates appearing in the window in the appropriate direction to locate the closest matching date in the highlighted or horizontal selection area to the date keyed in by the operator via the keyboard (Block 476). Once the closest chronological date to that entered by the operator is located in the highlighted or horizontal selection area, control is transferred to transition Block R_S2. This results in the system waiting until the operator scrolls the scroll box in the UP or DOWN direction, enters another date via the keyboard, or selects either the ESCape or ACCEPT option.

If it is determined at 472e that the operator did not touch the keyboard, and consequently, selected none of the options, control is transferred to transition Block R_S2. This transfer of control is provided for illustration purposes to indicate that the system will wait until the operator selects one of the options available as illustrated in FIG. 5LL including scrolling UP or DOWN the list of test dates, entering a test date via the keyboard, or selecting the ACCEPT or ESCape option.

Referring to FIG. 5FF, the control flow of the TEST SCROLL BOX ROUTINE will now be described. Generally, based upon an acceptance by the operator of a particular test date (see FIG. 5EE), the operator can then select particular test results for tests conducted on the selected test date. The selection of the particular test is made using the scroll box of the present invention including the UP and DOWN zones, and the highlighted or horizontal selection area.

More particularly, the list of tests conducted on the selected date for the selected patient is displayed at 480 in the window or scroll box on display 30a, an example of which is illustrated in FIG. 6GG. Consistent with the touch screen interface, the operator can then either scroll UP or DOWN the list of tests appearing in the window portion or select one of the ESCape or ACCEPT options by making an indication at the appropriate location on the touch screen at 481. The operator may also enter a particular test name at the keyboard.

A determination is made generally at 482 as to which option the operator selected. The decision is illustrated generally at 482 as indicated by the sequential multiple decision block. Based upon a determination at 482a that the operator indicated a desire to scroll up the list of tests by pressing the UP zone on the scroll box, the list of tests in the scroll box or window are moved downward in a vertical direction resulting in the previous test in the list being located in the highlighted or horizontal selection area. Similarly, based upon a determination at 482b that the operator indicated a desire to scroll down the list of test names in the window portion by touching the DOWN zone of the scroll box on the touch screen, the list of tests located in the scroll box are moved upward in a vertical direction at 484 resulting in the next test being located in the highlighted or horizontal selection area. Whether the operator scrolled UP or DOWN the list of tests in the window, control is transferred to transition Block R—S3 permitting the operator to make another selection at 481 of scrolling the list of tests, entering a test at the keyboard, or selecting either the ESCape or ACCEPT option.

A determination is made at 482c whether the operator selected the ESCape option. Based upon a determination at 482c that the ESCape option was selected, control is transferred back to the report type selection screen at 403 of FIG. 5X resulting in the display of FIG. 6EE. This permits the operator to escape the test selection process and select another type of overlay format for displaying the test results.

A determination is made at 482d whether the operator selected the ACCEPT option. Based upon a determination at 482d that the operator selected the ACCEPT option indicating a desire to display the results of the test located in the horizontal or highlighted selection area of the window, the "current" test, i.e. the highlighted test, for the "current" or selected date and the "current" or selected patient is retrieved at 485 from the data files. The retrieval of the test from the data files is accomplished based upon the database architecture as previously described using ISAM (Indexed Sequential Access Method). Control is then returned to the processing from which the TEST SCROLL BOX ROUTINE received control. This permits the computer controller to continue to control the processing in light of any new selections made by the operator.

Finally, a determination is made at 482e whether the operator touched the keyboard. Based upon a determination at 482e that the operator touched the keyboard in making an indication of a desire to key enter a test name, the computer controller at 486 scrolls the list of tests appearing in the window to locate the test closest matching the test which was key entered by the operator. The test which closest matches that keyed in by the operator will be located in the highlighted or horizontal selection area of the window or scroll box. Control is then transferred to transition Block R—S3 to permit the operator to make another selection of an option at 481 including scrolling of the list of tests in the window, keying in a test at the keyboard, or selecting either the ESCape or ACCEPT option.

Based upon a determination generally at 482 that none of the options were selected by the operator, control is transferred to transition Block R—S3. Transition Block R—S3 is provided for purposes of illustration to indicate that the system waits until the operator selects an option such as scrolling the list of tests in the window in the UP or DOWN direction, entering a test via the keyboard, or selecting either the ESCape or ACCEPT option.

Referring to FIG. 5GG, the process of CONTINUOUS RESULTS will now be described. Based upon a determination at 402b (see FIG. 5X) that the operator selected CONTINUOUS type results, control is transferred to transition Block CONTINUOUS RESULTS. Referring again to FIG. 5GG, this transfer results in the display of the continuous result options at 500, an example which is illustrated in FIG. 6MM. The operator then selects the desired option by making an indication at the appropriate location on the touch screen interface or by entering the digit to the left of the desired option via the keyboard (Block 501). The options from which the operator may choose include displaying the test, varying the time scale for viewing evaluation files, changing force to torque, or escaping to return to the results selection screen at 400.

A determination is made generally at 502 to determine which option was selected by the operator. Based upon a determination at 502a that the operator selected the DISPLAY TEST option, the test data is obtained through the patient scroll box routines as indicated at 503 as illustrated by inclusion of transition Block PATIENT SELECTION SCROLL BOX in the flow of FIG. 5GG. The selection of the patient name, test date, and test is identical to that described for overlay results in reference to FIGS. 5DD, 5EE and 5FF. Examples of the displays which appear on monitor 30 during the patient, test date and test selection process for continuous results are illustrated in FIGS. 6NN, 600 and 6PP. The summary of the selected tests including patient name, test date and test results are displayed at 504. An example of the test information summary which is displayed on monitor 30 is illustrated in FIG. 6QQ. The operator then can make a selection to redo the test if the selected test was incorrect, display the continuous results of the selected test, or escape by making the appropriate indication on the touch screen at 505.

A determination is made generally at 506 as to which option was selected by the operator. Based upon a determination at 506a that REDO TEST was selected, the test to be redone is displayed in red (Block 507). The operator can then either select the test to be redone or select the ESCape option at 508. Based upon a determination 509a that the ESCape option was selected, control is transferred to transition Block C—3 resulting in display of the test information summary at 504, permitting the operator to redo the test, display the test in continuous results, or escape the display test processing. Based upon a determination of 509b that an indication was made to redo test number 1 by touching the appropriate location on the touch screen, control is transferred to transition Block C—2 permitting the operator to select a different patient, test date, or test.

Based upon a determination of 506b that the operator selected the ESCape option from the test information summary display, control is transferred to transition Block C—1 resulting in display of the continuous options at 500, an example of which is illustrated in FIG. 6MM. Finally, a determination is made at 506c whether the operator selected the DISPLAY option from the test information summary screen display. Based upon a determination at 506c that the DISPLAY option was selected, control is transferred to transition Block DISPLAY CONTINUOUS REPORT. This permits the operator to then alter the DISPLAY formats for displaying the continuous report on monitor 30. If it is determined at 506c that the DISPLAY option was not selected, meaning that the operator has not selected any of the options from the test information summary display, control is transferred to transition Block C_4, provided for illustration purposes to indicate that the test information summary continues to be displayed on monitor 30 unti the operator makes a selection of one of the options including redoing the test, escaping the display test processing, or displaying the test.

Based upon a determination at 502b that the operator selected the TIME SCALE option from the continuous display options illustrated at 500, the touch key calculator will appear on monitor 30 at the right side of the display to permit the operator to vary the time scale for viewing the evaluation files (Block 510). The new time scale value is entered at 511 via the touch calculator. The computer controller then sets the time scale value to a multiple of 5 at 512. The time scale appears on monitor 30 in 5 second increments, permitting the operator to vary the time scale based upon the 5 second increments. Referring to FIG. 6MM, the time scale is 5. Based upon the determination at 502b that the operator selected the time scale option and entered a new time scale of 60 at 511, an example of the result displayed on monitor 30 is illustrated in FIG. 6RR. Once the time scale has been set, control is transferred to transition Block C_1 resulting in display of the continuous result options at 500.

Based upon a determination at 502c that the operator selected the CHANGE FORCE TO TORQUE option, the computer controller switches the display of the units from torque to force if the units are presently in torque and from force to torque if the units are presently in force (Block 513). Control is then transferred to transition Block C_1 resulting in display of the continuous result options with the new force or torque setting at 500.

Finally, a determination is made at 502d whether the ESCape option was selected. Based upon a conclusion at 502d that the ESCape option was selected, control is transferred to transition Block R_O resulting in display of the type of results at 400 of FIG. 5X. This permits the operator to select either the overlay or continuous result option. If it is determined at 502d that the ESCape option was not selected, control is transferred to transition Block C_1 provided for illustration purposes to indicate that the computer controller waits until the operator selects one of the continuous result options including DISPLAY TEST, TIME SCALE, CHANGE FORCE TO TORQUE, or ESCape.

Referring to FIG. 5HH, control of the processing flow of displaying a continuous report will now be described. Based upon a determination at 506c of FIG. 5GG that the DISPLAY option was selected, the values for all the parameters are displayed on monitor 30 at 520. An example of the display having all parameter values is illustrated in FIG. 6SS. The display of the test results in continuous result format is continued by making an indication at any location on the touch screen (Block 521). The values for the parameters are then plotted at 522 and displayed on monitor 30, an example which is illustrated in FIG. 5TT. Similar to displaying the results in overlay format, the operator can change the display formats by making a desired selection of the options including MARKERS, SCALE, PRINT, NEXT and ESCape at 523 by making the indication at the appropriate location on the touch screen.

A determination is made generally at 524 as to which option was selected. Based upon a determination at 524a that the MARKERS option was selected, the markers are defaulted to "average" (Block 525). Average markers means that two markers are used whereby the numeric data located under the markers is the average value between the two markers. The "current" marker is set to left permitting the operator to then shift the left marker in one direction or another (Block 525). The options which the operator can select for modifying the marker are displayed at 526, an example of which is illustrated in FIG. 6UU. The operator then makes a selection of one of the options including shifting the "current" marker to the left or right, setting marker to value, setting "current" marker to right, or escaping the modification of markers processing (Block 527).

A determination is made a 528 whether the average markers are set. As previously described, average markers means that two markers are present on the display and the numeric data located under the marker is the average between the two markers. Based upon a determination at 528 that the average markers are not set, control is transferred to transition Block CMARK_V. This permits the operator to modify the single marker on the display screen. If it is determined at 528 that the average markers are set, a determination is made generally at 529 as to which of the average marker modification options was selected by the operator at 527. Based upon a determination at 529a that the ESCape option was selected, control is transferred to transition Block CD_1 permitting the operator to then select another option for modifying the continuous result format at 523.

The operator can move the "current" marker to the left or to the right resulting in adjustment of the values on the screen. Based upon a determination at 529b that the operator selected the LEFT ARROW (←) as illustrated in FIG. 6UU indicating a desire to move the "current" marker to the left, the computer controller shifts the "current" marker to the left at 530 and then adjusts the values on the screen accordingly. Control is then transferred to transition Block CD_2 permitting the operator to make another selection at 527 to further adjust any of the marker options. If it is determined at 529c that the operator selected the RIGHT ARROW (→) touch key as illustrated in FIG. 6UU indicating a desire to move the "current" marker to the right, the computer control shifts the "current" marker to the right and adjusts the data displayed on display 30a in accordance with the new location of the "current" marker (Block 531). Control is then transferred to transition Block CD_2 permitting the operator to make another selection at 527 to further adjust any of the marker options.

The operator can also switch from average markers to value markers by selecting the SET VALUE touch key. Based upon a determination at 529d that the SET VALUE option was selected, the marker is changed to one value marker and the computer controller will adjust the display to indicated this change (Block 532). As previously described, value marker means that just one marker is present and the numeric data on the display refers to the data values under the marker. The value marker can be moved to the right or left, thus modifying the data under the marker. Control is then transferred to CD_0 as illustrated, resulting in display of the options which the operator can select for modifying the value marker.

Finally, the operator can select which marker is defined as the "current" marker to permit movement of both the right and left markers. This permits the operator to shift the right marker if desired once the left marker has been shifted and vice versa. Based upon a conclusion at 529e that the SET LEFT/SET RIGHT option was selected, the "current" marker will be toggled to equal the left marker at 533. The "current" marker flag is a toggle or flip-flop and merely has one of two values. If the value of the "current" marker is set to left and the SET LEFT/SET RIGHT option is selected, the "current" marker will be toggled to right. Similarly, if "current" marker is presently set to right, selection of the SET LEFT/SET RIGHT option will result in "current" marker being toggled to left. Control is then transferred to transition Block CD_0 provided for purposes of illustration to indicate that the operator can select another option in order to further adjust the format of the markers in the display of the test results in continuous result format including the new "current" marker. If none of the options were selected by the operator, control is transferred to transition Block CD_2 provided for purposes of illustration to indicate that the system waits, i.e. the report will remain unadjusted, until the operator either selects the ESCape option or one of the marker adjustment options.

Returning to the multiple decision block generally at 524, based upon a determination at 524b that the ESCape option as illustrated in FIG. 6TT was selected, control is transferred to transition Block C_1. This results in display of the summary information at 412 for the test selected by the operator, the example which is illustrated in FIG. 6HH. This permits the operator then to either select a different test or display the test again or change the report type. Based upon a determination at 524c that the operator selected the SCALE option as illustrated in FIG. 6TT, the computer controller will prompt the operator at 534 to enter a new SCALE value from the keyboard. Key entry via the key board at 535 of the new SCALE value causes the computer controller to adjust the Y axis as well as the values located along the Y axis of the tests presently being displayed according to the new scale. Control is then transferred to transition Block CD_10 which results in adjustment of the test results in continuous format on the display causing a new plot of the test data on the display for all test results being displayed at 522.

Based upon a determination at 524d that the PRINT option was selected by the operator via the touch screen, the test result reports in continuous format presently displayed on display 30a is printed on the line printer (Block 536). This permits the operator to maintain a "hard copy" of the test selected by the operator. Control is then transferred to transition Block CD_1 provided for purposes of illustration indicating that the operator can make another selection of the continuous result format options including MARKERS, SCALE, PRINT and NEXT.

Finally, a determination is made at 524e whether the NEXT option was selected by the operator via the touch screen. Based upon a determination at 524e that the NEXT option was selected, a determination is made at 537 whether there is any data remaining in the file, i.e. whether EOF (End of File) has been reached. If it is concluded at 537 that there is more data in the file, the next "block" of data is read in at 538. This retrieval of the next "block" of data is processed by the database manager as previously described. Control is then transferred to transition Block CD_10 resulting in the plotting at 522 of the next data on monitor 30. The operator then may proceed to modify the continuous result format as previously described. If it is concluded at 537 that there is no more data in the file, i.e. EOF (End of File) has been reached, control is transferred to transition Block CD_1 causing the system to wait until another selection of the continuous result format options is made by the operator.

Referring to FIG. 5II, control of the processing following a determination at 528 that the average markers were not set will now be described. A sequential multiple decision block is provided generally at 550 to determine which of the options was selected by the operator when the average markers are not set. Based upon a determination at 550a that the ESCape option was selected, control is transferred to transition Block CD_1 permitting the operator to make a selection of one of the display parameters at 523, an example of which is illustrated in FIG. 6TT, including MARKERS, SCALE, PRINT and NEXT.

The operator may also shift the marker to the left or the right even though the average markers are not set. Based upon a determination at 550b that the operator selected the LEFT ARROW (←) option expressing a desire to move the marker to the left, the marker is moved to the left at 551 resulting in the computer controller adjusting the values according to the new marker location. Based upon a determination at 550c that the operator indicated a desire to move the marker to the right by touching the RIGHT ARROW (→) option on the touch screen, the marker is shifted to the right at 552 resulting in the computer controller adjusting the values on the display in accordance with the new location of the marker. Whether the operator selected LEFT ARROW (←) or RIGHT ARROW (→) to shift the marker one direction or the other, control is transferred to transition Block CD_2 once the adjustment of the marker and the values has been made on the display by the computer controller. The transfer of control to transition Block CD_2 permits the operator to make another selection as to marker format at 527 of FIG. 5HH.

Finally, a determination is made at 550d whether the operator selected the SET AVERAGE option. Based upon a conclusion that the operator selected the SET AVERAGE option, the marker is changed to two average markers at 553. As previously described, this means that two markers appear on the display with the numeric data referring to the average of the data between the two markers. Additionally, the "current" marker is set to the left marker at 553. Finally, the computer controller adjusts the values on the display in accordance with the new locations of the "average" markers (Block 553). Control is then transferred to transition Block CD_0 permitting the operator to adjust the average markers or return to "value" marker at 527 of FIG. 5HH. If none of the options including ESCape, LEFT ARROW (←), RIGHT ARROW (→) or SET AVERAGE were selected by the operator, control is transferred to transition Block CD_2 indicating that the system waits until the operator selects one of the options for modifying the format of the average markers.

Referring to FIG. 5JJ, the control flow of the GET NUMERIC DATA will now be described. Generally, this processing permits the operator to add and remove test routines among other operations. More specifically, as a result of a determination at 405c of FIG. 5X that the operator selected the NUMERIC RESULT option, control is transferred to processing of GET NUMERIC DATA. This results in initialization of the first test so that the patient selection routine fills the data for Test 1 (Block 560). The operator then obtains patient data including patient name, test date and test data via PATIENT SELECTION SCROLL BOX as previously defined. This results in storage of the patient data as Test 1.

The selection of the NUMERIC RESULT option for overlay reports allows display of each torque or force curve superimposed with the range of motion tested. The curves can be all concentric, eccentric or a combination thereof. Thus, NUMERIC RESULT permits overlaying of individual concentric and eccentric curves for comparison. The choices of the "side" of contraction are then displayed at 561, an example of which is illustrated in FIG. 6VV. The operator then makes a selection of CONcentric or ECCentric by making the appropriate indication on the touch screen at 562. A determination is made generally at 563 as to whether the CONcentric or ECCentric option was selected. If it is determined that neither the CONcentric or ECCentric options were selected, control is transferred to transition Block X_0 provided for purposes of illustration to indicate that the system waits until the operator selects one of the options. Whether it is determined at 563a that the CONcentric option was selected or at 563b that the ECCentric option was selected, the appropriate data is read in at 564 consistent with the option selected. In other words, the concentric data or the eccentric data of the test data for the selected patient and test is obtained. The test summary and options are then displayed on monitor 30 at 565, an example of which is illustrated in FIG. 6WW. The options include REDO TEST, ADD TEST, DISPLAY, REMOVE TEST, or ESCape. The operator makes a selection of one of the options at 566 by making the appropriate indication on the touch screen.

A determination is made generally at 567 to determine which option was selected. Based upon a determination at 567a that the REDO TEST was selected, control is transferred to transition Block REDO TEST ROUTINE permitting the operator to select another test for displaying the results thereof. Once processing of REDO TEST is completed, control is transferred to transition Block X_1 resulting in display of the test options at 565 permitting the operator to select another test option.

Based upon a determination at 567b that the ADD TEST option was selected, control is transferred to transition Block ADD TEST ROUTINE. The ADD TEST ROUTINE checks to see if the maximum number of tests have been selected before obtaining another test and ensures that the appropriate patient and test data is associated with the appropriate test number. Once processing of the ADD TEST ROUTINE is complete, control is transferred to transition Block X_1 resulting in display of the test options at 565 permitting the operator to select another of the test options. Based upon a determination at 567c that the DISPLAY option was selected, control is transferred to transition Block DISPLAY REPORT. DISPLAY REPORT was described in reference to FIGS. 5AA and 5BB whereby the operator can modify the format of the chosen overlay report and view the efforts from this test. Once DISPLAY REPORT processing is complete, control is transferred to transition Block X_1 resulting in display of the test options at 565 permitting the operator to select another test information option at 566.

Based upon a determination at 567d that the REMOVE TEST option was selected, control is transferred to transition Block REMOVE TEST ROUTINE. This permits the operator to delete the selected test and renumber the tests accordingly so as to maintain the appropriate association between test numbers and patient and test data. Once processing of the removed test routine is complete, control is transferred to transition Block X_1 resulting in display of the test information options permitting the operator to select another option.

Finally, a determination is made at 567e to determine whether the ESCape option was selected. Based upon a determination at 567e that the ESCape option was selected, control is transferred to transition Block REPORT TYPE SELECTION SCREEN resulting in display of the types of overlay reports at 403 of FIG. 5X. If it is determined at 567e that the ESCape option as well as none of the other test information options were selected, control is transferred to transition Block X_2 causing the system to wait until the operator indicates a selection on the touch screen at 566.

Referring to FIG. 5KK, processing as a result of selection of the REMOVE TEST option will now be described. As result of a determination at 567d of FIG. 5JJ that the REMOVE TEST option was selected, the operator is prompted to designate which test is to be removed (Block 570). This prompt is in the form of a question which is printed on the display screen of monitor 30 asking which test is to be removed. The operator enters the number of the test to be removed via the touch screen or the keyboard at 571. The determination is made at 572 whether a test was selected by the operator to be removed. Based upon a determination at 572a that a test box was pressed, the computer controller deletes the test selected for removal at 573. The test numbers are also renumbered at 573 by the computer controller in order to correctly associate the test number with the appropriate patient and test data. Control is then returned to the routine from which REMOVE TEST received control. This removal process is performed for removal of tests and may also be used to remove protocols and other items which the operator desires to remove from the database during other processing.

Based upon the determination at 572a that no test was selected for removal, a determination is made at 572b as to whether the ESCape option was selected. If it is determined at 572b that the ESCape option was selected, control is returned to the calling routine to permit the operator to make further selections of options for producing test results and reports. If the ESCape option was not selected, control is transferred to transition Block XX_1 causing the system to wait until the operator either selects a test to be removed or the ESCape option.

Referring to FIG. 5LL, processing of the ADD TEST ROUTINE will now be described. Based upon a determination at 567b of FIG. 5JJ that the ADD TEST option was selected, a determination is made at 580 as to whether the maximum number of tests has been selected. If the maximum number of tests were selected, an error message is printed out indicating that the maximum number has been selected and the computer controller waits for a touch to return to the routine from which the add test routine received control (Block 581).

Based upon a determination at 580 that the maximum number of tests has not been selected, the computer controller increments the test counter so the next patient data becomes associated with this test number (Block 582). Control is then transferred to transition Block TEST SCROLL BOX ROUTINE to obtain another test. Once another test has been selected, control is transferred back to the routine from which ADD TEST ROUTINE received control. An example of a display once a test has been added is illustrated in FIG. 6XX.

Referring to FIG. 5MM, processing of the REDO TEST ROUTINE will now be described. As a result of a determination at 567a that the REDO TEST option was selected, the operator is prompted at 590 to make an indication as to which test is to be redone. This prompting is in the form of a question which appears on the display of monitor 30. The operator selects the test to be redone at 591 by making an indication at the appropriate location on the touch screen. A determination is made at 592a as to whether one of the tests was selected to be redone. Based upon a determination at 592a that an indication was made on the touch screen at one of the test boxes, the computer controller sets the test number to this test at 593. This permits the test scroll box routine to fill data for this test. Control is transferred to transition Block TEST SCROLL BOX ROUTINE. Processing of the TEST SCROLL BOX ROUTINE was described in reference to FIG. 5FF. This permits the operator to select a different test for either the same patient or a different patient and for either the same date or a different date. Once a new test has been selected, i.e. redone, control is transferred back to the routine from which REDO TEST ROUTINE received control.

A determination is made at 592b as to whether the ESCape option was selected. Based upon a determination at 592b that the ESCape option was selected, control is returned to the routine from which REDO TEST ROUTINE received control. If it is determined at 592b that neither the ESCape option nor one of the test boxes was selected, control is transferred to transition Block XX_2 causing the system to wait until the operator selects one of the tests to be redone or the ESCape option by making an appropriate indication on a touch screen at 591.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed is:

1. A muscle exercise machine comprising:
   an exercise element adapted for manipulation by a user;
   a processing unit, operationally connected to said exercise element, for controlling movement of said exercise element upon manipulation by a user;
   a display device, operationally connected to said processing unit;
   an input device, operationally connected to said processing unit;
   data storage means for storing therein names of users of said muscle exercise machine, dates of use of said exercise machine by users thereof and exercises performed by users on a date of use;
   name display means included in said processing unit, for displaying on said display device, at least some of the names of users of said muscle exercise machine;
   name input accepting means included in said processing unit, for accepting selection of one name at said input device, from the at least some of the names displayed on said display device;
   date display means included in said processing unit, for displaying on said display device, at least some of the dates of use of said muscle exercise machine for a selected one name;
   date input accepting means included in said processing unit, for accepting selection of one date at said input device, from the at least some of the dates of use displayed on said display device;
   test display means included in said processing unit, for displaying on said display device, at least some of the exercises performed on said muscle exercise machine for the selected one name and the selected one date;
   test input accepting means included in said processing unit, for accepting selection of one exercise at said input device, from the at least some of the exercises displayed on said display device; and
   movement controlling means included in said processing unit, for controlling movement of said exercise element to perform the selected one exercise upon manipulation of said exercise element by a user.

2. The muscle exercising machine of claim 1 wherein said name display means comprises:
   means for displaying a window on said display device, said window including a list of at least some of the names of users of said exercise machine;
   means for accepting selection of one of an up option and a down option at said input device; and,
   means for deleting at least one name at the bottom of the list and for adding at least one name at the top of the list in response to selection of the up option, and for deleting at least one name at the top of the list and adding at least one name at the bottom of the list in response to selection of the down option.

3. The muscle exercising machine of claim 2 wherein said window further comprises a selection area for displaying therein one name, and wherein said name input accepting means comprises means for accepting selection of the one name that appears in said selection area.

4. The muscle exercising machine of claim 3 wherein said means for deleting further comprises means for moving an immediately preceding name in the list into the selection area in response to selection of the up option, and for moving an immediately succeeding name in the list into the selection area in response to selection of the down option.

5. The muscle exercising machine of claim 1 wherein said data display means comprises:
   means for displaying a window on said display device, said window including a list at least some of the dates of use of said muscle exercise machine for a selected one name;
   means for accepting selection of one of an up option and a down option at said input device; and,
   means for deleting at least one date at the bottom of the list and for adding at least one date at the top of the list in response to selection of the up option, and for deleting at least one date at the top of the list and adding at least one date at the bottom of the list in response to selection of the down option.

6. The muscle exercising machine of claim 5 wherein said window further comprises a selection area for displaying therein one date, and wherein said data input accepting means comprises means for accepting selection of the one date that appears in said selection area.

7. The muscle exercising machine of claim 6 wherein said means for deleting further comprises means for moving an immediately preceding date in the list into the selection area in response to selection of the up option, and for moving an immediately succeeding date in the list into the selection area in response to selection of the down option.

8. The muscle exercising machine of claim 1 wherein said test display means comprises:
    means for displaying a window on said display device, said window including a list of at least some of the exercises performed on said muscle exercise machine for the selected one name and the selected one date;
    means for accepting selection of one of an up option and a down option at said input device; and,
    means for deleting at least one exercise at the bottom of the list and for adding at least one exercise at the top of the list in response to selection of the up option, and for deleting at least one exercise at the top of the list and adding at least one exercise at the bottom of the list in response to selection of the down option.

9. The muscle exercising machine of claim 8 wherein said window further comprises a selection area for displaying therein one exercise, and wherein said test input accepting means comprises means for accepting selection of the one exercise that appears in said selection area.

10. The muscle exercising machine of claim 9 wherein said means for deleting further comprises means for moving an immediately preceding exercise in the list into the selection area in response to selection of the up option, and for moving an immediately succeeding name in the list into the selection area in response to selection of the down option.

11. The muscle exercising machine of claim 1 wherein said data storage means comprises a nonvolatile magnetic data storage means.

12. The muscle exercising machine of claim 1 wherein said input device comprises a touch screen mounted on said display.

13. The muscle exercising machine of claim 1 further comprising recording mean, associated with said processing unit, for recording the performed selected exercise in said data storage means.

14. The muscle exercising machine of claim 1 wherein said movement controlling means comprises means for accepting modification of the selected one exercise, and for controlling said muscle exercising machine to perform the modified selected one exercise, upon manipulation of said exercise element by a user.

15. A muscle exercise machine comprising:
    an exercise element adapted for manipulation by a user;
    a processing unit, operationally connected to said exercise element, for controlling movement of said exercise element upon manipulation by a user;
    a display device, operationally connected to said processing unit;
    an input device, operationally connected to said processing unit;
    data storage means for storing therein names of exercise protocols usable on said muscle exercise machine, and corresponding exercise protocol parameters for each exercise protocol name;
    protocol display means included in said processing unit, for displaying a window on said display device, said window including a list of at least some of the names of exercise protocols usable on said muscle exercise machine;
    input direction accepting means included in said processing unit, for accepting selection of one of an up option and a down option at said input device;
    scroll means included in said processing unit, for deleting at least one exercise protocol at the bottom of the list and for adding at least one exercise protocol at the top of the list in response to selection of the up option, and for deleting at least one exercise protocol at the top of the list and for adding at least one exercise protocol at the bottom of the list in response to selection of the down option;
    protocol accepting means included in said processing unit, for accepting selection of one exercise protocol at said input device, from the at least some of the exercise protocols displayed in said window; and
    movement controlling means included in said processing unit, for controlling movement of said exercise element to perform exercise upon manipulation of said exercise element by a user, according to the exercise protocol parameters corresponding to the selected one exercise protocol.

16. The muscle exercising machine of claim 15 further comprising protocol retrieving means included in said processing unit, for accepting an instruction to retrieve an exercise protocol; and wherein said protocol display means is responsive to said protocol retrieving means 17. The muscle exercising machine of claim 15 wherein said window further comprises a selection area for displaying therein one exercise protocol, and wherein said protocol accepting means comprises means for accepting selection of the one exercise protocol that appears in said selection area.

18. The muscle exercising machine of claim 17 wherein said means for deleting further comprises means for moving an immediately preceding exercise protocol in the list into the selection area in response to selection of the up option, and for moving an immediately succeeding exercise protocol in the list into the selection area in response to selection of the down option.

19. The muscle exercising machine of claim 15 wherein said data storage means comprises a nonvolatile magnetic data storage means.

20. The muscle exercising machine of claim 15 wherein said input device comprises a touch screen mounted on said display.

21. The muscle exercising machine of claim 15 further comprising recording means included in said processing unit, for recording the performed selected exercise in said data storage means.

22. The muscle exercise machine of claim 15 further comprising:
    change of exercise means included in said processing unit, for accepting an instruction to modify an exercise protocol; and movement controlling means, responsive to said protocol accepting means for accepting selection of modified parameters for the selected one exercise protocol;

said movement controlling means controlling movement of said exercise element to perform exercise upon manipulation of said exercise element by a user, according to the modified parameters for the selected one exercise protocol.

23. The muscle exercise machine of claim 22 further comprising recording means, associated with said processing unit, for recording the modified parameters in said data storage means.

24. The muscle exercise machine of claim 23 wherein said recording means comprises:

means for accepting a modified exercise protocol name from said input device, and means for recording the modified protocol name and the modified parameters associated therewith in said data storage means.

25. The muscle exercising machine of claim 15 wherein said names of exercise protocols comprise standard exercise protocols and custom exercise protocols.

26. The muscle exercising machine of claim 25 wherein said standard exercise protocols comprise isokinetic, isometric and isotonic exercise protocols.

27. A muscle exercising machine comprising:
an exercise element for manipulation by a user;
a processing unit, operationally connected to said exercise element, for controlling movement of said exercise element upon manipulation by a user;
a display device, operationally connected to said processing unit;
an input device, operationally connected to said processing unit;
data storage means for storing therein names of exercise related data of a first type and corresponding exercise data of the first type;
data selection accepting means included in said processing unit, for accepting selection of said first type of data to be displayed on said display device;
window display means included in said processing unit, for displaying a window on said display device, said window including a list of at least some of the names of the first type of data and a selection area for displaying therein one name of the first type of data;
input direction accepting means for accepting selection of one of an up option and a down option at said input device;
scroll upward means for deleting at least one name at the bottom of the list, for adding at least one name at the top of the list and for moving an immediately preceding name in the list into the selection area, in response to selection of the up option;
scroll downward means for deleting at least one name at the top of the list, for adding at least one name at the bottom of the list and for moving an immediately succeeding name on the list into the selection area, in response to selection of the down option;
name selection accepting means included in said processing unit, for accepting selection of the name in the selection area; and,
movement controlling means includes in said processing unit, for controlling movement of said exercise element to perform exercise according to the exercise data corresponding to the selected name.

28. The muscle exercising machine of claim 27 wherein said input device comprises a touch screen mounted on said display.

29. The muscle exercising machine of claim 28 wherein said input direction accepting means comprises means for displaying an up box at the top of said window and a down box at the bottom of said window, and for accepting selection of said up box and said down box at said touch screen.

30. The muscle exercising machine of claim 27 wherein said data storage means comprises a nonvolatile magnetic data storage means.

31. A method of controlling a muscle exercise machine having an exercise element adapted for manipulation by a user, a processing unit for controlling movement of the exercise element upon manipulation by a user, and a display device, a data storage means and an input device operationally connected to the processing unit; said method comprising the steps of:

storing names of users of the muscle exercise machine, dates of use of said exercise machine by users thereof and exercises performed by users on a date of use in the data storage means;

displaying on the display device, at least some of the names of users of the muscle exercise machine;

accepting selection of one name at the input device, from the at least some of the names displayed on the display device;

displaying on the display device, at least some of the dates of use of the muscle exercise machine for a selected one name;

accepting selection of one date at the input device, from the at least some of the dates of use displayed on the display device;

displaying on the display device, at least some of the exercises performed on the muscle exercise machine for the selected one name and the selected one date;

accepting selection of one exercise at the input device, from the at least some of the exercises displayed on the display device; and, controlling movement of the exercise element to perform the selected one exercise upon manipulation of the exercise element by a user.

32. The method of claim 31 wherein said name displaying step comprises the steps of:

displaying a window on the display device, the window including a list of at least some of the names of users of the exercise machine;

accepting selection of one of an up option and a down option at the input device; and, deleting at least one name at the bottom of the list and adding at least one name at the top of the list in response to selection of the up option, and deleting at least one name at the top of the list and adding at least one name at the bottom of the list in response to selection of the down option.

33. The method claim 32 wherein the window further comprises a selection area for displaying therein one name, and wherein said name selection accepting step comprises the step of accepting selection of the one name that appears in said selection area.

34. The method of claim 33 wherein said deleting step further comprises the step of moving an immediately preceding name in the list into the selection area in response to selection of the up option, and moving an immediately succeeding name in the list into the selection area in response to selection of the down option.

35. The method of claim 31 wherein said date displaying step comprises the steps of:

displaying a window on the display device, the window including a list at least some of the dates of use of the muscle exercise machine for a selected one name;

accepting selection of one of an up option and a down option at the input device; and, deleting at least one date at the bottom of the list and adding at least one date at the top of the list in response to selection of the up option, and deleting at least one date at the top of the list and adding at least one date at the bottom of the list in response to selection of the down option.

36. The method of claim 35 wherein the window further comprises a selection area for displaying therein one date, and wherein said date selection accepting step comprises the step of accepting selection of the one date that appears in the selection area.

37. The method of claim 36 wherein the deleting step further comprises the steps of moving an immediately preceding date in the list into the selection area in response to selection of the up option, and moving an immediately succeeding date in the list into the selection area in response to selection of the down option.

38. The method of claim 31 wherein said exercise displaying step comprises the steps of:

displaying a window on the display device, the window including a list of at least some of the exercises performed on the muscle exercise machine for the selected one name and the selected one date;

accepting selection of one of an up option and a down option at the input device; and, deleting at least one exercise at the bottom of the list and adding at least one exercise at the top of the list in response to selection of the up option, and deleting at least one exercise at the top of the list and adding at least one exercise at the bottom of the list in response to selection of the down option.

39. The method of claim 38 wherein the window further comprises a selection area for displaying therein one exercise, and wherein said exercise accepting step comprises the step of accepting selection of the one exercise that appears in the selection area.

40. The method of claim 39 wherein said deleting step further comprises the steps of moving an immediately preceding exercise in the list into the selection area in response to selection of the up option, and moving an immediately succeeding name in the list into the selection area in response to selection of the down option.

41. The method of claim 31 wherein said data storage means comprises a nonvolatile magnetic data storage means.

42. The method of claim 31 wherein said input device comprises a touch screen mounted on said display.

43. The method of claim 31 further comprising the step of recording the performed selected exercise in the data storage means.

44. The method of claim 31 wherein the movement controlling step comprises the steps of accepting modification of the selected one exercise, and controlling said muscle exercising machine to perform the modified selected one exercise, upon manipulation of the exercise element by a user.

45. A method of controlling a muscle exercise machine having an exercise element adapted for manipulation by a user, a processing unit for controlling movement of the exercise element upon manipulation by a user, and a display device, a data storage means and an input device operationally connected to the processing unit; said method comprising the steps of:

storing names of exercise protocols usable on the muscle exercise machine, and corresponding exercise protocol parameters for each exercise protocol name, in the data storage means;

displaying a window on the display device, said window including a list of at least some of the names of exercise protocols usable on the muscle exercise machine;

accepting selection of one of an up option and a down option at the input device;

deleting at least one exercise protocol at the bottom of the list and adding at least one exercise protocol at the top of the list in response to selection of the up option, and deleting at least one exercise protocol at the top of the list and adding at least one exercise protocol at the bottom of the list in response to selection of the down option;

accepting selection of one exercise protocol at the input device, from the at least some of the exercise protocols displayed in said window; and controlling movement of said exercise element to perform exercise upon manipulation of said exercise element by a user, according to the exercise protocol parameters corresponding to the selected one exercise protocol.

46. The method of claim 45 wherein said window displaying step is preceded by accepting an instruction to retrieve an exercise protocol.

47. The method of claim 45 wherein said window further comprises a selection area for displaying therein one exercise protocol, and wherein said accepting selection step comprises the step of accepting selection of the one exercise protocol that appears in said selection area.

48. The method of claim 47 wherein said deleting step further comprises the step of moving an immediately preceding exercise protocol in the list into the selection area in response to selection of the up option, and moving an immediately succeeding exercise protocol in the list into the selection area in response to selection of the down option.

49. The method of claim 45 wherein said data storage means comprises a nonvolatile magnetic data storage means.

50. The method of claim 45 wherein said input device comprises a touch screen mounted on said display.

51. The method of claim 45 further comprising the step of recording the performed selected exercise in said data storage means.

52. The method claim 45 further comprising the steps of:

accepting an instruction to modify an exercise protocol; and accepting selection of modified parameters for the selected one exercise protocol; and wherein said controlling step comprises the step of controlling movement of said exercise element to perform exercise upon manipulation of said exercise element by a user, according to the modified parameters for the selected one exercise.

53. The method of claim 52 further comprising the step of recording the modified parameters in said data storage means.

54. The method of claim 53 wherein said recording step comprises the steps of:

accepting a modified exercise protocol name from the input device and recording the modified protocol name and the modified parameters associated therewith in the data storage means.

55. The method of claim 45 wherein said names of exercise protocols comprise standard exercise protocols and custom exercise protocols.

56. The method of claim 55 wherein said standard exercise protocols comprise isokinetic, isometric and isotonic exercise protocols.

57. A method of controlling a muscle exercise machine having an exercise element adapted for manipulation by a user, a processing unit for controlling movement of the exercise element upon manipulation by a user, and a display device, a data storage means and an input device operationally connected to the processing unit; said method comprising the steps of:

storing names of exercise related data of a first type and corresponding exercise data of the first type in the data storage means;
 accepting selection of the first type of data to be displayed on the display device;
 displaying a window on the display device, the window including a list of at least some of the names of the first type of data and a selection area for displaying therein one name of the first type of data;
 accepting selection of one of an up option and a down option at the input device;
 deleting at least one name at the bottom of the list, adding at least one name at the top of the list and moving an immediately preceding name in the list into the selection area, in response to selection of the up option;
 deleting at least one name at the top of the list, adding at least one name at the bottom of the list and moving an immediately succeeding name on the list into the selection area, in response to selection of the down option;
 accepting selection of the name in the selection area; and,
 controlling movement of the exercise element to perform exercise according to the exercise data corresponding to the selected name.

58. The method of claim 57 wherein said input device comprises a touch screen mounted on said display.

59. The method of claim 58 wherein said the up and down option accepting step comprises the steps of displaying an up box at the top of said window and a down box at the bottom of said window, and for accepting selection of said up box and said down box at said touch screen.

60. The method of claim 57 wherein said data storage means comprises a nonvolatile magnetic data storage means.

* * * * *